United States Patent
Coates et al.

(10) Patent No.: US 11,851,416 B2
(45) Date of Patent: Dec. 26, 2023

(54) SYSTEMS AND METHODS FOR REGIOSELECTIVE CARBONYLATION OF 2,2-DISUBSTITUTED EPOXIDES FOR THE PRODUCTION OF ALPHA,ALPHA-DISUBSTITUTED BETA-LACTONES

(71) Applicant: Cornell University, Ithaca, NY (US)

(72) Inventors: Geoffrey W. Coates, Lansing, NY (US); Jessica Rachel Lamb, Cambridge, MA (US); Kristine Klimovica, St. Paul, MN (US); Aran Kathleen Hubbell, Ithaca, NY (US)

(73) Assignee: Cornell University, Ithaca, NY (US)

( * ) Notice: Subject to any disclaimer, the term of this patent is extended or adjusted under 35 U.S.C. 154(b) by 368 days.

(21) Appl. No.: 16/936,322

(22) Filed: Jul. 22, 2020

(65) Prior Publication Data

US 2021/0024479 A1   Jan. 28, 2021

Related U.S. Application Data

(60) Provisional application No. 62/877,135, filed on Jul. 22, 2019.

(51) Int. Cl.
| | | |
|---|---|---|
| *C07D 305/12* | (2006.01) | |
| *C08G 63/08* | (2006.01) | |
| *B01J 31/18* | (2006.01) | |
| *C07C 45/58* | (2006.01) | |
| *C08G 63/84* | (2006.01) | |
| *C07F 5/06* | (2006.01) | |

(52) U.S. Cl.
CPC .......... *C07D 305/12* (2013.01); *B01J 31/184* (2013.01); *B01J 31/1825* (2013.01); *C07C 45/58* (2013.01); *C07F 5/069* (2013.01); *C08G 63/08* (2013.01); *C08G 63/84* (2013.01); *B01J 2231/34* (2013.01); *B01J 2531/31* (2013.01)

(58) Field of Classification Search
CPC ..... C07D 305/12; C07D 307/20; C08G 63/82
See application file for complete search history.

(56) References Cited

U.S. PATENT DOCUMENTS

2003/0162961 A1 * 8/2003 Coates ................ C07D 265/06
540/200

OTHER PUBLICATIONS

Getzler et al Synthesis of beta-Lactones: A Highly Active and Selective Catalyst for Epoxide Carbonylation, J. Am. Chem. Soc., vol. 124, No. 7, 2002, pp. 1174-1175, published on Jul. 2002.*
Lee et al Synthesis of â-Lactones by the Regioselective, Cobalt and Lewis Acid Catalyzed Carbonylation of Simple and Functionalized Epoxides, J. Org. Chem. 2001, 66, 5424-5426, Published on Web Jul. 19, 2001.*
Mahadevan, et al., "[Lewis Acid]+[Co(CO)4]-Complexes: A Versatile Class of Catalysts for Carbonylative Ring Expansion of Epoxides and Aziridines," Angew. Chem. Int. Ed. 2002, 41, No. 15, all enclosed pages cited.

* cited by examiner

*Primary Examiner* — Gregory Listvoyb
(74) *Attorney, Agent, or Firm* — Hodgson Russ LLP

(57) ABSTRACT

Provided are methods of producing carbonyl compounds (e.g., carbonyl containing compounds) and catalysts for producing carbonyl compounds. Also provided are methods of making polymers from carbonyl compounds and polymers formed from carbonyl compounds. A method may produce carbonyl compounds, such as, for example α,α-disubstituted carbonyl compounds (e.g., α,α-disubstituted β-lactones). The polymers may be produced from α,α-disubstituted β-lactones, which may be produced by a method described herein.

13 Claims, 17 Drawing Sheets
(15 of 17 Drawing Sheet(s) Filed in Color)

A. Cycloaddition of Dimethylketene and Formaldehyde

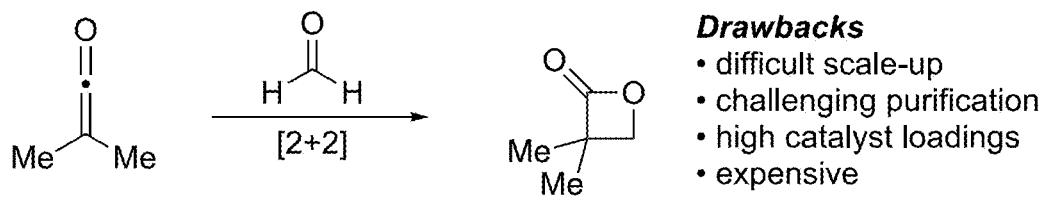

*Drawbacks*
- difficult scale-up
- challenging purification
- high catalyst loadings
- expensive

B. Ring Closure of 3-Chloropivalic Acid

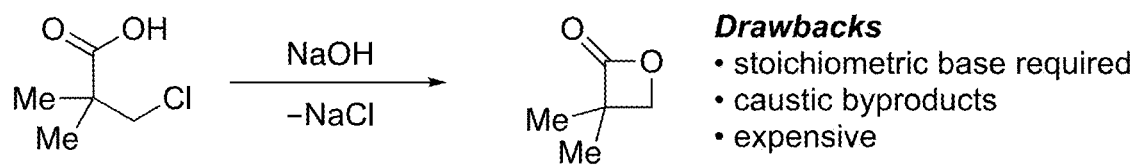

*Drawbacks*
- stoichiometric base required
- caustic byproducts
- expensive

C. This work: Regioselective Carbonylation of Isobutylene Oxide

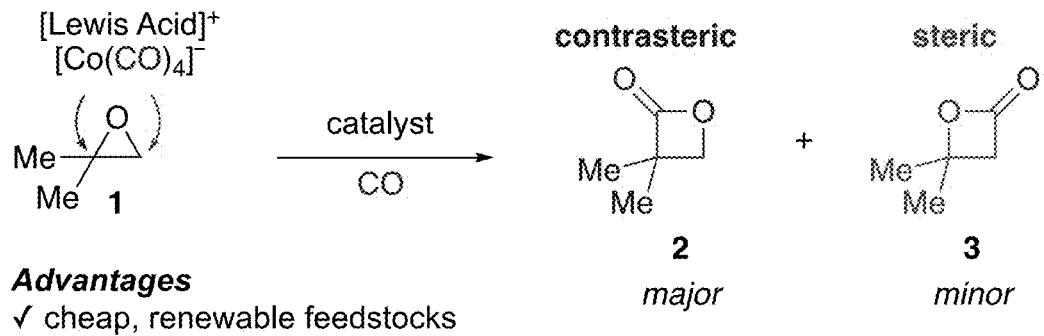

*Advantages*
- ✓ cheap, renewable feedstocks
- ✓ atom-economical
- ✓ no stoichiometric additives

*Strategy:* design and synthesize a contrasteric-selective catalyst

Figure 1

A. Proposed Pathways to Side Products 10 and 12
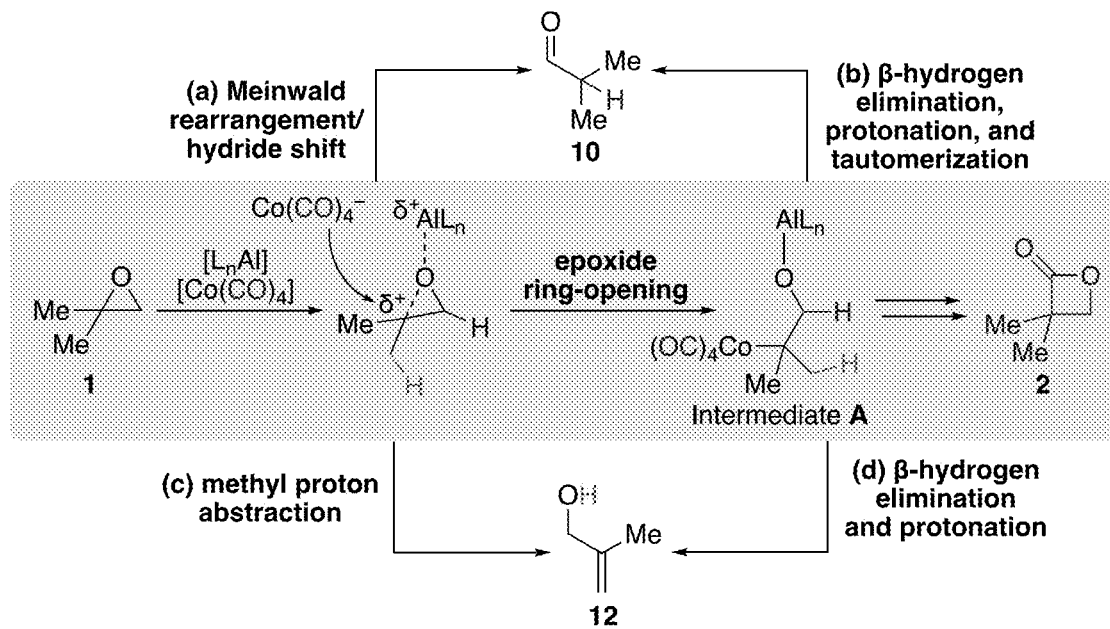
B. Resulting MPVO Reaction
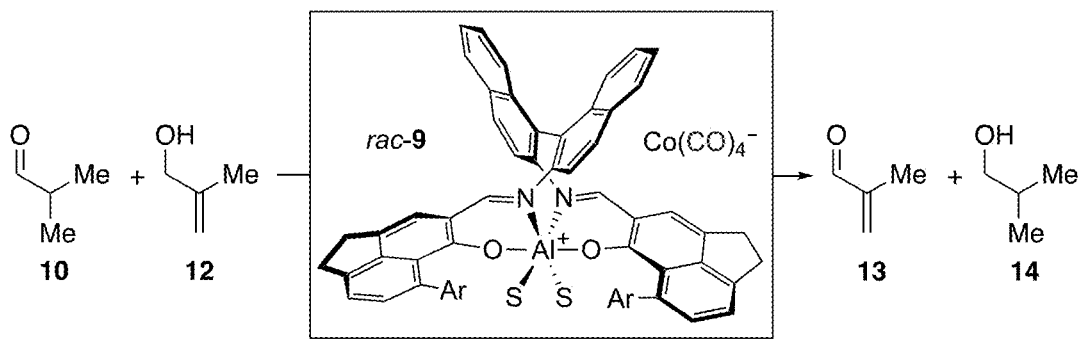
Figure 4

A
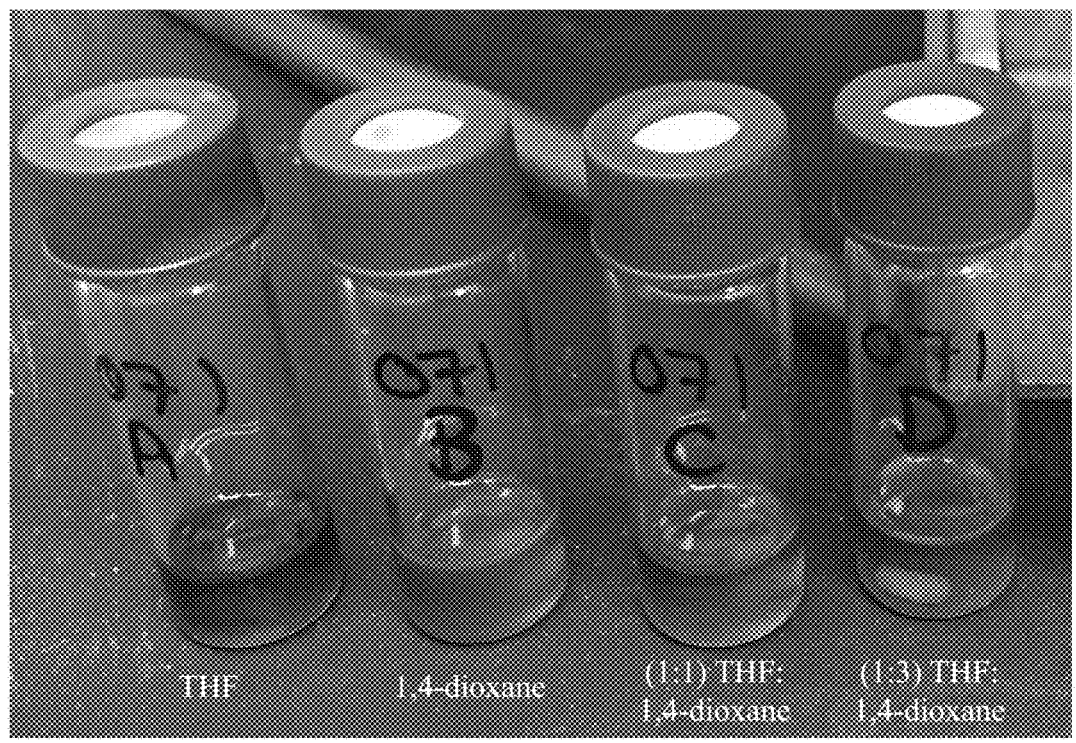
B
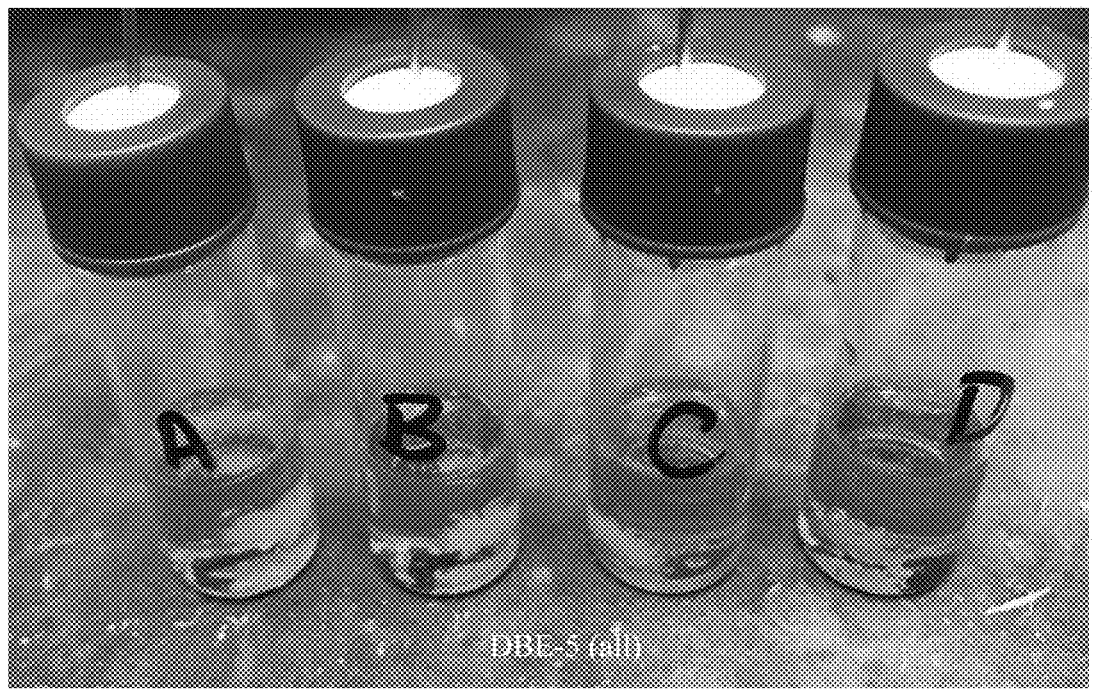
Figure 9

US 11,851,416 B2

SYSTEMS AND METHODS FOR REGIOSELECTIVE CARBONYLATION OF 2,2-DISUBSTITUTED EPOXIDES FOR THE PRODUCTION OF ALPHA,ALPHA-DISUBSTITUTED BETA-LACTONES

CROSS REFERENCE TO RELATED APPLICATIONS

This application claims priority to U.S. Provisional Application No. 62/877,135, filed on Jul. 22, 2019, the disclosure of which is incorporated herein by reference.

STATEMENT REGARDING FEDERALLY SPONSORED RESEARCH

This invention was made with government support under grant no. DE-FG02-05ER15687 awarded by the Department of Energy. The government has certain rights in the invention.

BACKGROUND OF THE DISCLOSURE

Poly(pivalolactone) (PPVL) has shown promise in the textile fiber industry due to its high crystallinity, thermal stability, elastic recovery, chemical resistance, and low deformation at elevated temperatures. The chemical stability of PPVL, which is superior to that of PET fibers, is attributed to its methyl groups adjacent to the carbonyl. This α-disubstitution eliminates the presence of α protons that can be abstracted intramolecularly, a known polyhydroxyalkanoate reaction pathway that leads to chain scission and polymer degradation. Due to these desirable physical properties, two processes for the polymerization of the pivalolactone monomer (PVL) were successfully industrialized at pilot-plant scale. However, the cost of PVL production has proved to be economically unfeasible, limiting the overall success of PPVL commercialization.

The two most common syntheses of pivalolactone include: (1) the (formal) [2+2] cycloaddition of dimethylketene and formaldehyde and (2) the ring-closure of 3-chloropivalic acid. The cycloaddition procedure requires precise control of reaction conditions and, unfortunately, side product formation complicates both scale-up and purification. Additionally, 3-chloropivalic acid ring-closure requires stoichiometric base and separations from metal halides are challenging, rendering the synthesis impractical for large-scale production. In addition to these commonly employed processes, Dow Chemical developed a method for the carbonylation of allylic carbonates. However, superstoichiometric amounts of strong acid and low yields (15%) limit the synthetic utility of this transformation. Others have reported the palladium-catalyzed β-C(sp³)-H functionalization of alkyl carboxylic acids, an advance that generates a variety of α,α-disubstituted β-lactones, including pivalolactone (50% yield from pivalic acid). However, this method requires 10 mol % of a palladium catalyst, near stoichiometric base, and superstoichiometric oxidant. Ring-expansion carbonylation of 2,2-disubstituted epoxides is well-known, and several generations of catalysts have been identified. Others have developed the first carbonylation of isobutylene oxide in 1994 using a $Co_2(CO)_8$/3-hydroxypyridine catalyst. However, this system selectively inserted CO at the less-substituted position to form the β,β-disubstituted lactone and produced various side products. In 2002, carbonylation of isobutylene oxide using $[Cp2Ti(THF)_2]^+[Co(CO)_4]^-$ and $[(salph)Al(THF)_2]^+[Co(CO)_4]^-$ (salph=N,N'-o-phenylenebis(3,5-di-tert-butylsalicylideneimine), THF=tetrahydrofuran) catalysts was described, but these methods still favored the production of the β,β-disubstituted lactone (20:80 and 8:92 ratio of α,α-:β,β-disubstituted lactone, respectively). Also previously developed was a highly regioselective carbonylation of 2,2-disubstituted epoxides for the near-exclusive formation of β,β-disubstituted β-lactones using porphyrin and salen-based catalysts. The high steric selectivity demonstrated by these four reports suggests that achieving large yields of α,α-disubstituted lactones using conventional carbonylation catalysts would be exceptionally challenging.

SUMMARY OF THE DISCLOSURE

The present disclosure provides methods of producing carbonyl compounds (e.g., carbonyl containing compounds) and catalysts for producing carbonyl compounds. The present disclosure also provides methods of making polymers from carbonyl compounds and polymers formed from carbonyl compounds.

In an aspect, the present disclosure provides methods of producing carbonyl compounds. A method may produce carbonyl compounds, such as, for example α,α-disubstituted carbonyl compounds (e.g., α,α-disubstituted β-lactones). The methods are based on carbonylation at the more substituted position of a cyclic ether.

In an aspect, the present disclosure provides catalysts. The catalysts may be suitable in reactions for producing carbonyl compounds.

In an aspect, the present disclosure provides methods of producing a catalyst of the present disclosure. In various examples, a catalyst is made by a method of the present disclosure.

In an aspect, the present disclosure provides carbonyl compounds (e.g., α,α-disubstituted β-lactones). The carbonyl compounds (e.g., α,α-disubstituted β-lactones) may be produced by a method of the present disclosure.

In an aspect, the present disclosure provides polymers. The polymers may be copolymers and/or homopolymers. The polymers may be produced from α,α-disubstituted (3-lactones, which may be produced by methods of the present disclosure.

In an aspect, the present disclosure provides methods of making polymers (e.g., copolymers and/or homopolymers produced from α,α-disubstituted β-lactones produced by methods of the present disclosure).

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

FIG. 1 shows a scheme of pivalolactone syntheses: (A) cycloaddition of dimethylketene and formaldehyde, (B) ring closure of 3-chloropivalic acid, and (C) an alternative regioselective carbonylation method.

FIG. 4 shows a scheme showing (A) proposed pathways to side products 10 and 12 and (B) the resulting Meerwein-Ponndorf-Verley-Oppenauer reaction.

FIG. 9 shows qualitative evidence for catalyst decomposition in certain solvents. (A) shows table 2, entries 1-4. (B) shows table 2, entry 10.

DETAILED DESCRIPTION OF THE DISCLOSURE

Figure 2:
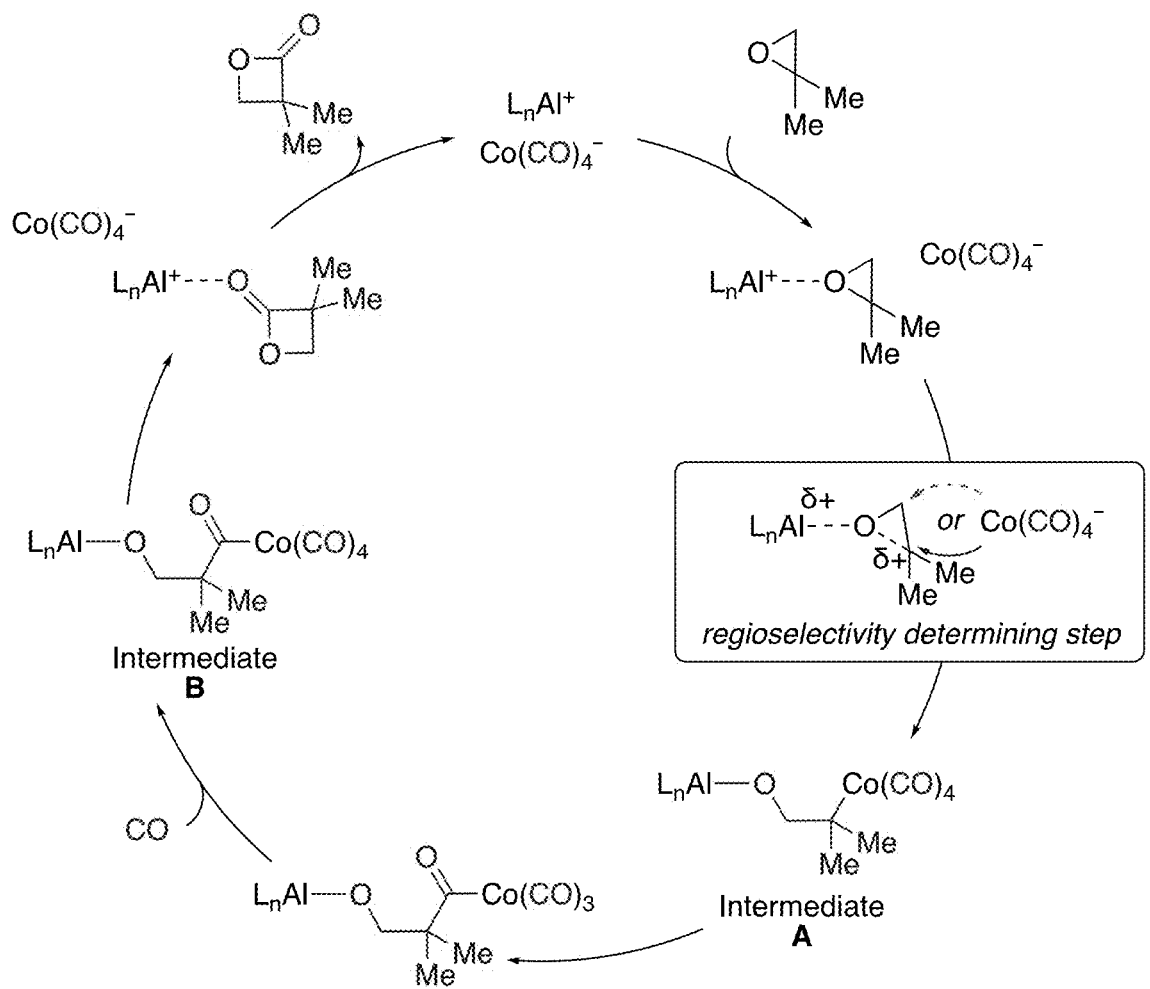
FIG. 2 shows a scheme showing a proposed mechanism for the contrasteric carbonylation of isobutylene oxide.

Although subject matter of the present disclosure is described in terms of certain embodiments and examples, other embodiments and examples, including embodiments and examples that do not provide all of the benefits and features set forth herein, are also within the scope of this disclosure. For example, various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either the lower limit value or the upper limit value) and ranges between the values of the stated range.

As used herein, unless otherwise indicated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent radicals, such as, for example, divalent radicals, trivalent radicals, and the like) Illustrative examples of groups include:

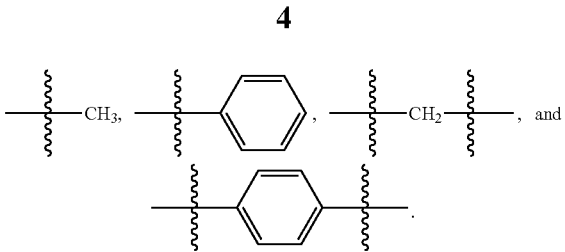

As used herein, unless otherwise indicated, the term "alkyl group" refers to branched or unbranched, linear saturated hydrocarbon groups and/or cyclic hydrocarbon groups. Examples of alkyl groups include, but are not limited to, methyl groups, ethyl groups, propyl groups, butyl groups, isopropyl groups, tert-butyl groups, cyclopropyl groups, cyclopentyl groups, cyclohexyl groups, and the like. Alkyl groups may be saturated groups. Alkyl groups may be cyclic alkyl groups (e.g., carbocycles). For example, an alkyl group is a $C_1$ to $C_{30}$ alkyl group, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$). Alkyl groups may be unsubstituted or substituted with one or more substituents. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group and the like), aryl groups, halogenated aryl groups, alkoxide groups, amine groups, nitro groups, carboxylate groups, carboxylic acids, ether groups, alcohol groups, alkyne groups (e.g., acetylenyl groups and the like), and the like, and combinations thereof.

As used herein, unless otherwise indicated, the term "aryl group" refers to $C_5$ to $C_{30}$ aromatic or partially aromatic carbocyclic groups, including all integer numbers of carbons and ranges of numbers of carbons therebetween (e.g., $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$). Aryl groups may be referred to as aromatic groups. Aryl groups may be polyaryl groups, such as, for example, fused rings, biaryl groups, or a combination thereof. Aryl groups may be unsubstituted or substituted with one or more substituents. Examples of substituents include, but are not limited to, halogens (—F, —Cl, —Br, and —I), aliphatic groups (e.g., alkyl groups, alkenyl groups, alkynyl groups, and the like), aryl groups, alkoxides, carboxylates, carboxylic acids, ether groups, and the like, and combinations thereof. Examples of aryl groups include, but are not limited to, phenyl groups, biaryl groups (e.g., biphenyl groups and the like), fused ring groups (e.g., naphthyl groups and the like), hydroxybenzyl groups, tolyl groups, xylyl groups, furanyl groups, benzofuranyl groups, indolyl groups, imidazolyl groups, benzimidazolyl groups, pyridinyl groups, and the like.

The present disclosure provides methods of producing carbonyl compounds (e.g., carbonyl containing compounds) and catalysts for producing carbonyl compounds. The present disclosure also provides methods of making polymers from carbonyl compounds and polymers formed from carbonyl compounds.

In an aspect, the present disclosure provides methods of producing carbonyl compounds. A method may produce carbonyl compounds, such as, for example α,α-disubstituted carbonyl compounds (e.g., α,α-disubstituted β-lactones).

The methods are based on carbonylation at the more substituted position of a cyclic ether.

A method may comprise providing a reaction mixture comprising a 2,2-disubstituted epoxide, a solvent or two or more solvents (e.g., a polar, aprotic solvent or two or more polar, aprotic solvents), and a catalyst (e.g., a catalyst of the present disclosure) in a vessel (e.g., a sealed vessel); contacting (e.g., pressurizing) the reaction mixture with carbon monoxide; and holding the reaction mixture (e.g., stirring the reaction mixture) for a selected time (e.g., 1 minute (m or min) to 96 hours (h or hr), including every second value and range therebetween) and/or temperature (e.g., −50 to 200° C., including every 0.1° C. value and range therebetween, such as, for example, 18 to 25° C. (e.g., 24° C.)), where the carbonyl compound is produced. In various examples, the catalyst may be formed in situ when providing a reaction mixture (e.g., from a reaction with a catalytic precursor and a metal source, such as, for example, a cobalt metal source, such as, for example, $NaCo(CO)_4$). A method of the present disclosure produces an α,α-disubstituted carbonyl compound (e.g., α,α-disubstituted β-lactone). In various examples, the reaction mixture is vented and/or the carbonyl compound (e.g., α,α-disubstituted β-lactone) is isolated. The major (e.g., highest yield product relative to the other products formed) carbonyl compound produced is the result of a carbonylation at the more substituted position on the 2,2-disubstituted epoxide. The method may be carried out in a single vessel (e.g., without separating or isolating various possible intermediates, which may be referred to as a "one-pot reaction").

A method may provide a mixture of lactone products (e.g., a mixture of α,α-disubstituted β-lactones and β,β-disubstituted β-lactones). In various examples, the ratio (e.g., lactone distribution) of α,α-disubstituted β-lactone to β,β-disubstituted β-lactone is 50:50 to >99:<1, including all integer ratio values and ranges therebetween (e.g., 50:50, 60:40, 70:30, 75:25, 80:20, 85:15, 90:10, 91:9, 92:8, 93:7, 94:6, 95:5, 96:4, 97:3, 98:2, 99:1: >99:1, or >99:<1). In various examples, the ratio (e.g., lactone distribution) of α,α-disubstituted β-lactone to β,β-disubstituted β-lactone Various catalyst concentrations are suitable in a method of the present disclosure. The catalyst may be present in the reaction mixture at a concentration of 0.01 to 10 mol %, including all 0.01 mol % values and ranges therebetween (e.g., 0.05 to 10 mol % or 1 mol %). The mol % is relative to the amount of 2,2-disubstituted epoxide in the reaction mixture.

Various solvents are suitable in a method of producing a carbonyl compound (e.g., α,α-disubstituted β-lactone). The reaction mixture may comprise one solvent or a combination of two or more solvents. Non-limiting examples of solvents include ethereal solvents, such as, for example, THF, 1,3-dioxane, 1,4-dioxane, diethyl ether, toluene, dibasic esters (e.g., DBE-1, DBE-2, DBE-3, DBE-4, DBE-5, DBE-6, DBE-7, DBE-8, DBE-9, DBE-10, and the like), $^iPr_2O$, and the like, acetates, such as, for example, ethyl acetate, $^tbutyl$ acetate, and the like, and the like, and combinations thereof. In various examples, the solvent is THF. In various examples, two or more solvents are used and the solvents are THF and 1,4-dioxane, where the ratio of 1,4-dioxane to THF is 3:1 to 1:3, including every 0.1 ratio value and range therebetween (e.g., 3:1 or 1:1 1,4-dioxane to THF). In various other examples, the solvent is DBE-5. In various examples, the solvent present in the reaction mixture is 0.10 to 12 M, including every 0.01 M value and range therebetween (e.g., 0.5 M), with respect to the 2,2-disubstituted epoxide. In various examples the remainder of the reaction mixture is one or more solvent(s).

Various pressures of CO are suitable in a method of producing a carbonyl compound (e.g., α,α-disubstituted β-lactone). For example, the reaction mixture is pressurized to 0.1 to 2000 psig with CO, including every 0.1 psig value and range therebetween (e.g., 900 psig).

Various catalysts are suitable for a method of producing a carbonyl compound (e.g., α,α-disubstituted β-lactone). Suitable catalysts are provided herein.

Various 2,2-disubstituted epoxides may be used in a method of producing a carbonyl compound (e.g., α,α-disubstituted β-lactone). For example, the 2,2-disubstituted epoxide has the following structure:

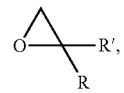

where R and R' is independently a substituted or unsubstituted alkyl group that is the same or different or R and R' are connected such that they form a substituted or unsubstituted carbocycle or substituted or unsubstituted heterocycle. The substituted or unsubstituted alkyl groups may be linear or branching alkyl groups or cyclic alkyl groups. The linear or branching alkyl groups may have a longest linear chain of 1 to 10 carbons (e.g., 1, 2, 3, 4, 5, 6, 7, 8, 9, or 10). In various examples, the 2,2-disubstituted epoxide are spirocyclic (e.g., the non-epoxide ring of the spirocycle is a $C_3$ to $C_{12}$ ($C_3$, $C_4$, $C_5$, $C_6$, $C_7$, $C_8$, $C_9$, $C_{10}$, $C_{11}$, or Cu) ring, which may be a rigid ring). Examples of $C_3$ to $C_{12}$ rings include, but are not limited to, substituted or unsubstituted cyclopropanes, substituted or unsubstituted cyclobutanes, substituted or unsubstituted cyclopentanes, substituted or unsubstituted cyclohexanes, substituted or unsubstituted cycloheptanes, substituted or unsubstituted cyclooctanes, substituted or unsubstituted cyclononanes, substituted or unsubstituted cyclodecanes, substituted or unsubstituted cycloundecanes, and substituted or unsubstituted cyclododecanes, and the like.

In various examples, the 2,2-disubstituted epoxide is chosen from:

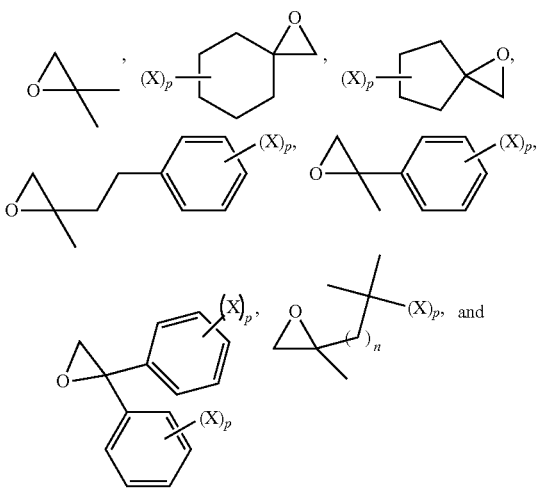

-continued

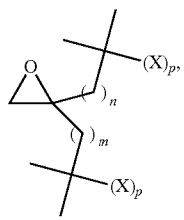

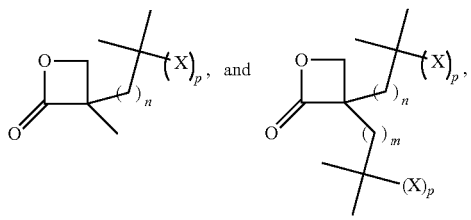, and where each X at each occurrence is independently chosen from H, alkoxy (e.g., OMe, OEt, O$^i$Pr, OSiMe$_3$, OSiMe$_2$$^t$Bu and the like), alkyl (e.g., Me, $^t$Bu, Cl, F, CF$_3$, $^i$Pr, Et, and the like), aryl groups (e.g., Ph, ether substituted aryl, and the like), halides (Br, Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like, each p independently is 0-10 (1, 2, 3, 4, 5, 6, 7, 8, 9, or 10), n is 0-11 (1, 2, 3, 4, 5, 6, 7, 8, 9, 10, or 11), and m is 0-11 (1, 2, 3, 4, 5, 6, 7, 8, 9, 10, or 11). In various examples, the 2,2-disubstituted epoxide is chosen from:

where each X at each occurrence is independently chosen from H, alkoxy groups (e.g., OMe, OEt, O$^i$Pr, and the like), alkyl groups (e.g., Me, $^t$Bu, Cl, F, CF$_3$, Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like, each p independently is 0-10 (1, 2, 3, 4, 5, 6, 7, 8, 9, or 10), n is 0-11 (1, 2, 3, 4, 5, 6, 7, 8, 9, 10, or 11), and m is 0-11 (1, 2, 3, 4, 5, 6, 7, 8, 9, 10, or 11).

In various examples, the carbonyl compound (e.g., α,α-disubstituted β-lactone) is chosen from:

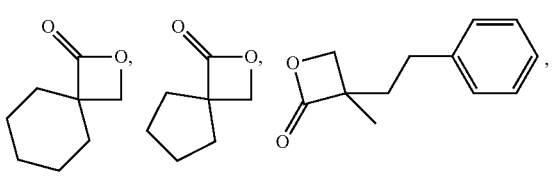

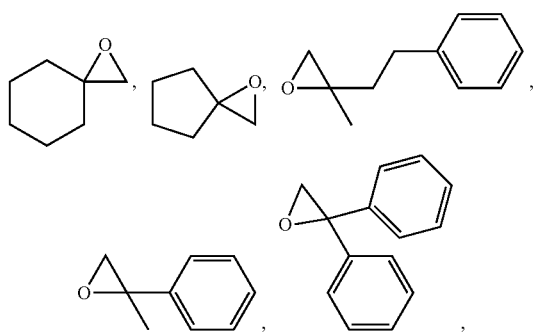

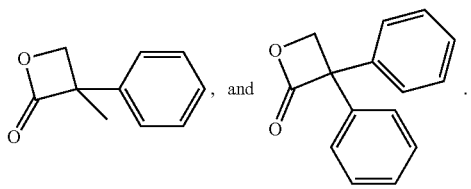, and and the like.

Various carbonyl compounds (e.g., α,α-disubstituted β-lactones) may be produced by a method of the present disclosure. For example, the carbonyl compound (e.g., α,α-disubstituted β-lactone) has the following structure:

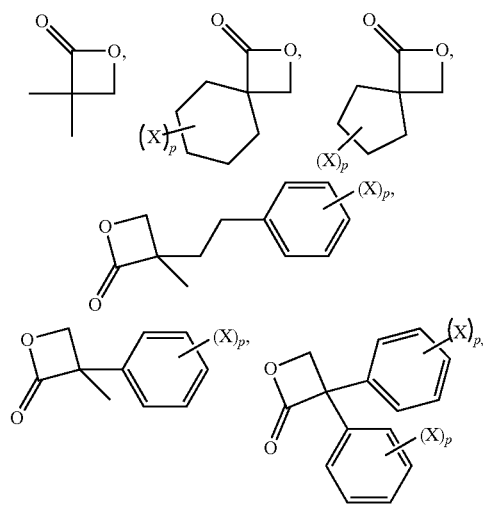

In an aspect, the present disclosure provides catalysts. The catalysts may be suitable in reactions for producing carbonyl compounds.

The catalyst may comprise a cationic Lewis acid and an anionic metal carbonyl. The catalyst may have the following formula: [Lewis acid]$^{z+}${[QM(CO)$_x$]$^{w-}$}$_y$, where Q is any ligand and is optional, M is a transition metal chosen from transition metals of Groups 4, 5, 6, 7, 8, 9, and 10 of the periodic table of elements (e.g., cobalt) and z is the valence of the Lewis acid and ranges from 1 to 6 (1, 2, 3, 4, 5, or 6), w is the charge of the metal carbonyl and ranges from 1 to 4 (1, 2, 3, or 4), y is a number such that w times y equals z and x is a number such as to provide a stable anionic metal carbonyl for {[QM(CO)$_x$]$^{w-}$}$_y$ and ranges from 1 to 9 (1, 2, 3, 4, 5, 6, 7, 8, or 9). The reaction mixture containing the catalyst may further comprise an additional anion, such as, for example, tetraphenyl borate.

In various examples, the Lewis acid has the following structure:

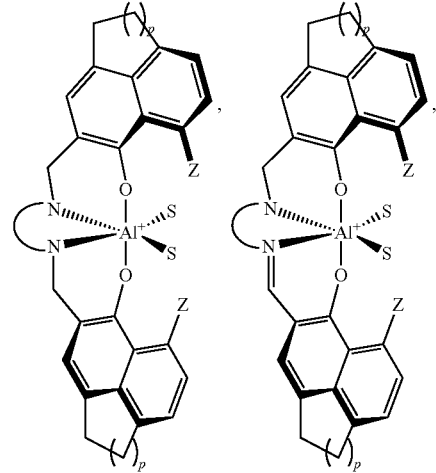

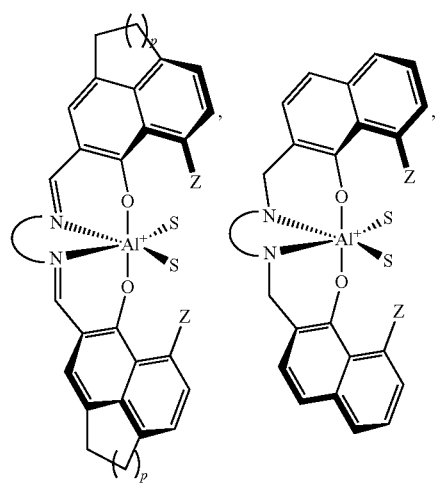

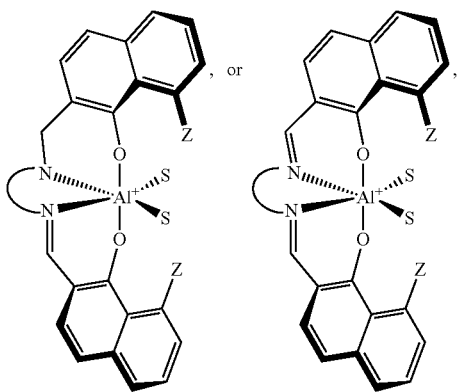

(diamine bridge) is chosen from:

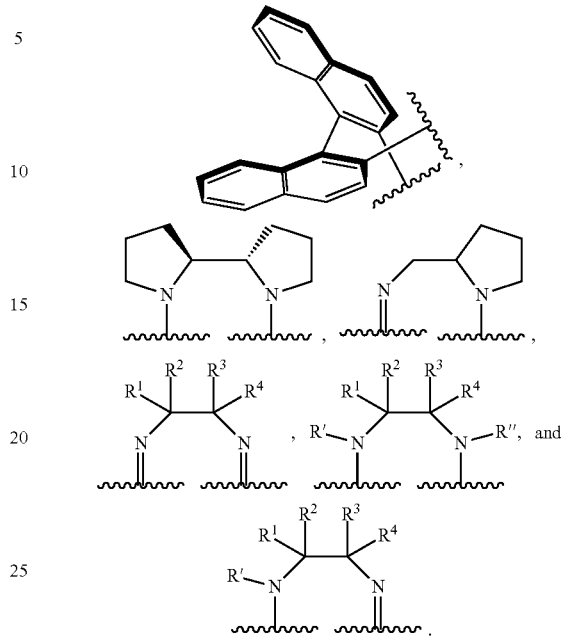

$R'$, $R''$, $R^2$, $R^3$, and $R^4$ are each independently chosen from H, alkyl groups (e.g., Me, $^tBu$, $C_1$, F, $CF_3$, $^iPr$, Et, and the like), and aryl groups (e.g., phenyl groups and the like);

Z is H or and the

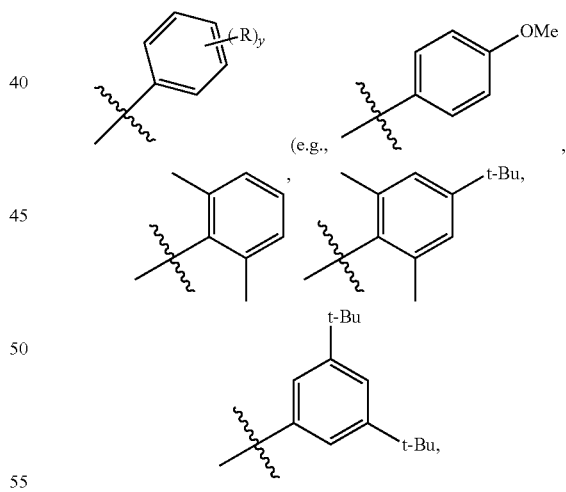

like). R is independently chosen from H, alkoxy groups (e.g., OMe, OEt, $O^iPr$, and the like), alkyl groups (e.g., Me, $^tBu$, Cl, F, $CF_3$, $^iPr$, Et, and the like), aryl groups (e.g., Ph, ether substituted aryl groups, and the like), halide groups (e.g., Cl, F), amino groups (e.g., secondary and tertiary amines, such as, for example, alkyl amines, aryl amines, and the like), alkenyl groups, alkynyl groups, acyl groups (e.g., acetyl groups and the like, nitro groups, nitrile groups, thioether groups, and the like and y is 1, 2, 3, 4, or 5; S is a solvent (e.g., THF, DBE-5, and the like); and p is 1 or 2.

In various examples, Z is

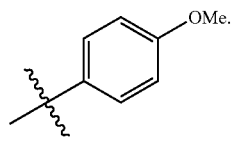 [SMILES: *c1ccc(OC)cc1]

In various examples, the catalyst has the following structure:

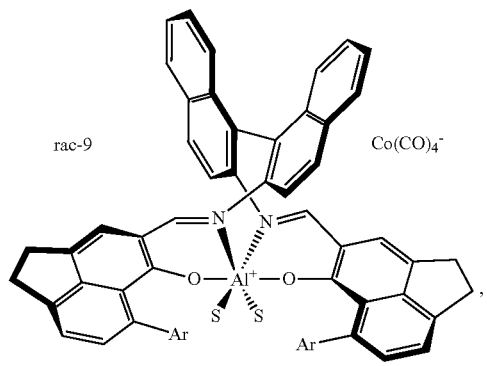

where Ar is

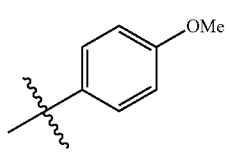 [SMILES: *c1ccc(OC)cc1]

and S is DBE-5.

In an aspect, the present disclosure provides methods of producing a catalyst of the present disclosure. In various examples, a catalyst is made by a method of the present disclosure.

A method of producing a catalyst may comprise: providing a reaction mixture of a catalyst precursor and a cobalt source (e.g., a cobalt carbonyl compound) in a solvent (e.g., DBE-5); and holding the reaction mixture for a selected period of time and/or temperature, where a catalyst of the present disclosure is formed. In various examples, the cobalt source is NaCo(CO)$_4$, [PPN][Co(CO)$_4$], or Ph$_3$SiCo(CO)$_4$. The catalyst may be formed in situ (e.g., during a method of producing a carbonyl compound (e.g., an α,α-disubstituted β-lactone) (a "one-pot" reaction).

A catalyst precursor may have the following structure:

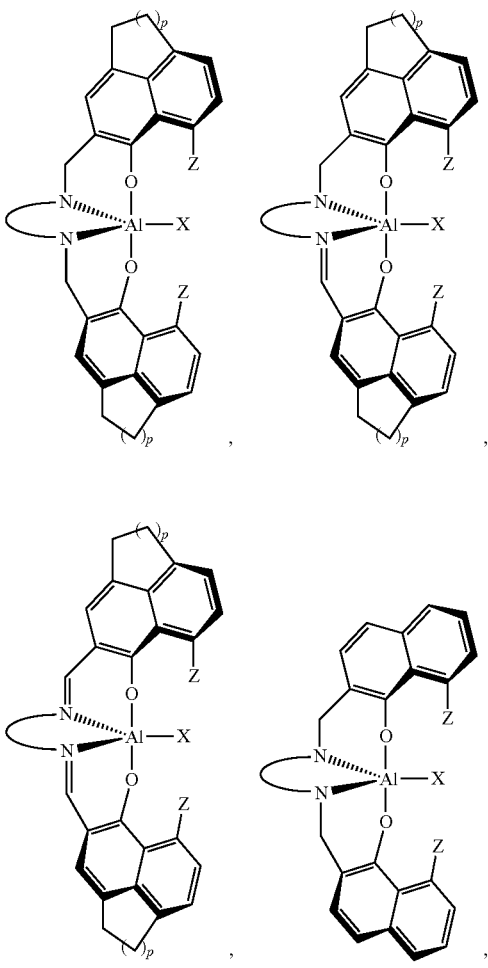

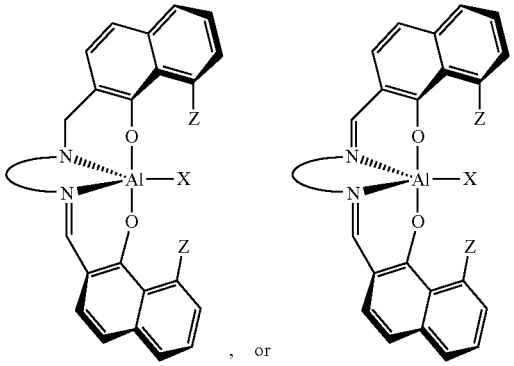

where Z, the diamine bridge, and p are as defined herein, and X is a halide (e.g., chloride or bromide) or an alkyl group, such as, for example, a linear alkyl group (e.g., methyl, ethyl, propyl, butyl, or pentyl).

In an aspect, the present disclosure provides carbonyl compounds (e.g., α,α-disubstituted β-lactones). The carbonyl compounds (e.g., α,α-disubstituted β-lactones) may be produced by a method of the present disclosure.

For example, the carbonyl compound (e.g., α,α-disubstituted β-lactone) has the following structure:

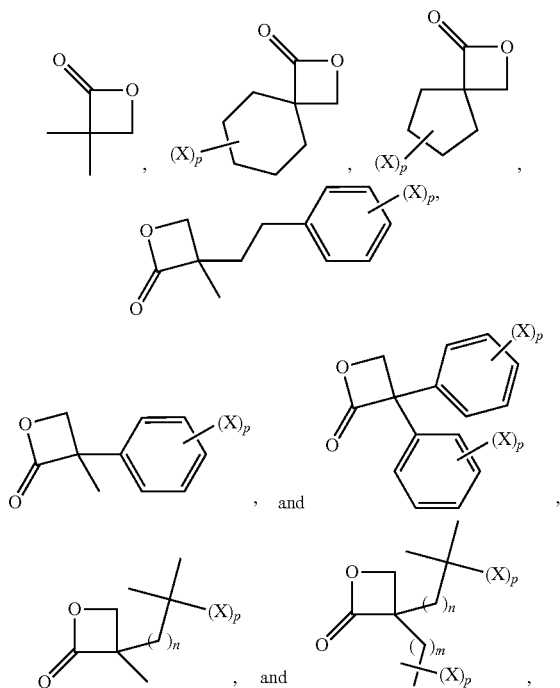

where each X at each occurrence is independently chosen from H, alkoxy groups (e.g., OMe, OEt, O^iPr, and the like), alkyl groups (e.g., Me, ^tBu, Cl, F, CF_3, ^iPr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like, each p independently is 0-10 (1, 2, 3, 4, 5, 6, 7, 8, 9, or 10), n is 0-11 (1, 2, 3, 4, 5, 6, 7, 8, 9, 10, or 11), and m is 0-11 (1, 2, 3, 4, 5, 6, 7, 8, 9, 10, or 11). In various examples, the carbonyl compound (e.g., α,α-disubstituted β-lactone) is chosen from:

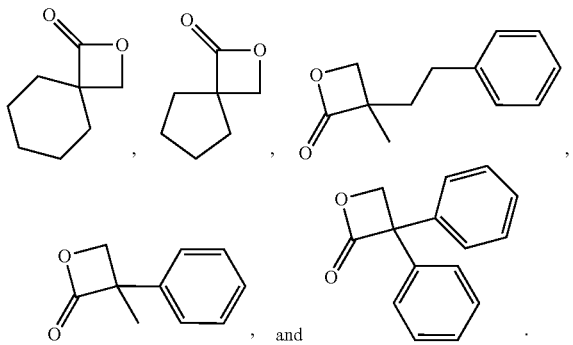

In an aspect, the present disclosure provides polymers. The polymers may be copolymers and/or homopolymers. The polymers may be produced from α,α-disubstituted β-lactones, which may be produced by methods of the present disclosure.

In various examples, at least one of the α substituents is not methyl. As an illustrative example, some of the α substituents are methyl, but not all of the α substituents are methyl.

The polymers may be crystalline, amorphous, semicrystalline, or a mixture of domains. The polymers may be random copolymers and at least one or more other comonomers are lactones. The polymer may be a block copolymer.

A polymer (e.g., copolymer or homopolymer) may comprise (e.g., have) the following group:

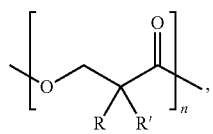

where R and R' are independently at each occurrence in the polymer substituted or unsubstituted alkyl groups, where R and R' are the same or different, or R and R' are connected such that they form a substituted or unsubstituted carbocycle or substituted or unsubstituted heterocycle. n is 100 to 1,000,000, including every integer value and range therebetween, with the proviso that R and R' are not methyl in every occurrence of the polymer. In various examples, all of the R and R' groups are the same. In various other examples, one or more of the R and R' groups are different from the other R and R' groups. In various examples, the polymer comprises two end groups that are the same or different. In various examples, $M_n$ is 10,000 to 100,000,000 g/mol, including every 0.1 g/mol value and ranger therebetween (e.g., 50,000 to 150,000 g/mol, 10,000 to 500,000 g/mol, 10,000 to 1,000,000 g/mol, or 50,000 to 500,000 g/mol) and/or the PDI is 1 to 100, including every PDI value and range therebetween (e.g., 1-20, 1-4, or 1-2.5).

In various examples, a polymer comprises the following group:

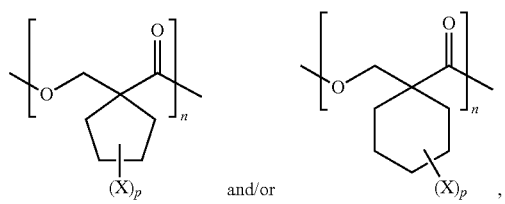

where X at each occurrence is independently chosen from H, alkoxy groups (e.g., OMe, OEt, O^iPr, and the like), alkyl groups (e.g., Me, ^tBu, Cl, F, CF_3, ^iPr, Et, and the like), aryl groups (e.g., Ph, ether substituted aryl, and the like), halide groups (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-8 (1, 2, 3, 4, 5, 6, 7, or 8). In various examples, a polymer comprises the following group:

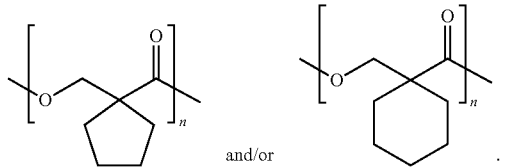

In various examples, a polymer has the following structure:

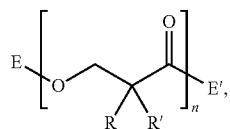

where R and R' are independently at each occurrence in the polymer substituted or unsubstituted alkyl groups, where R and R' are the same or different, or R and R' are connected such that they form a substituted or unsubstituted carbocycle or heterocycle, E and E' are end groups, and n is 100 to 1,000,000, with the proviso that R and R' are not methyl in every occurrence of the polymer. In various examples, all of the R and R' groups are the same. In various other examples, one or more of the R and R' groups are different from the other R and R' groups. In various examples, $M_n$ is 10,000 to 100,000,000 g/mol, including every 0.1 g/mol value and ranger therebetween (e.g., 50,000 to 150,000 g/mol, 10,000 to 500,000 g/mol, 10,000 to 1,000,000 g/mol, or 50,000 to 500,000 g/mol) and/or the PDI is 1 to 100, including every PDI value and range therebetween (e.g., 1-20, 1-4, or 1-2.5).

In various examples, a polymer comprises the following group:

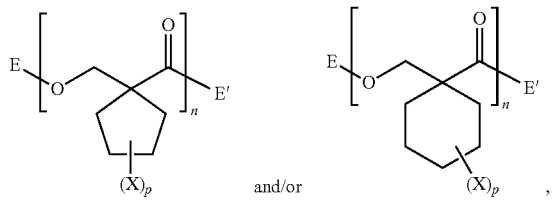

where each X at each occurrence is independently chosen from H, alkoxy groups (e.g., OMe, OEt, O$^i$Pr, and the like), alkyl groups (e.g., Me, $^t$Bu, Cl, F, CF$_3$, $^i$Pr, Et, and the like), aryl groups (e.g., Ph, ether substituted aryl, and the like), halide groups (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-8 (1, 2, 3, 4, 5, 6, 7, or 8). In various examples, a polymer comprises the following group:

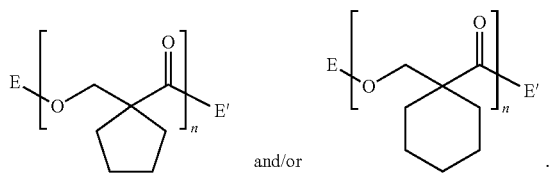

E may be chosen from alkyl groups (e.g., $^i$Pr and the like), aryl groups, and acyl groups. E' may be OH or an alkoxy group.

In an aspect, the present disclosure provides methods of making polymers (e.g., copolymers and/or homopolymers produced from α,α-disubstituted β-lactones produced by methods of the present disclosure).

A method of making a polymer may comprise: producing a carbonyl compound by providing a reaction mixture comprising a 2,2-disubstituted epoxide, a catalyst (e.g., a catalyst of the present disclosure) in a vessel (e.g., a sealed vessel), optionally, with a solvent or two or more solvents (e.g., a polar, aprotic solvent or two or more polar, aprotic solvents); contacting (e.g., pressurizing, sparging, or a combination thereof) the reaction mixture with carbon monoxide; and holding the reaction mixture for a selected time (1 minute (m or min) to 96 hour (h or hr)) and/or temperature (−50 to 200° C. (e.g., 18 to 25° C., such as, for example, 24° C.)), where the carbonyl compound (e.g., an α,α-disubstituted carbonyl compound) is produced; and polymerizing (e.g., polymerizing via anionic ring-opening polymerization, which may be initiated by, for example, phosphines, amines, or metal salts (such as, for example, metal alkoxides or carboxylates) and propagate via a carboxylate chain end) the carbonyl compound; where the polymer is produced.

The method of producing polymers may comprise a step where at least some or all of a β,β-disubstituted carbonyl compound (e.g., β,β-disubstituted β-lactone) is removed from the reaction mixture through heating, which induces decarboxylation of the β,β-disubstituted β-lactone to produce isobutylene, which does not react in the polymerization reaction of α,α-disubstituted β-lactones. In various examples, 5% or less, 4% or less, 3% or less, 2% or less, 1% or less, or 0.5% or less of β,β-disubstituted β-lactone is incorporated into the polymerization of the α,α-disubstituted carbonyl compound.

The steps of the methods described in the various embodiments disclosed herein are sufficient to produce compounds and polymers of the present disclosure. Thus, in an embodiment, a method consists essentially of a combination of the steps of the methods disclosed herein. In another embodiment, a method consists of such steps.

The following Statements are meant to illustrate the present disclosure.

Statement 1. A method of producing a carbonyl compound (e.g., an α,α-disubstituted carbonyl compound), comprising: providing a reaction mixture comprising a 2,2-disubstituted epoxide, a catalyst (e.g., a catalyst of the present disclosure) in a vessel (e.g., a sealed vessel), optionally, with a solvent or two or more solvents (e.g., a polar, aprotic solvent or two or more polar, aprotic solvents); contacting (e.g., pressurizing, sparging, or a combination thereof) the reaction mixture with carbon monoxide; and holding the reaction mixture (e.g., stirring the reaction mixture) for a selected time (1 minute (m or min) to 96 hour (h or hr)) and/or temperature (−50 to 200° C. (e.g., 18 to 25° C., such as, for example, 24° C.)) where the carbonyl compound (e.g., an α,α-disubstituted carbonyl compound) is produced.

Statement 2. A method according to Statement 1, where the reaction mixture is vented.

Statement 3. A method according to Statement 1 or Statement 2, where the carbonyl compound is isolated.

Statement 4. A method according to any one of Statements 1-4, where the catalyst is formed in situ (e.g., from a reaction with a catalytic precursor and a metal source, such as, for example, a cobalt metal source, such as, for example, NaCo(CO)$_4$).

Statement 5. A method according to any one of the preceding Statements, where the catalyst is present in the reaction mixture at a concentration of 0.01 to 10 mol % (e.g., 0.05 to 10 mol %, 1 mol %).

Statement 6. A method according to any one of the preceding Statements, where the solvents are chosen from THF, 1,3-dioxane, 1,4-dioxane, diethyl ether, toluene, dibasic ester (e.g., DBE-1, DBE-2, DBE-3, DBE-4, DBE-5, DBE-6, DBE-7, DBE-8, DBE-9, DBE-10, or the like), $^{i}Pr_2O$, ethyl acetate, and the like, and combinations thereof.

Statement 7. A method according to any one of the preceding Statements, where the solvent is THF.

Statement 8. A method according to any one of Statements 1-6, where the two or more solvents is THF and 1,4-dioxane.

Statement 9. A method according to Statement 8, where the ratio of 1,4-dioxane to THF is 3:1 to 1:3, including every 0.1 ratio value and range therebetween (e.g., 3:1 or 1:1 1,4-dioxane to THF).

Statement 10. A method according to Statement 6, where the solvent is DBE-5.

Statement 11. A method according to any one of the preceding Statements, where the solvent present in the reaction mixture is 0.10 to 12 M, including every 0.01 M value and range therebetween (e.g., 0.5 M), with respect to the 2,2-disubstituted epoxide.

Statement 12. A method according to any one of the preceding Statements, where the reaction mixture is pressurized to 0.1 to 2000 psig (e.g., 900 psig) with CO.

Statement 13. A method according to any one of the preceding Statements, where the catalyst comprises a cationic Lewis acid and anionic metal carbonyl. E.g., the cationic Lewis acid has the following formula: [Lewis acid]$^{z+}$ and the anionic metal carbonyl has the following formula $\{[QM(CO)_x]^{w-}\}_y$, where Q is any ligand and is optional, M is a transition metal chosen from transition metals of Groups 4, 5, 6, 7, 8, 9, and 10 of the periodic table of elements (e.g., cobalt), and z is the valence of the Lewis acid and ranges from 1 to 6 (1, 2, 3, 4, 5, or 6), w is the charge of the metal carbonyl and ranges from 1 to 4 (1, 2, 3, or 4), y is a number such that w times y equals z, and x is a number such as to provide a stable anionic metal carbonyl for $\{[QM(CO)_x]^{w-}\}_y$ and ranges from 1 to 9 (1, 2, 3, 4, 5, 6, 7, 8, or 9).

Statement 14. A method according to Statement 13, where Lewis acid has the following formula:

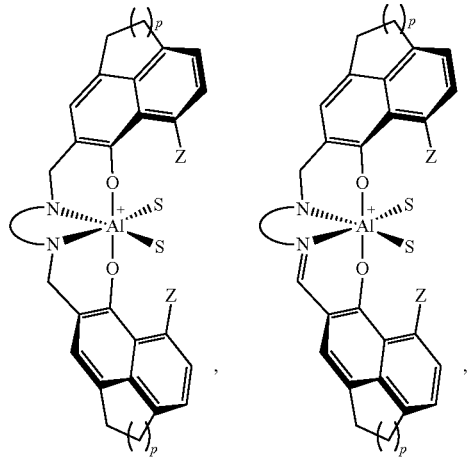

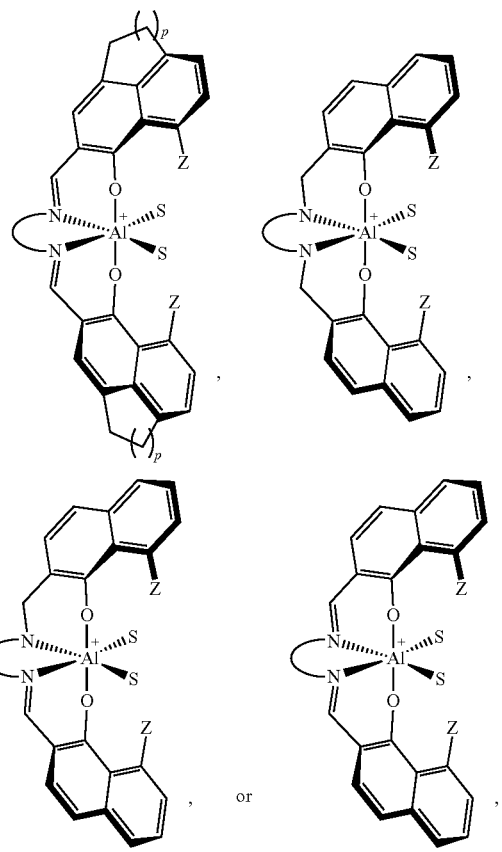

where

(diamine bridge) is chosen from:

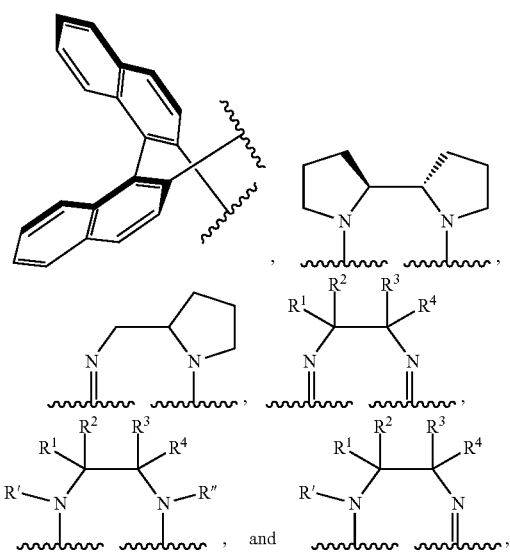

where R', R", R‴, R², R³, and R⁴ are each independently chosen from H, alkyl groups (e.g., Me, ᵗBu, Cl, F, CF₃, ⁱPr, Et, and the like), and aryl groups (e.g., phenyl groups and the like);

Z is H or

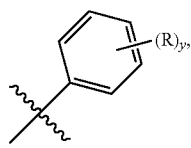

where R is independently chosen from H, alkoxy (e.g., OMe, OEt, OⁱPr, and the like), alkyl (e.g., Me, ᵗBu, Cl, F, CF₃, ⁱPr, Et, and the like), aryl groups (e.g., phenyl groups, ether substituted aryl groups, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and y is 1, 2, 3, 4, or 5; S is a solvent (e.g., THF, DBE-5, and the like); and p is 1 or 2.

Statement 15. A method according to Statement 14, where Z is chosen from:

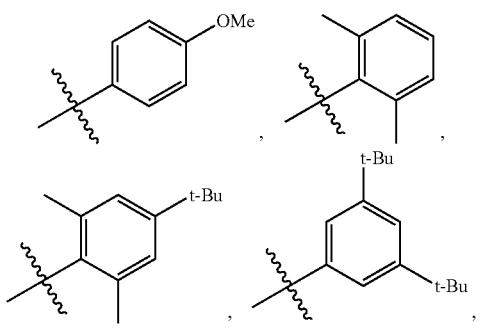

and the like.

Statement 16. A method according to Statement 14 or Statement 15, where Z is

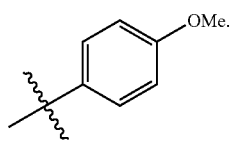 [SMILES: *c1ccc(OC)cc1]

Statement 17. A method according to any one of the preceding Statements, where the method is carried out in a single vessel (e.g., without separating or isolating various possible intermediates, which may be referred to as a "one-pot reaction").

Statement 18. A method according to any one of the preceding Statements, where the 2,2-disubstituted epoxide has the following structure:

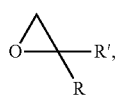

where R and R' is independently a substituted or unsubstituted alkyl group that is the same or different or R and R' are connected such that they form a substituted or unsubstituted carbocycle or substituted or unsubstituted heterocycle.

Statement 19. A method according to Statement 18, where the 2,2-disubstituted epoxide is spirocyclic.

Statement 20. A method according to Statement 19, where the non-epoxide ring of the spirocycle is a $C_3$ to $C_{12}$ ring.

Statement 21. A method according to Statement 20, where the $C_3$ to $C_{12}$ ring is chosen from substituted or unsubstituted cyclopropanes, substituted or unsubstituted cyclobutanes, substituted or unsubstituted cyclopentanes, substituted or unsubstituted cyclohexanes, substituted or unsubstituted cycloheptanes, substituted or unsubstituted cyclooctanes, substituted or unsubstituted cyclononanes, substituted or unsubstituted cyclodecanes, substituted or unsubstituted cycloundecanes, and substituted or unsubstituted cyclododecanes.

Statement 22. A method according to any one of Statements 18-21, where the substituted or unsubstituted alkyl groups are linear or branching alkyl groups or cyclic alkyl groups.

Statement 23. A method according to Statement 22, where the linear or branching alkyl groups have a longest linear chain of 1 to 12 carbons (e.g., 1, 2, 3, 4, 5, 6, 7, 8, 9, 10, 11, or 12).

Statement 24. A method according to any one of Statements 18-23, where the 2,2-disubstituted epoxide is chosen from:

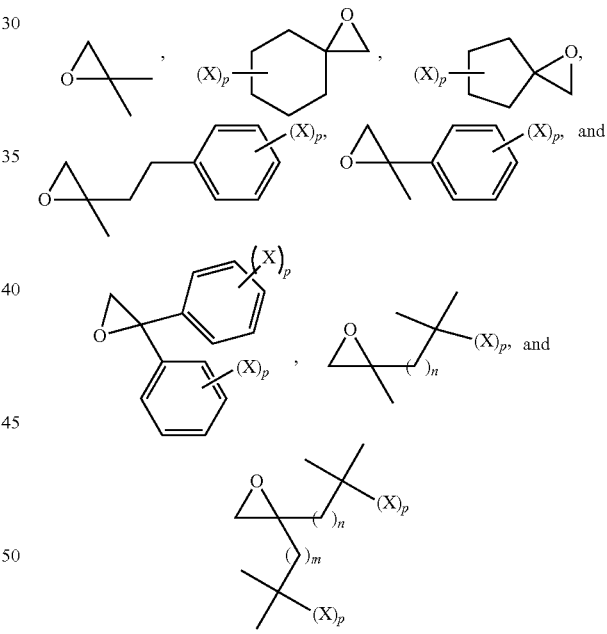

where each X at each occurrence is independently chosen from H, alkoxy (e.g., OMe, OEt, OⁱPr, and the like), alkyl (e.g., Me, ᵗBu, Cl, F, CF₃, ⁱPr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like, each p independently is 0-10 (1, 2, 3, 4, 5, 6, 7, 8, 9, or 10), n is 0-11 (1, 2, 3, 4, 5, 6, 7, 8, 9, 10, or 11), and m is 0-11 (1, 2, 3, 4, 5, 6, 7, 8, 9, 10, or 11).

Statement 25. A method according to any one of Statements 18-24, where the 2,2-disubstituted epoxide is chosen from:

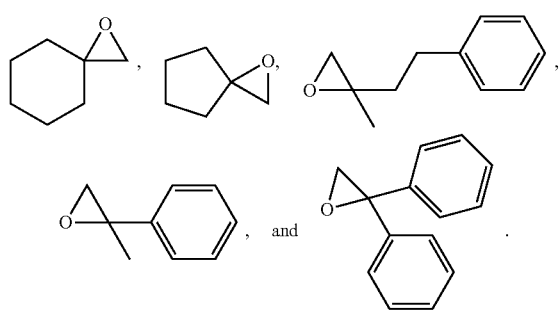

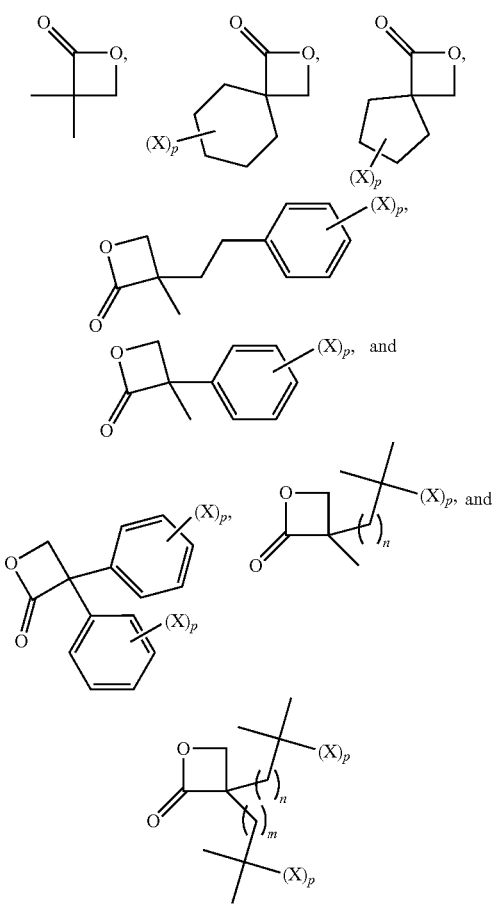

Statement 26. A method according to any one of the preceding Statements, where the carbonyl compound is the result of a carbonylation at the more substituted position on the 2,2-disubstituted epoxide.

Statement 27. A method according to any one of the preceding Statements, where the carbonyl compound is an α,α-disubstituted lactone.

Statement 28. A method according to Statement 26 or Statement 27, where the carbonyl compound is chosen from:

where each X at each occurrence is independently chosen from H, alkoxy (e.g., OMe, OEt, O$^i$Pr, and the like), alkyl (e.g., Me, $^t$Bu, Cl, F, CF$_3$, $^i$Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like, each p independently is 0-10 (1, 2, 3, 4, 5, 6, 7, 8, 9, or 10), n is 0-11 (1, 2, 3, 4, 5, 6, 7, 8, 9, 10, or 11), and m is 0-11 (1, 2, 3, 4, 5, 6, 7, 8, 9, 10, or 11).

Statement 29. A method according to any one of Statements 26-28, where the carbonyl compound is chosen from:

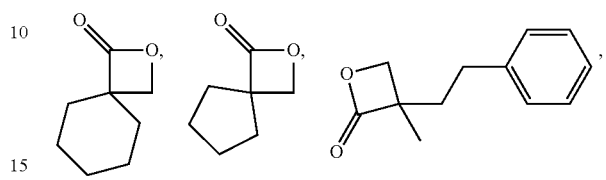

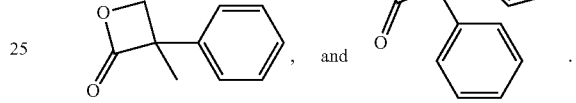

Statement 30. A catalyst comprising a cationic Lewis acid and anionic metal carbonyl. E.g., the cationic Lewis acid has the following formula: [Lewis acid]$^{z+}$ and the anionic metal carbonyl has the following formula $\{[QM(CO)_x]^{w-}\}_y$, where Q is any ligand and is optional, M is a transition metal chosen from transition metals of Groups 4, 5, 6, 7, 8, 9, and 10 of the periodic table of elements (e.g., cobalt), z is the valence of the Lewis acid and ranges from 1 to 6 (1, 2, 3, 4, 5, or 6), w is the charge of the metal carbonyl and ranges from 1 to 4 (1, 2, 3, or 4), y is a number such that w times y equals z, and x is a number such as to provide a stable anionic metal carbonyl for $\{[QM(CO)_x]^{w-}\}y$ and ranges from 1 to 9 (1, 2, 3, 4, 5, 6, 7, 8, or 9).

Statement 31. A catalyst according to Statement 30, comprising:

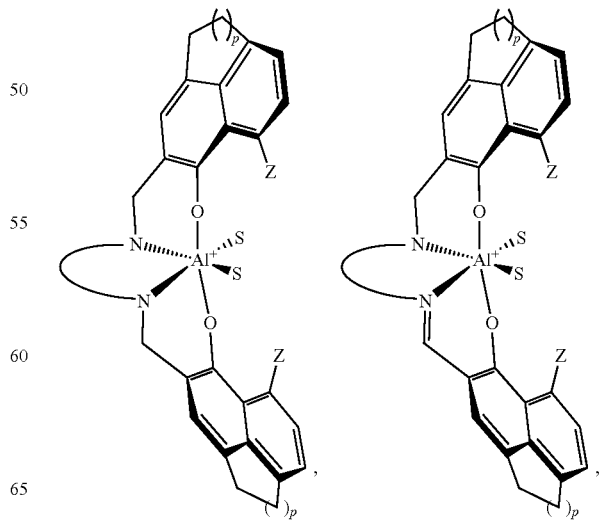

-continued

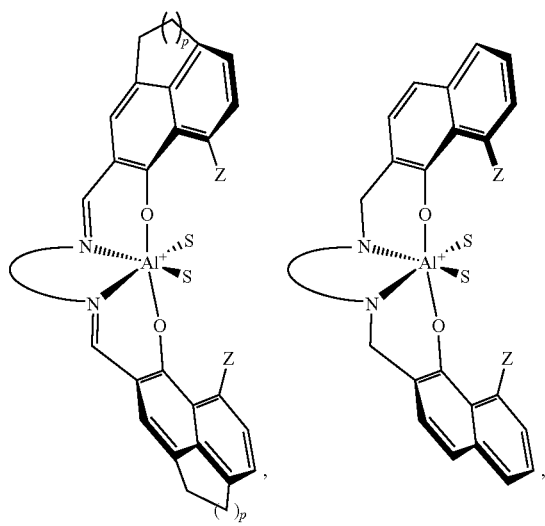
,

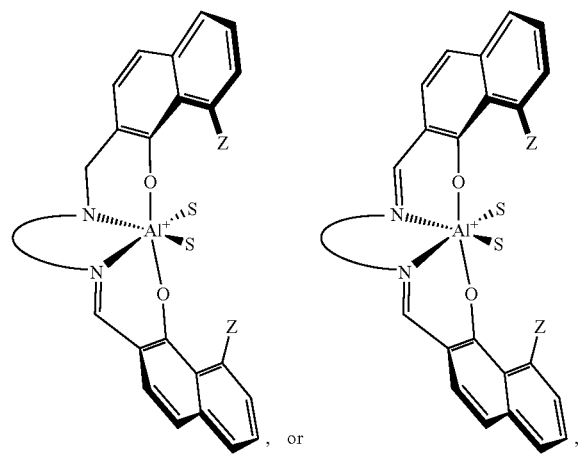
, or where

(diamine bridge) is chosen from

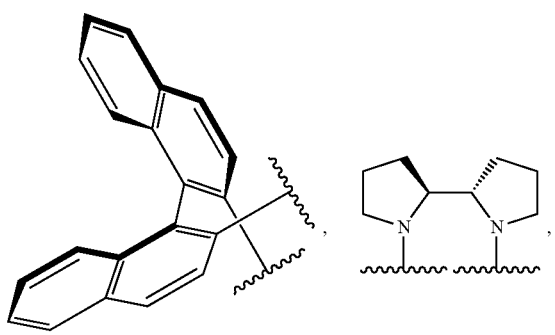

-continued

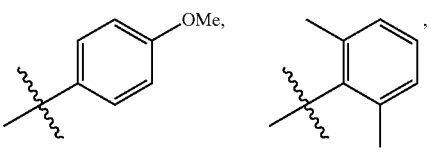

where R', R", R', R², R³, and R⁴ are each independently chosen from H, alkyl groups (e.g., Me, $^t$Bu, Cl, F, CF$_3$, $^i$Pr, Et, and the like), and aryl groups (e.g., phenyl groups and the like);

Z is H or

where R is independently chosen from H, alkoxy (e.g., OMe, OEt, O$^i$Pr, and the like), alkyl (e.g., Me, $^t$Bu, Cl, F, CF$_3$, $^i$Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and y is 1, 2, 3, 4, or 5; S is a solvent (e.g., THF, DBE-5, and the like); and p is 1 or 2.

Statement 32. A catalyst according to Statement 31, where Z is chosen from:

and the like.

Statement 33. A catalyst according to Statement 31 or Statement 32, where Z is

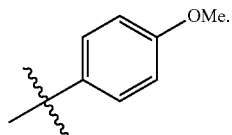 [SMILES: *c1ccc(OC)cc1]

Statement 34. A catalyst according to any one of Statements 30-33, further comprising tetraphenyl borate.

Statement 35. A method of making a catalyst according to Statement 30, comprising: providing a reaction mixture of a catalyst precursor (e.g.,

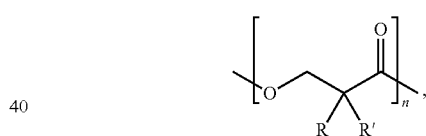

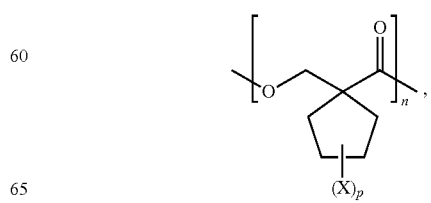

-continued

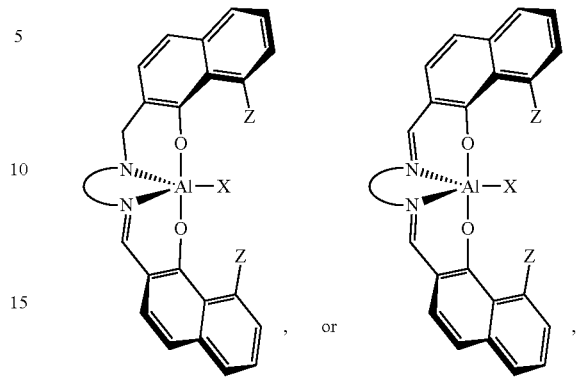

where Z, the diamine bridge, and p are as defined herein and X is a halide (e.g., chloride or bromide) or an alkyl group, such as, for example, a linear alkyl group (e.g., methyl, ethyl, propyl, butyl, or pentyl) and a cobalt source (e.g., a cobalt carbonyl compound) in a solvent (e.g., DBE-5); and holding the reaction mixture for a selected period of time and/or temperature, where the catalyst according to Statement 31 is formed.

Statement 36. A method according to Statement 35, where the cobalt source is $NaCo(CO)_4$, $[PPN][Co(CO)_4]$, or $Ph_3SiCo(CO)_4$.

Statement 37. A method according to Statement 35 or Statement 36, where the method occurs in situ.

Statement 38. A polymer (e.g., copolymer or homopolymer) having the following group:

$$\left[O\underset{R\ R'}{\overset{O}{\diagup}}\right]_n,$$

where R and R' are independently at each occurrence in the polymer substituted or unsubstituted alkyl groups, where R and R' are the same or different, or R and R' are connected such that they form a substituted or unsubstituted carbocycle or heterocycle, and n is 100 to 1,000,000, with the proviso that R and R' are not methyl in every occurrence of the polymer. E.g., all of the R and R' groups are the same. E.g., one or more of the R and R' groups are different from the other R and R' groups.

Statement 39. A polymer according to Statement 38, where the polymer comprises two end groups that are the same or different.

Statement 40. A polymer according to Statement 38 or Statement 39, comprising the following group:

$$\left[O\underset{(X)_p}{\diagup}\right]_n,$$

where X at each occurrence is independently chosen from H, alkoxy (e.g., OMe, OEt, O'Pr, and the like), alkyl (e.g., Me, 'Bu, Cl, F, CF₃, 'Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-8 (1, 2, 3, 4, 5, 6, 7, or 8).

Statement 41. A polymer according to Statement 38-40, where the polymer comprises the following group:

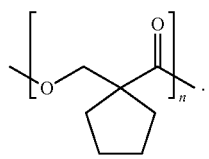

Statement 42. A polymer according to Statement 38 or Statement 39, comprising the following group:

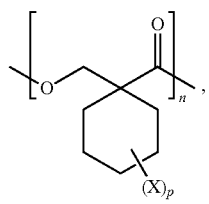

where X at each occurrence is independently chosen from H, alkoxy (e.g., OMe, OEt, O'Pr, and the like), alkyl (e.g., Me, 'Bu, Cl, F, CF₃, 'Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-10 (1, 2, 3, 4, 5, 6, 7, 8, 9, or 10).

Statement 43. A polymer according to Statement 38, Statement 39, or Statement 42, where the polymer comprises the following group:

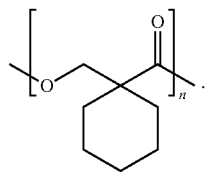

Statement 44. A polymer according to any one of Statements 38-43, where the $M_n$ is 10,000 to 100,000,000 g/mol, including every 0.1 g/mol value and ranger therebetween (e.g., 50,000 to 150,000 g/mol, 10,000 to 500,000 g/mol, 10,000 to 1,000,000 g/mol, or 50,000 to 500,000 g/mol).

Statement 45. A polymer according to any one of Statements 38-44, where the PDI is 1 to 100, including every PDI value and range therebetween (e.g., 1-20, 1-4, or 1-2.5).

Statement 46. A polymer according to any one of Statements 38-45, where the polymer is a random copolymer and at least one or more other comonomers are lactones.

Statement 47. A polymer according to any one of Statements 38-46, where the polymer is a block copolymer.

Statement 48. A polymer according to any one of Statements 38-45 or 47, where the polymer is a block copolymer and at least one or more other comonomers are lactones.

Statement 49. A polymer according to Statement 38 having the following structure:

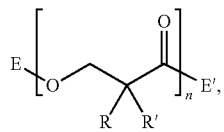

where R and R' are independently at each occurrence in the polymer substituted or unsubstituted alkyl groups, where R and R' are the same or different, or R and R' are connected such that they form a substituted or unsubstituted carbocycle or heterocycle, and n is 100 to 1,000,000, with the proviso that R and R' are not methyl in every occurrence of the polymer. E.g., all of the R and R' groups are the same. E.g., one or more of the R and R' groups are different from the other R and R' groups.

Statement 50. A polymer according to Statement 49, where the polymer comprises two end groups that are the same or different.

Statement 51. A polymer according to Statement 49 or Statement 50, having the following structure:

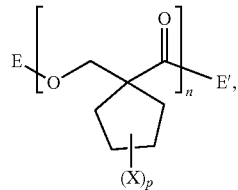

where X at each occurrence is independently chosen from H, alkoxy (e.g., OMe, OEt, O'Pr, and the like), alkyl (e.g., Me, 'Bu, Cl, F, CF₃, 'Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-8 (1, 2, 3, 4, 5, 6, 7, or 8).

Statement 52. A polymer according to any one of Statements 49-51, having the following structure:

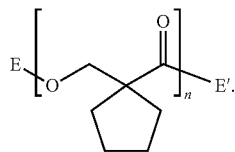

Statement 53. A polymer according to Statement 49 or Statement 50, having the following structure:

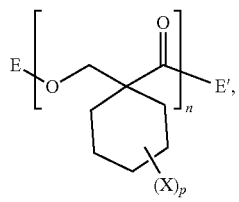

where X at each occurrence is independently chosen from H, alkoxy (e.g., OMe, OEt, O$^i$Pr, and the like), alkyl (e.g., Me, $^t$Bu, Cl, F, CF$_3$, $^i$Pr, Et, and the like), aryl groups (e.g., Ph, ether substituted aryl, and the like), halides (Cl, F), amino groups (e.g., secondary and tertiary amines, such as, for example, alkyl amines, aryl amines, and the like), alkenyl groups, alkynyl groups, acyl groups, nitro groups, nitrile groups, thioether groups, and the like and p is 0-10 (1, 2, 3, 4, 5, 6, 7, 8, 9, or 10).

Statement 54. A polymer according to Statement 49, Statement 50, or Statement 53, where the polymer has the following structure:

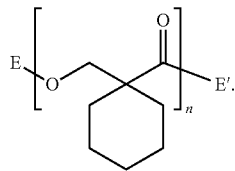

Statement 55. A polymer according to any one of Statements 49-54, where E is chosen from alkyl groups (e.g., $^i$Pr and the like), aryl groups, and acyl groups.

Statement 56. A polymer according to any one of Statements 49-55, where E' is OH or an alkoxy group.

Statement 57. A polymer according to any one of Statements 49-56, where the $M_n$ is 10,000 to 100,000,000 g/mol, including every 0.1 g/mol value and ranger therebetween (e.g., 50,000 to 150,000, 10,000 to 500,000, 10,000 to 1,000,000 g/mol, or 50,000 to 500,000).

Statement 58. A polymer according to any one of Statements 49-57, where the PDI is 1 to 100, including every PDI value and range therebetween (e.g., 1 to 20, 1-4, or 1-2.5).

Statement 59. A polymer according to any one of Statements 38-58, where the polymer is amorphous or semicrystalline.

Statement 60. A method of producing a polymer according to any one of Statements 38-59, comprising: producing a carbonyl compound by providing a reaction mixture comprising a 2,2-disubstituted epoxide, a catalyst (e.g., a catalyst of the present disclosure) in a vessel (e.g., a sealed vessel), optionally, with a solvent or two or more solvents (e.g., a polar, aprotic solvent or two or more polar, aprotic solvents); contacting (e.g., pressurizing, sparging, or a combination thereof) the reaction mixture with carbon monoxide; and holding the reaction mixture for a selected time (1 minute (m or min) to 96 hour (h or hr)) and/or temperature (−50 to 200° C. (e.g., 18 to 25° C., such as, for example, 24° C.)), where the carbonyl compound (e.g., an α,α-disubstituted carbonyl compound) is produced; and polymerizing (e.g., polymerizing via anionic ring-opening polymerization, which may be initiated by, for example, phosphines, amines, or metal salts (such as, for example, metal alkoxides or carboxylates) and propagate via a carboxylate chain end) the carbonyl compound; where the polymer according to any one of Statements 38-59 is produced.

Statement 61. A method according to Statement 60, where the holding the reaction mixture containing the polymerization is performed at a temperature that results in decarboxylation of a β,β-disubstituted carbonyl compound.

Statement 62. A method according to Statement 59 or Statement 61, where 5% or less (e.g., 4% or less, 3% or less, 2% or less, 1% or less, or 0.5% or less) of the β,β-disubstituted carbonyl compound is incorporated into the polymerization of the α,α-disubstituted carbonyl compound.

The following Example is presented to illustrate the present disclosure. This example is not intended to be limiting in any matter.

Example

The following describes methods of the present disclosure.

Poly(pivalolactone) (PPVL) is a crystalline polyester with excellent physical and mechanical properties; however, prohibitively expensive syntheses of pivalolactone have thwarted efforts to produce PPVL on an industrial scale. Described herein are highly regioselective sandwich-type catalysts for the carbonylation of isobutylene oxide. These sterically encumbered complexes install carbon monoxide at the substituted epoxide carbon, generating unprecedented contrasteric selectivity (up to >99:1). Further catalyst development improved catalyst solubility and reproducibility while maintaining high regioselectivity. Additionally, a dibasic ester solvent extended catalyst lifetimes and suppressed side product formation. This contrasteric carbonylation of isobutylene oxide offers a desirable route to sought-after pivalolactone and, therefore, PPVL.

It was hypothesized that this process may be facilitated by the formation of a stable, tertiary carbocation or partial positive charge at the dimethyl substituted carbon which may promote an SN1-type pathway. After epoxide ring-opening, the remainder of the mechanism likely proceeds similarly to previously studied carbonylation systems; the alkyl cobalt species (intermediate A, FIG. 2) undergoes CO insertion to form a cobalt acyl (intermediate B). Next, intramolecular attack by the metal alkoxide produces the β-lactone product and regenerates the active catalyst.

Figure 3:
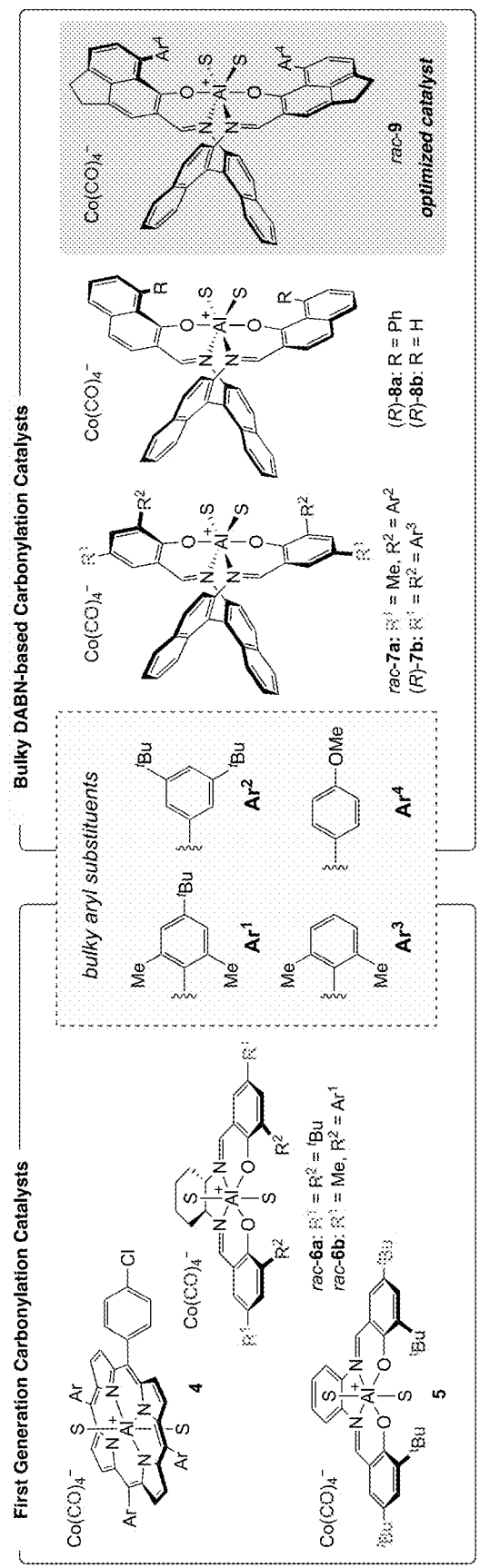
FIG. 3 shows catalysts screened for the contrasteric carbonylation of isobutylene oxide (S=solvent).

A variety of [Lewis acid]$^+$[Co(CO)$_4$]$^-$ catalysts (FIG. 3) were screened for the contrasteric-selective carbonylation of 1 (Table 1). As expected, first generation porphyrin and salen catalysts (4, 5, and rac-6a, Table 1, entries 1-3) resulted in predominantly lactone 3. However, aldehyde (10) and alkene (11) side products were also observed, suggesting a competing epoxide isomerization pathway as well as steric lactone decarboxylation. To improve regioselectivity, previous 2,3-disubstituted epoxide carbonylation and isomerization systems employed catalysts with additional bulk. Therefore, Lewis acids with large aryl groups in the ortho-position of the phenoxide, such as rac-6b, were screened. Although these bulky ligands did increase contrasteric selectivity (42:58 2:3, Table 1, entry 4), 2 remained the minor regioisomer, and isomerization to isobutyraldehyde (10) was the major pathway. Next, catalysts with a 2,2'-diamino-1,1'-binaphthalene (DABN)-based backbone, which forces the ligand out of coplanarity and into a cis-α configuration (FIG. 3), were screened. Although catalyst rac-7a was previously used for the contrasteric carbonylation of cis-epoxides, it still promoted steric regioselectivity using epoxide 1 (8:92 2:3, Table 1, entry 5). However, increasing bulk at the para-position of the catalyst facilitated the contrasteric carbonylation pathway and suppressed isomerization, though production of 3 still dominated (33:67 2:3, catalyst (R)-7b, Table 1, entry 6). It was hypothesized that developing a DABN-based ligand with even more steric hindrance would further enhance contrasteric selectivity.

TABLE 1

Initial Catalyst Screen for the Contrasteric Carbonylation of IBO.

| entry | catalyst | ratio (2:3) | lactone (2 + 3) | % conversion[a] 10 | 11 |
|---|---|---|---|---|---|
| 1 | 4 | 8:92 | 96 | 2 | 2 |
| 2 | 5 | 4:96 | 82 | 3 | 2 |
| 3 | rac-6a | 8:92 | 57 | 8 | 2 |
| 4 | rac-6b | 42:58 | 39 | 59 | 2 |
| 5 | rac-7a[b] | 8:92 | 53 | 8 | 1 |
| 6[c] | (R)-7b[b] | 33:67 | 27 | 19 | <1 |
| 7[c,d] | (R)-8a[b] | >99:1 | 14 | 63 | <1 |
| 8[d] | (R)-8b[b] | 21:79 | 20 | 3 | <1 |
| 9[d] | rac-9[b] | 96:4 | 22 | 70 | <1 |

[a]Determined by $^1$H NMR spectroscopy of the crude reaction mixture.
[b]Catalyst made in situ (L$_n$AlCl + NaCo(CO)$_4$).
[c]An additional ester side product formed via the Tishchenko reaction of two isobutyraldehyde molecules.
[d]Percent conversion determined relative to 1 by $^1$H NMR spectroscopy, excluding unassigned MPVO products, which were filtered out using alumina plugs (vide infra, and see below for additional details).
[e]0.5M 1,4-dioxane/THF (3:1).

To install this additional substitution, the salicylaldimine group was replaced with an 8-aryl-substituted iminonaphthol to form a sandwich-type catalyst ((R)-8a). This modification improved the regioselectivity such that only minimal steric product was observed (>99:1 2:3, Table 1, entry 7). To explore the origin of this unprecedented result, catalyst (R)-8b was prepared using an iminonaphthol-based salicylaldehyde that lacks an additional aryl substituent. This analogue was unable to inhibit steric attack and therefore favored production of 3 (21:79 2:3, Table 1, entry 8), demonstrating the importance of the additional aryl substituents for regiocontrol.

Despite its relative success, (R)-8a still suffered from a number of limitations, such as inconsistencies in both conversion and regioselectivity between catalyst batches. It is hypothesized that these reproducibility problems arose from poor catalyst solubility; attempts were undertaken to improve by using an enantiopure DABN backbone. To overcome this limitation while maintaining high regioselectivity, an acenaphthene-derived salicylaldehyde with p-methoxy substitution on the pendant aryl group (rac-9) was synthesized. The resulting catalyst was soluble under standard reaction conditions and yielded reproducible results between catalyst batches with only a modest decrease in contrasteric selectivity (96:4 2:3, Table 1, entry 9).

Unfortunately, both sandwich catalysts ((R)-8a and rac-9) produced several additional side products, initially limiting the overall utility of this process (FIG. 4). Favoring the SN1-type pathway increased the rate of epoxide isomerization to 10 via Meinwald rearrangement and/or β-hydrogen elimination after cobaltate attack (pathways a and b, respectively, FIG. 4A). Additionally, proton abstraction from an isobutylene oxide methyl group and/or β-hydrogen elimination of A produces β-methallyl alcohol (12) (pathways c and d, respectively, FIG. 4A). Due to the adjacent cis-coordination sites on the catalyst, 10 and 12 undergo a Meerwein-Ponndorf-Verley-Oppenaur (MPVO) reaction, producing methacrolein (13) and isobutyl alcohol (14) as additional side products (FIG. 4B).

Figure 5:
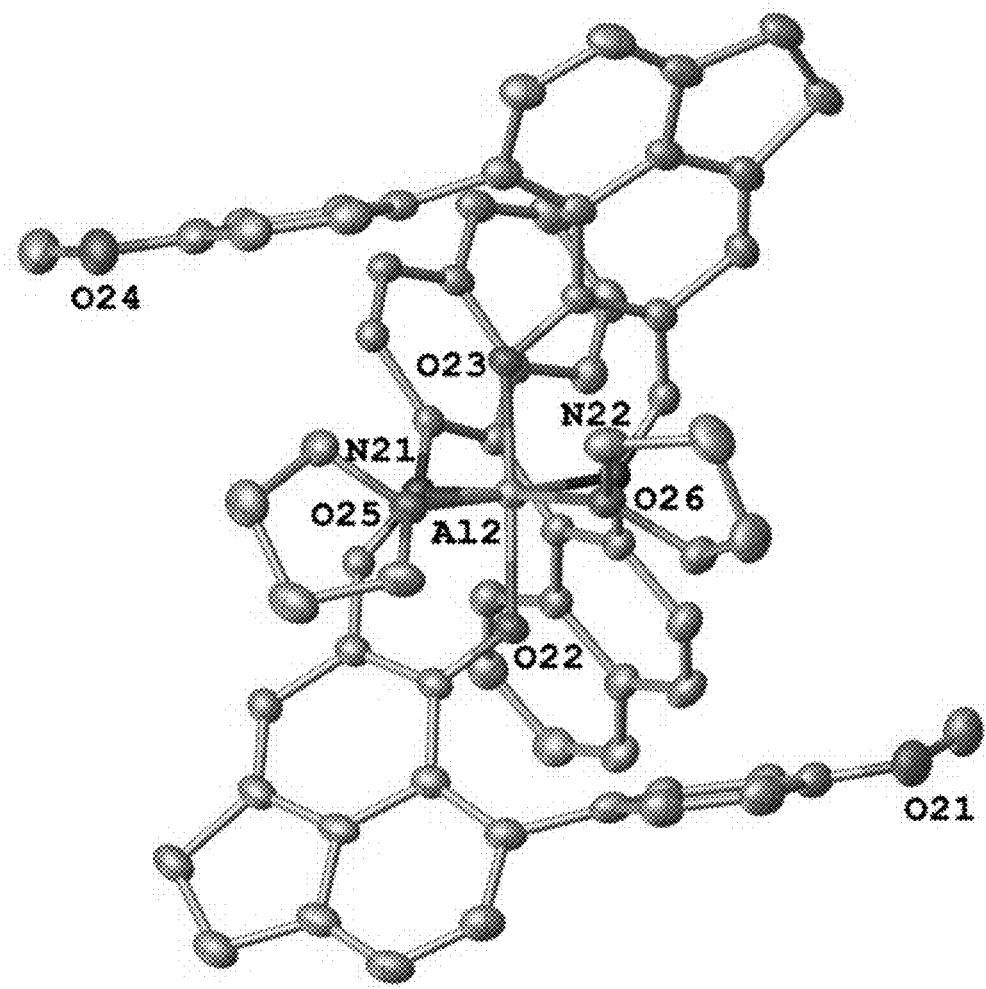
FIG. 5 shows X-ray crystal structure of the rac-9, depicting the restricted catalyst binding pocket. Only one of the two independent molecules is shown; counterions, solvent, and hydrogen atoms are omitted for clarity. Displacement ellipsoids shown at 50% probability.
Figure 6:
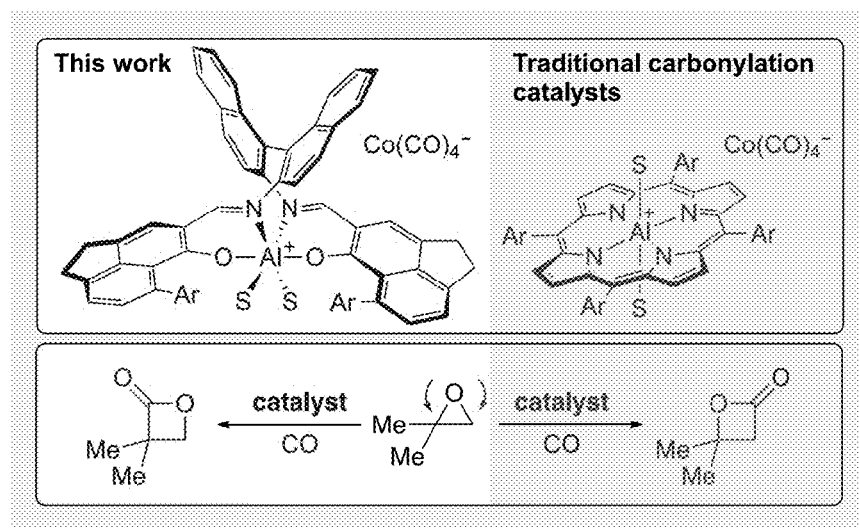
FIG. 6 shows a catalyst and reaction of the present disclosure compared to previous carbonylation catalysts and reactions.
Figure 7:
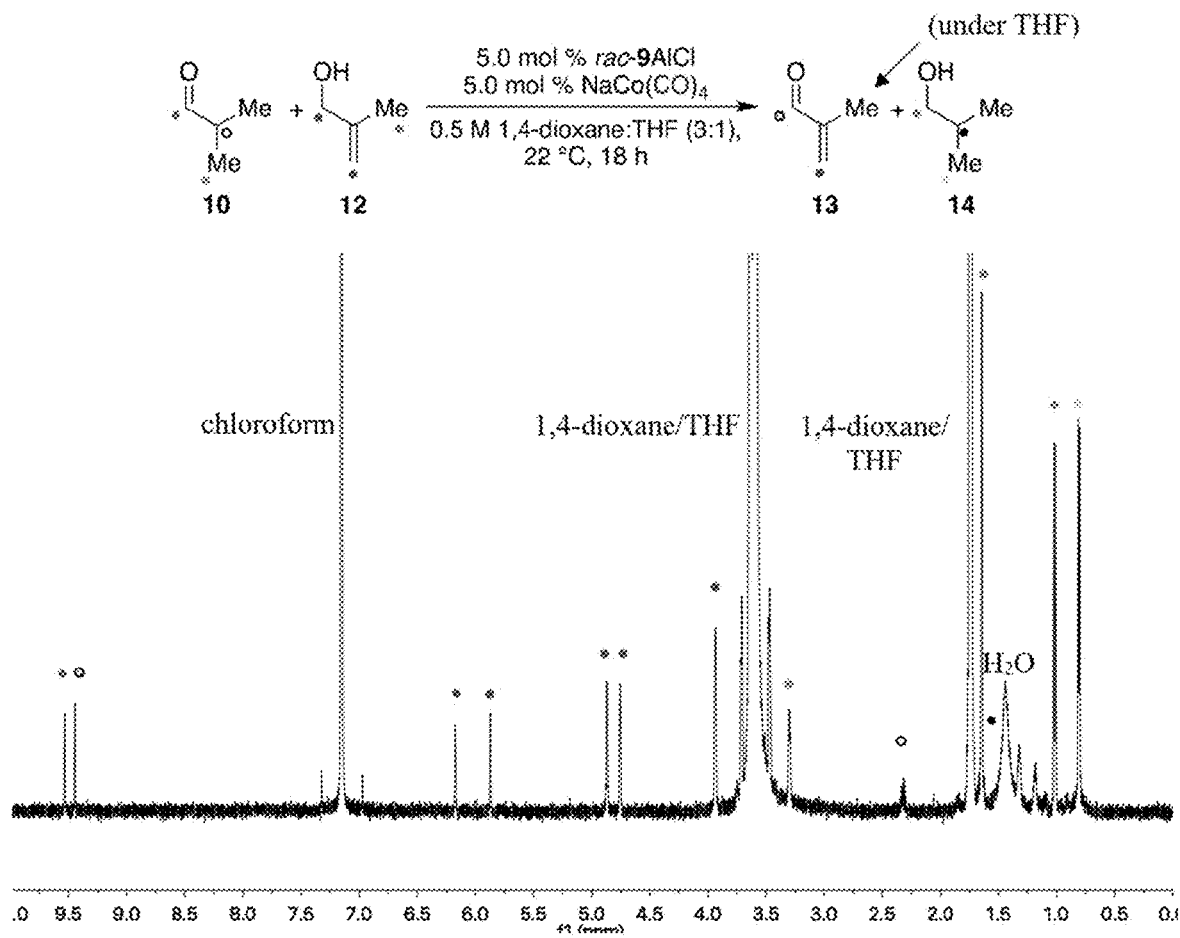
FIG. 7 shows a control MINO reaction and an NMR spectrum of the resulting product mixture.
Figure 8:
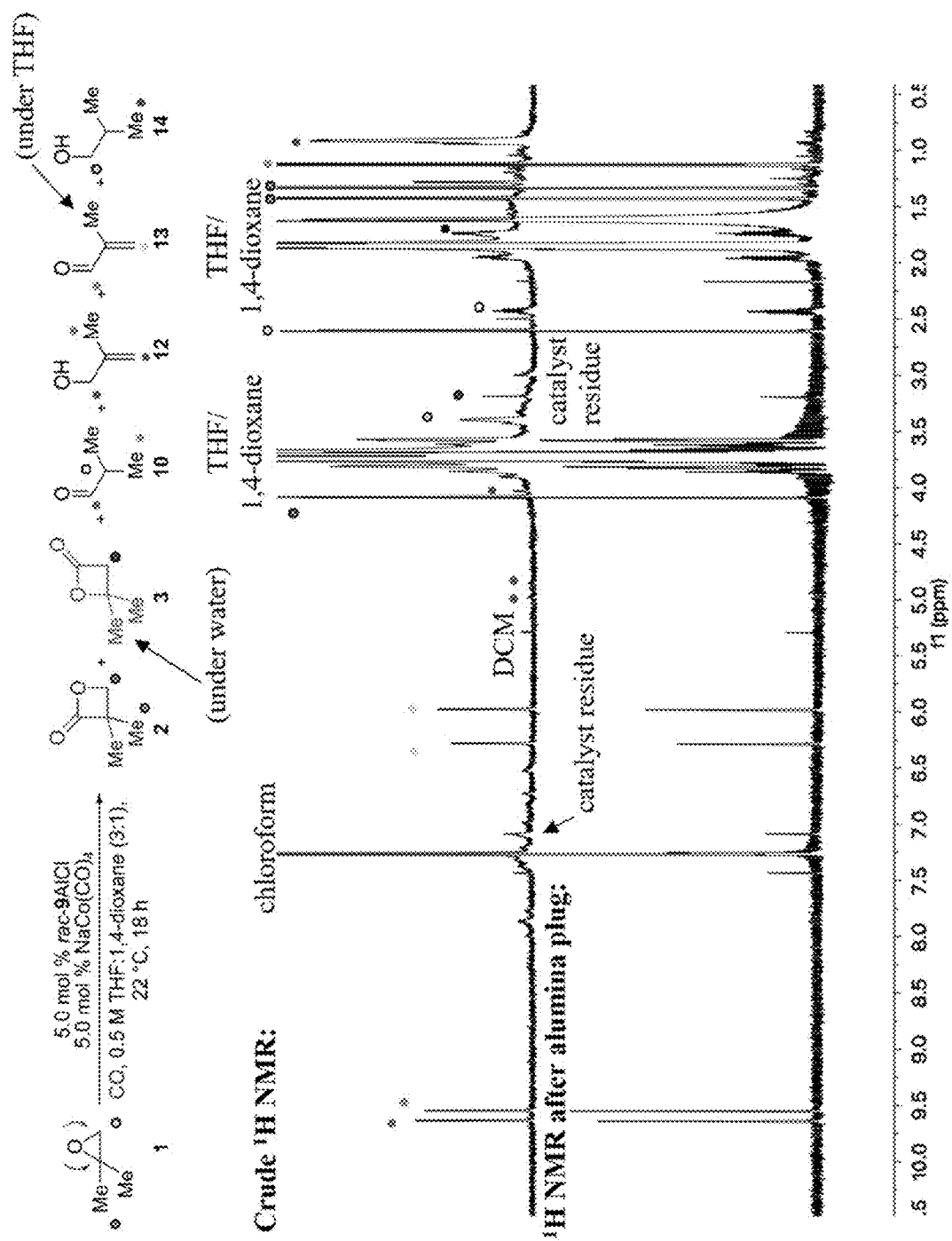
FIG. 8 shows the reaction scheme and resulting NMR spectra of the crude product mixture and chromatographed product mixture.
Figure 10:
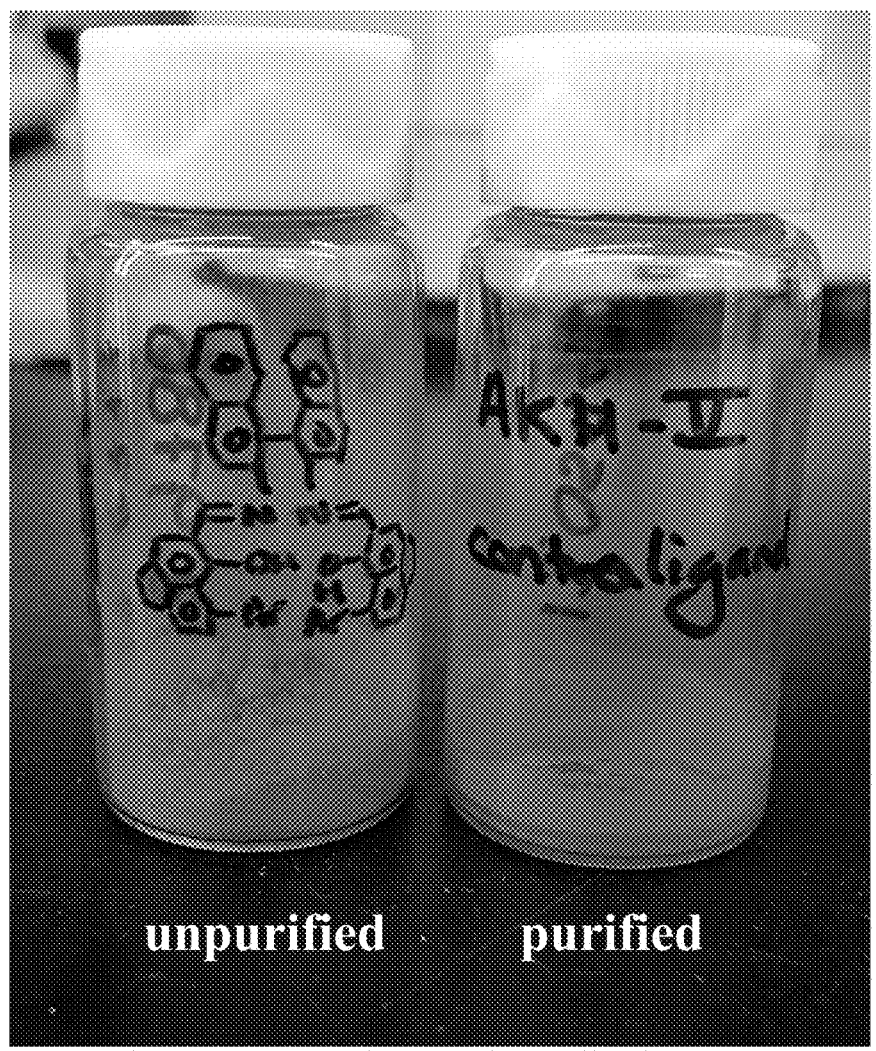
FIG. 10 shows the correct color of the purified ligand S19 (rac-4,4'-((1E,1'E)-([1,1'-binaphthalene]-2,2'-diylbis(azaneylylidene))bis(methaneylylidene))bis(6-(4-methoxyphenyl)-1,2-dihydroacenaphthylen-5-ol)) next to the imine hydrolyzed ligand.
Figure 11:
FIG. 11 shows the correct color of the purified catalyst rac-9AlCl.
Figure 12:
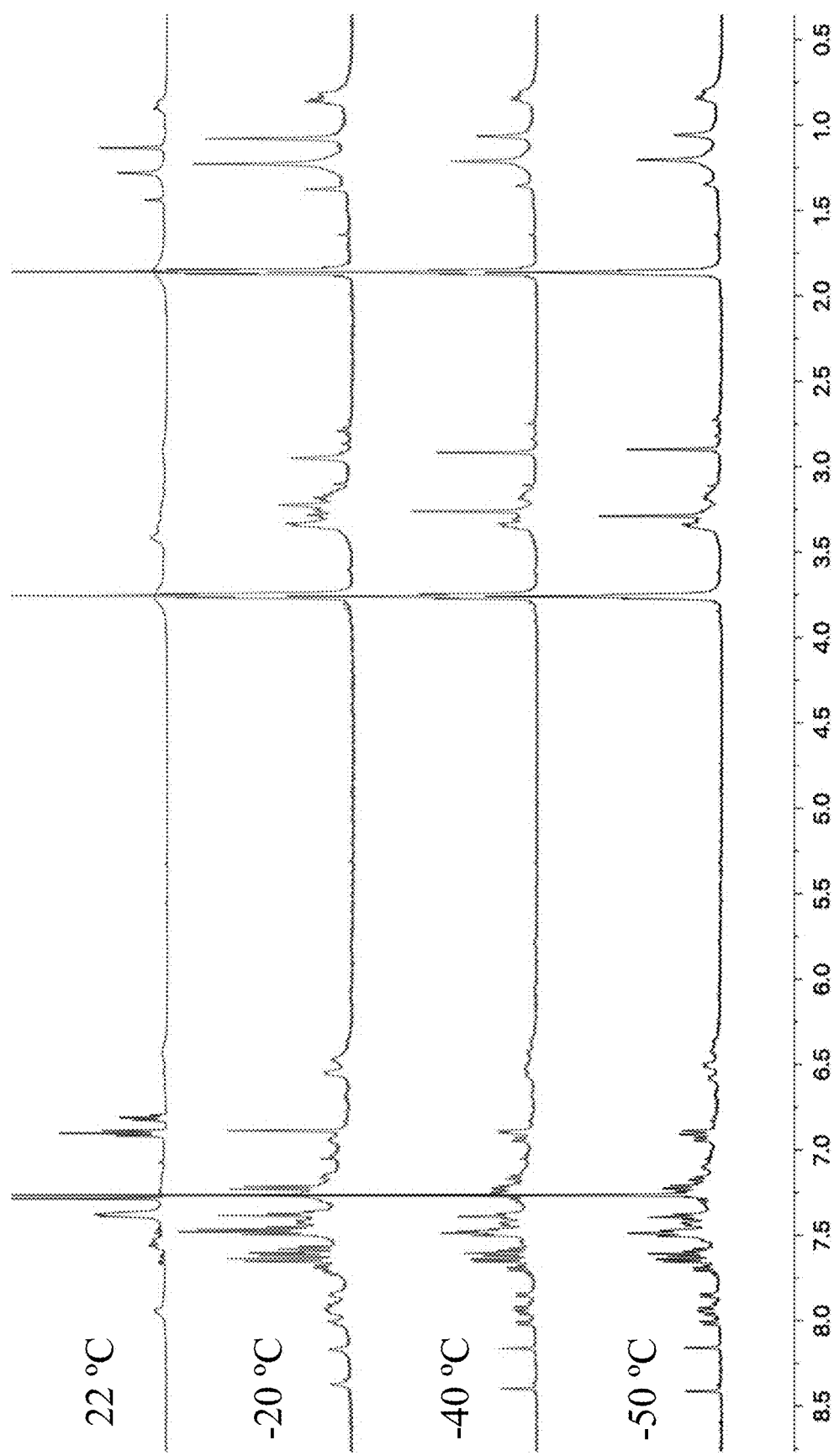
FIG. 12 shows the $^1$H NMR spectra of [rac-9Al(THF)$_2$][BPh$_4$] at various temperatures.
Figure 13:
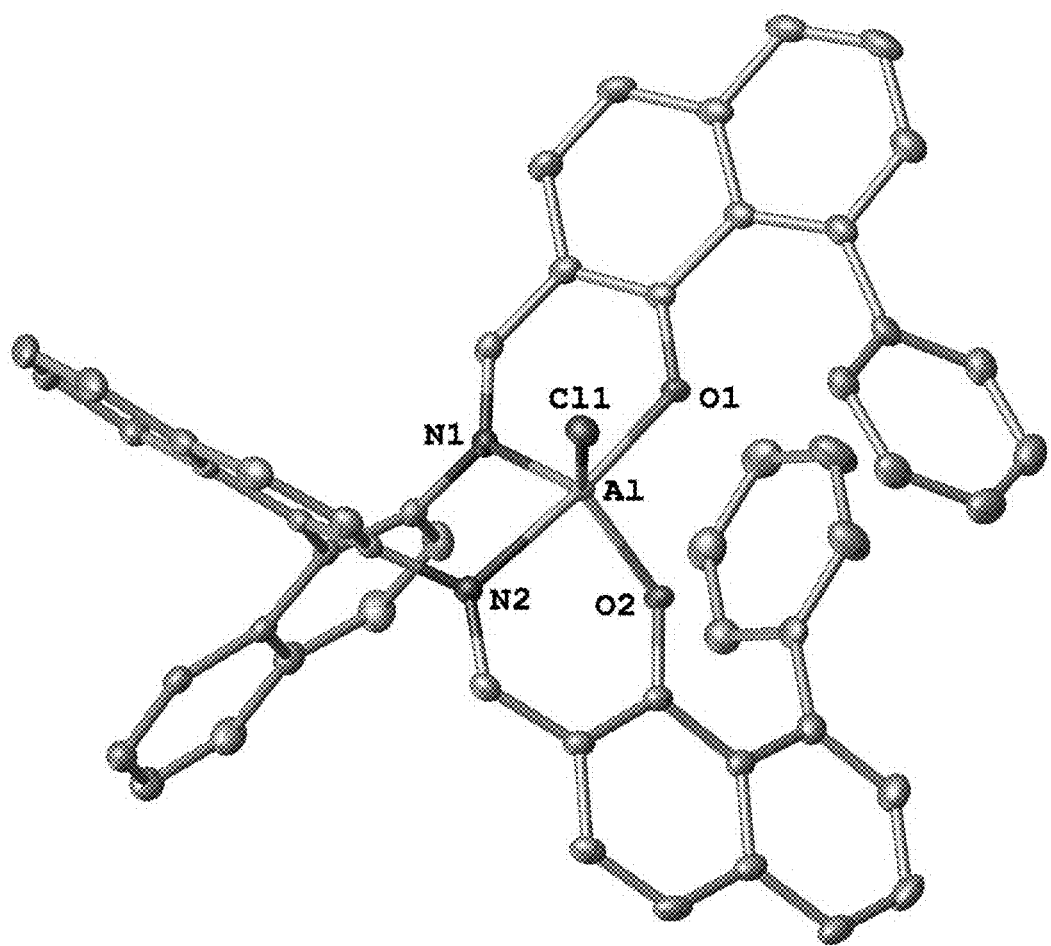
FIG. 13 shows the solid state structure of catalyst (rac)-8aAlCl.
Figure 14:
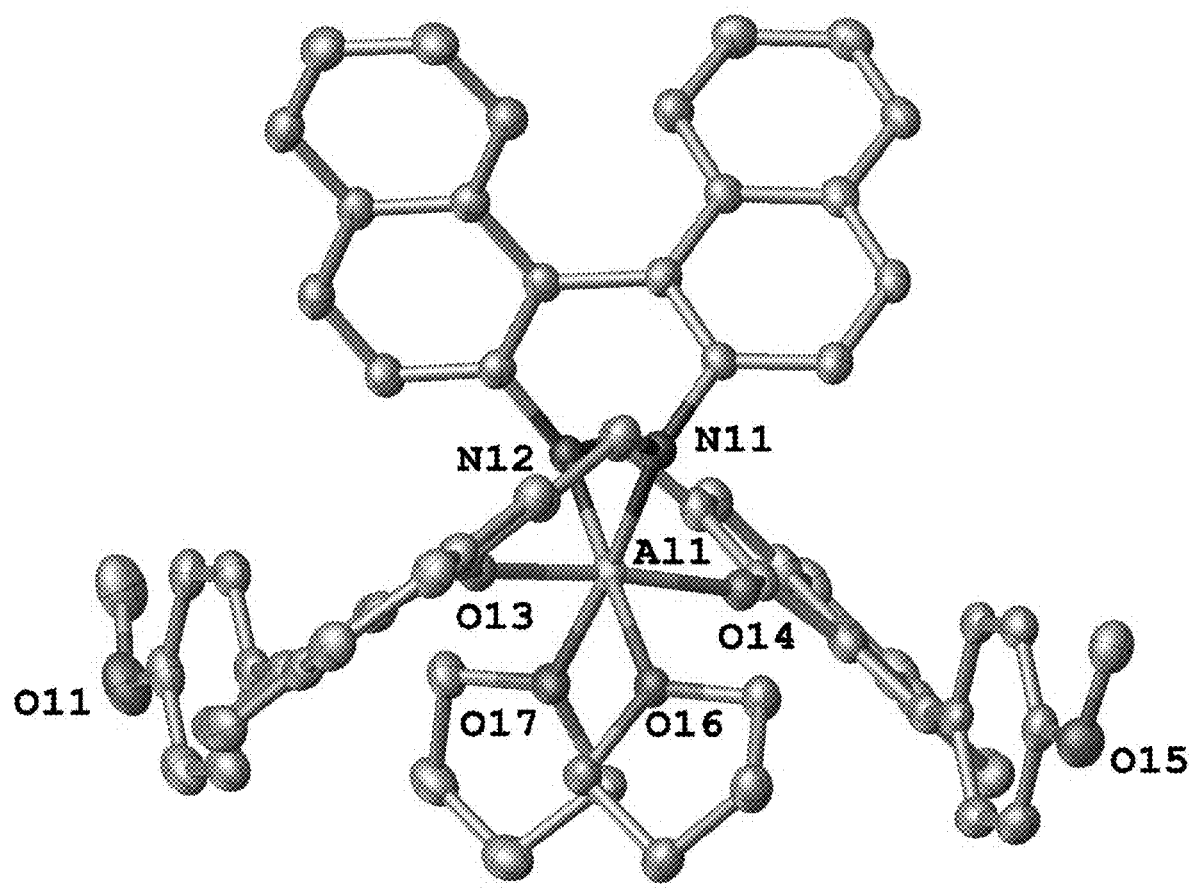
FIG. 14 shows the solid state structure of catalyst [rac-9Al(THF)$_2$][BPh$_4$].
Figure 15:
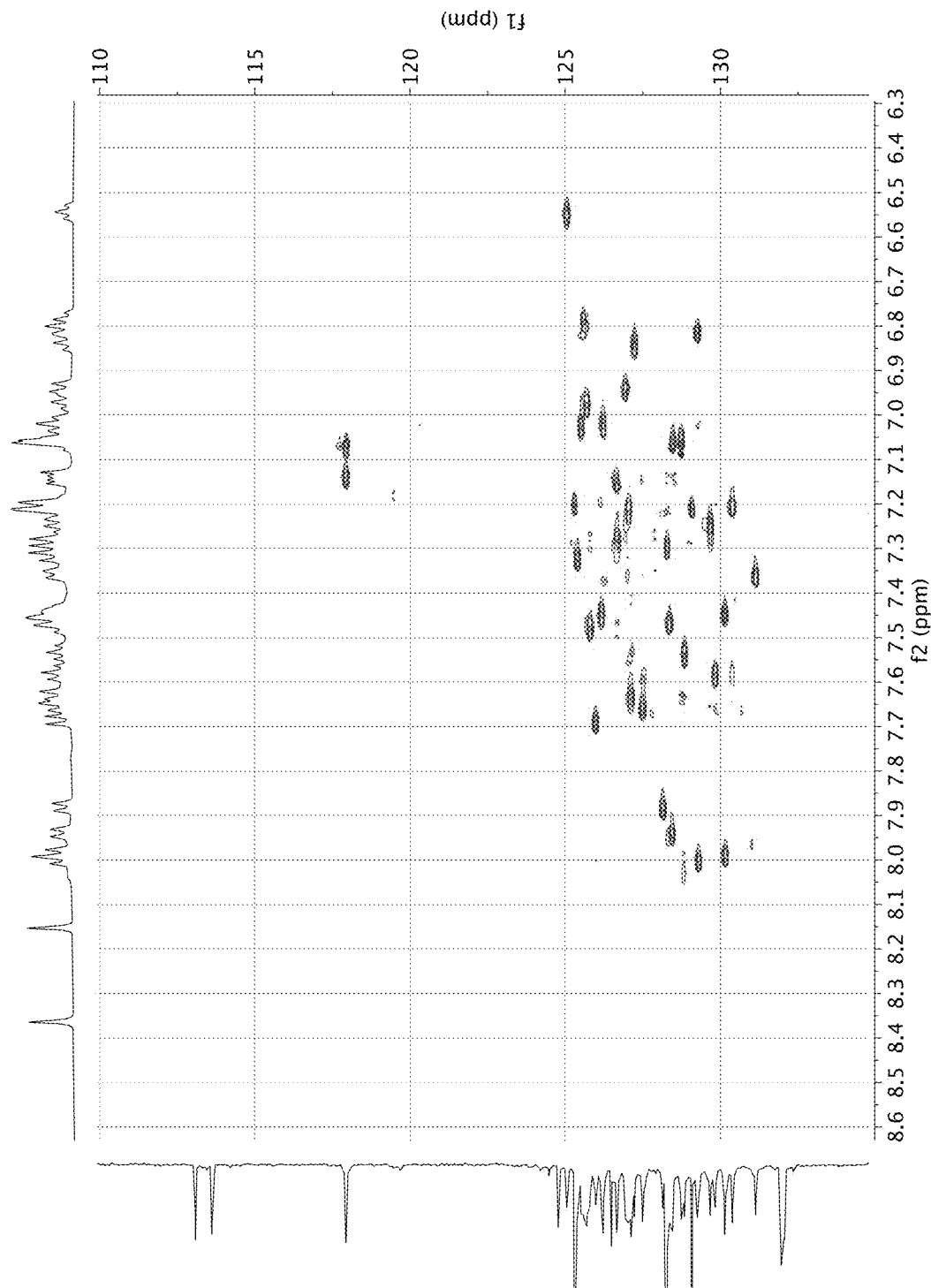
FIG. 15 shows band-selective HSQC NMR spectrum of (R)-8aAlCl (500 MHz, CDCl$_3$, −55° C.), proton chemical shifts are different at 22° C. compared to −55° C.
Figure 16:
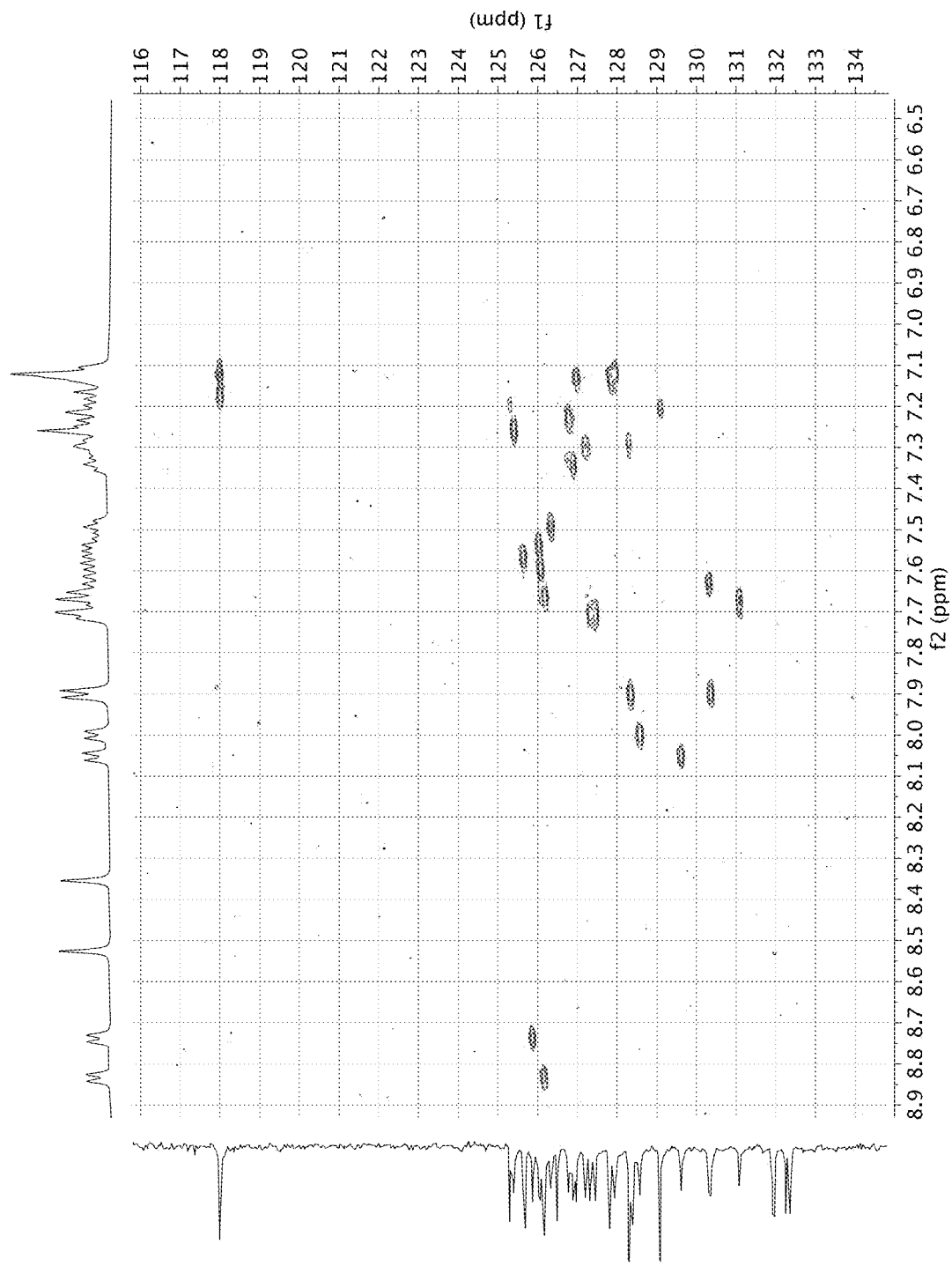
FIG. 16 shows band-selective HSQC NMR Spectrum of (R)-8bAlCl (500 MHz, CDCl$_3$, −55° C.).
Figure 17:
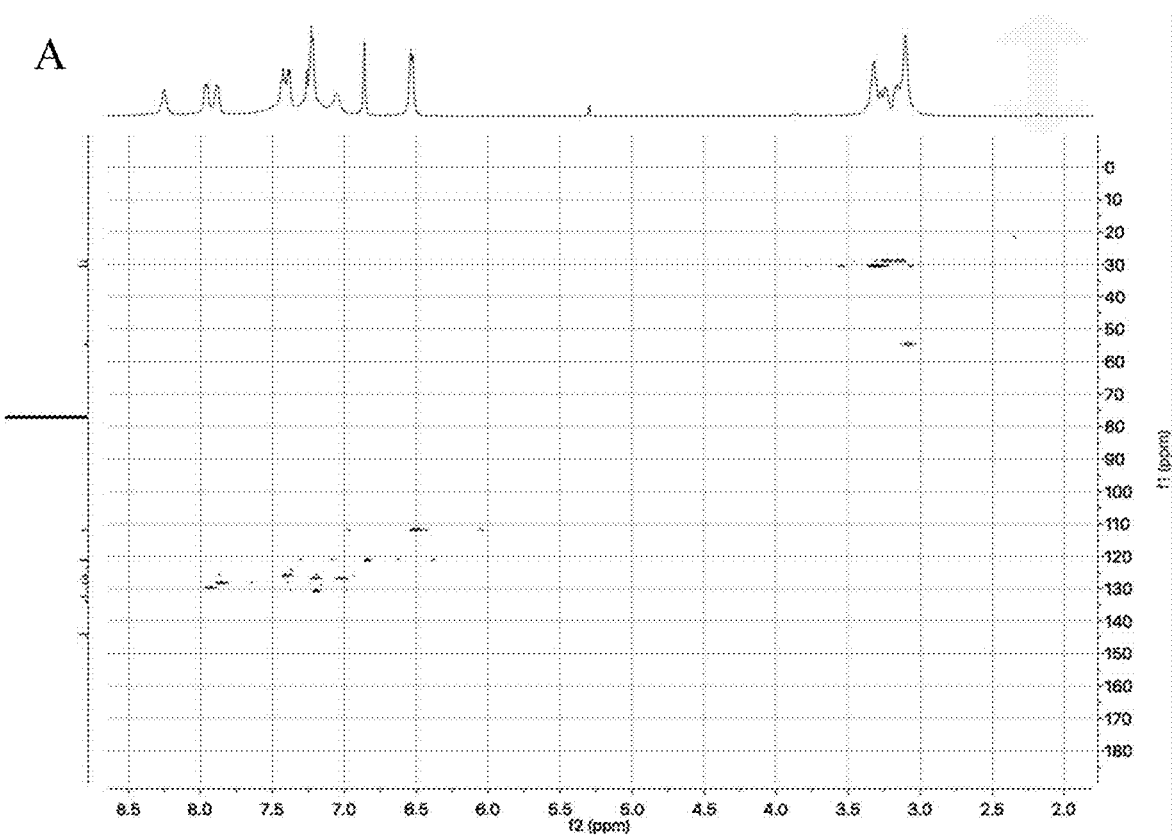
FIG. 17 shows (A) HSQC NMR spectrum of rac-9AlCl (600 MHz, CDCl$_3$, 22° C.). (B) HSQC NMR spectrum (zoomed in) of rac-9AlCl (600 MHz, CDCl$_3$, 22° C.).
Figure 17:
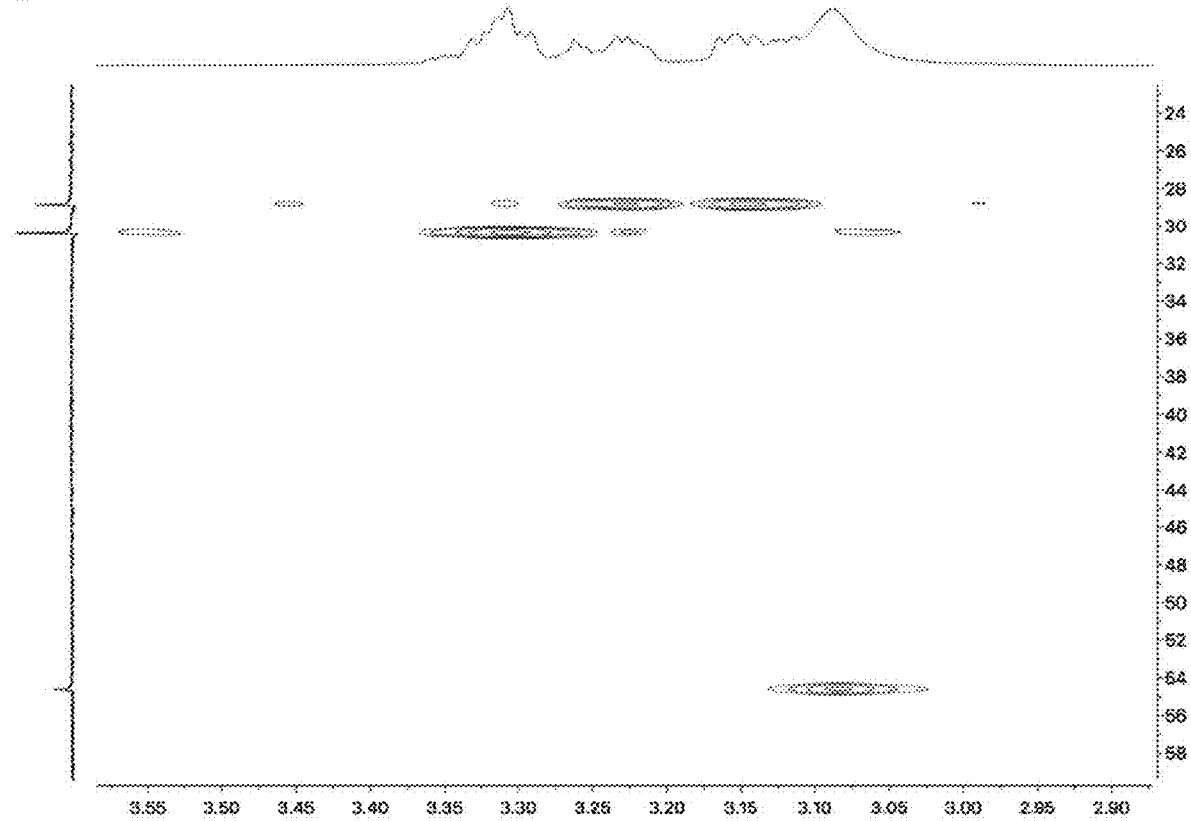

Single crystals of rac-9 were studied by X-ray diffraction (FIG. 5), revealing two potential hypotheses for the contrasteric regioselectivity: (1) the additional bulk provided by the aryl substituents guides cobaltate to attack the more sterically congested oxirane carbon, and/or (2) the flanking aryl groups stabilize positive charge accumulation at the substituted epoxide carbon (FIGS. 2 and 4) via noncovalent interactions, prompting contrasteric attack.

Solvent can influence product distributions and regioselectivities in epoxide carbonylation reactions. Therefore, a variety of solvents for the carbonylation of 1 were screened to maximize regioselectivity while minimizing the formation of 10 and 12 (FIG. 4A). Although rac-9 produced lactone with desirable regioselectivity using THF (96:4 2:3, Table 2, entry 1), 10 was still the major product. 1,4-dioxane suppressed the formation of this side product (Table 2, entry 2), but regioselectivity suffered. Therefore, it was hypothesized that using a combination of THF and 1,4-dioxane could promote the carbonylation pathway selectively and with satisfactory regioselectivity. Indeed, more lactone was formed and regioselectivity was reasonable; however, the desired product 2 still accounted for less than 50% of the reaction mixture (Table 2, entries 3 and 4). Weakly coordinating diethyl ether (Et$_2$O) and toluene both reduced overall reactivity (Table 2, entries 5 and 6), and catalyst solubility suffered using ethyl acetate (EtOAc, Table 2, entry 7). Dibasic ester-5 (dimethyl glutarate, DBE-5) increased reactivity, produced more desirable regioselectivity (97:3 2:3), and modestly suppressed side product formation, generating 2 in >50% conversion for the first time (59%, Table 2, entry 8). Further optimization revealed that decreasing the concentration from 0.5 to 0.25 M (Table 2, entry 9) and using Ph$_3$SiCo(CO)$_4$ instead of NaCo(CO)$_4$ (Table 2, entry 10) decreased side product generation and promoted additional lactone formation (66%).

TABLE 2

Effect of Solvent and Co(CO)$_4^-$ on Product Distribution and Regioselectivity[a]

|       |         | concentration | time | ratio   | % conversion[b] |    |    |    |     |
|-------|---------|---------------|------|---------|-----------------|----|----|----|-----|
|       |         |               |      |         | lactone         |    |    |    |     |
| entry | solvent | (M)           | (h)  | (2:3)[b]| (2 + 3)         | 10 | 12 | 13 | 14[c] |
| 1     | THF     | 0.50          | 18   | 96:4    | 19              | 61 | <1 | 6  | 6   |
| 2     | 1,4-dioxane | 0.50      | 18   | 76:24   | 11              | <1 | <1 | 3  | 3   |
| 3[d]  | THF:1,4-dioxane (1:1) | 0.50 | 18 | 84:16 | 29          | 19 | <1 | 16 | 16  |
| 4[d]  | THF:1,4-dioxane (1:3) | 0.50 | 18 | 88:12 | 33          | 7  | 1  | 17 | 17  |
| 5[e]  | Et$_2$O | 0.50          | 18   | >99:1   | 8               | <1 | 2  | 1  | 1   |
| 6[e]  | toluene | 0.50          | 18   | >99:1   | 3               | 7  | <1 | 2  | 2   |
| 7[d]  | EtOAc   | 0.50          | 24   | 91:9    | 25              | <1 | 9  | 2  | 2   |
| 8     | DBE-5[f]| 0.50          | 24   | 97:3    | 59              | <1 | 21 | 10 | 10  |
| 9     | DBE-5[f]| 0.25          | 24   | 95:5    | 57              | 1  | 15 | 9  | 9   |
| 10[g] | DBE-5[f]| 0.25          | 24   | >99:1   | 66              | 1  | 14 | 9  | 9   |
| 11[g,h]| DBE-5[f]| 0.25         | 2    | >99:1   | 40              | 5  | 10 | 2  | 2   |
| 12[h,i]| DBE-5[f]| 0.25         | 2    | >99:1   | 71              | 5  | 20 | 2  | 2   |

[a]Catalyst made in situ (5.0 mol % L$_n$AlCl + 5.0 mol % NaCo(CO)$_4$) unless otherwise specified. Product 11 was not observed in any of these reactions.
[b]Determined by $^1$H NMR spectroscopy of the crude reaction mixture.
[c]Diagnostic peak underneath catalyst residue. Determined by conversion to 13 (see the Supporting Information for additional details).
[d]An additional ester side product formed through the Tischenko reaction of two isobutyraldehyde molecules.
[e]Overall conversion was very low, so integrations of $^1$H NMR spectra for determination of regioselectivity may not be reliable.
[f]DBE-5 = dibasic ester-5.
[g]Catalyst made in situ (5.0 mol % L$_n$AlCl + 5.0 mol % Ph$_3$SiCo(CO)$_4$).
[h]Percent yield by $^1$H NMR spectroscopy using hexamethyldisiloxane as an internal standard due to product volatility.
[i]Catalyst made in situ (5.0 mol % L$_n$AlCl + 7.5 mol % Ph$_3$SiCo(CO)$_4$).

Prior to oxygen exposure, reactions using DBE-5 remain orange in color, characteristic of the catalyst's highly conjugated ligand. However, reactions in other solvents, such as THF and 1,4-dioxane, turned dark before reaction completion. Cobalt tetracarbonyl hydride, which is formed via β-hydrogen elimination during formation of side products 10 and 12 (FIG. 4), is known to decompose to hydrogen gas and brown dicobalt octacarbonyl. This visual observation may indicate that catalyst decomposition occurs in certain solvents but is minimized by DBE-5. Because all reactions performed using DBE-5 proceeded to full conversion in 24 hours, we decreased the reaction time to gauge the resulting increase in reaction rate. In only two hours, 59% total conversion was achieved (Table 2, entry 11), an improvement upon reactions in other solvents that did not reach completion in 24 hours (Table 2, entries 1-7). This enhanced reactivity, along with the visual observations, indicated that cobaltate degradation occurs more slowly in DBE-5. To further increase the turnover frequency, additional cobaltate was added to replenish any cobalt hydride that degrades during the course of the reaction. In the presence of 7.5 mol % Ph$_3$SiCo(CO)$_4$, full conversion was observed after 2 h (Table 2, entry 12). However, a ring-opening turnover-limiting step as reason for this increase in yield cannot be ruled out. With these improvements, 2 was generated in 71% yield, a significant improvement upon previous carbonylation methods. Although 20% of this reaction mixture consists of 12, alumina plugs can be used to remove this alcohol side product (see the below for additional details).

In conclusion, described herein is a contrasteric-selective carbonylation of isobutylene oxide for the production of pivalolactone (>99:1 2:3). It is hypothesized that the high regioselectivity of this catalyst is largely due to the epoxide binding pocket in the bulky salen catalyst, which may prevent nucleophilic attack at the less sterically hindered epoxide carbon and/or stabilize the accumulation of positive charge at the more congested site. Using DBE-5 as the solvent suppressed side product formation, minimized catalyst decomposition, and increased reaction rates. This novel regioselective carbonylation is an atom economical and potentially renewable route to pivalolactone, which may increase the practicality of commercial PPVL production.

Unless stated otherwise, all synthetic manipulations were carried out using standard Schlenk techniques under a nitrogen atmosphere or in an MBraun Unilab glovebox under an atmosphere of purified nitrogen. Reactions were carried out in oven-dried glassware cooled under vacuum. Unless otherwise noted, $^1$H NMR and $^{13}$C{$^1$H} NMR spectra were recorded on a Bruker 500 MHz instrument with a broad band Prodigy cryoprobe, a Varian INOVA 400 MHz spectrometer, or a Varian INOVA 600 MHz spectrometer at 22° C. with shifts reported relative to the residual solvent peak (CDCl$_3$: 7.26 ppm ($^1$H), and 77.16 ppm ($^{13}$C)). Data are reported as follows: chemical shift, multiplicity (s=singlet, d=doublet, t=triplet, q=quartet, sep=septet, m=multiplet), integration, and coupling constants (Hz). Deuterated chloroform was purchased from Cambridge Isotope Laboratories and stored over 3 Å molecular sieves. FIRMS analyses were performed on a Thermo Scientific Exactive Orbitrap MS system with an Ion Sense DART ion source or a Q-TOF Ultima mass spectrometer (ESI). Flash column chromatography was performed with silica gel (particle size 40-64 μm, 230-400 mesh) using DCM, mixtures of hexanes and diethyl ether, or mixtures of hexanes and ethyl acetate. All work-up and purification procedures were carried out with reagent grade solvents (purchased from Fisher) in air.

Sources of Solvents, Reagents, and Catalysts:

Acenaphthene was purchased from TCI and used as received.

Acetic acid was purchased from J. T. Baker and used as received.

(rac)-1,1'-Binaphthyl-2,2'-diamine was purchased from BOC Sciences and used as received.

N-Bromosuccinimide was purchased from Sigma-Aldrich and used as received.

"Butyllithium (1.6 M in hexanes) was purchased from Acros and used as received.

Calcium hydride was purchased from Strem and crushed with a mortar and pestle prior to use.

Carbon monoxide was purchased from Matheson (research quality/>99.99% min purity) and used as received.

Cesium carbonate was purchased from Sigma-Aldrich and used as received.

Chloromethyl methyl ether was purchased from Sigma-Aldrich and used as received.

3-Chloroperbenzoic acid was purchased from Sigma-Aldrich (≤77%) and used as received.

Decolorizing carbon was purchased from Fisher Chemical and used as received.

Deuterated chloroform was purchased from Cambridge Isotope Laboratories and stored over activated 3 Å molecular sieves.

(R)-2,2'-Diamine-1,1'-binaphthalene was purchased from Sigma-Aldrich and used as received.

Dibasic ester (DBE-5) was purchased from Sigma-Aldrich or TCI and used as received.

Dichloromethane was purchased from Fisher Chemical and sparged vigorously with nitrogen for 40 minutes before passing through two packed columns of neutral alumina under nitrogen pressure. Later it was degassed via three freeze-pump-thaw cycles prior to use.

Diethylaluminum chloride was purchased from Sigma-Aldrich and diluted to make a 1.0 M solution in dry hexanes prior to use.

Diethyl ether (anhydrous) (DME) was purchased from Fisher Chemical and used as received for catalyst synthesis. For carbonylation reactions, diethyl ether was purchased from Fisher Chemical, dried over calcium hydride for 24 h, and degassed via three freeze-pump-thaw cycles prior to use.

1,2-Dimethoxyethane was purchased from J. T. Baker and used as received.

N,N-Dimethylformamide was purchased from Sigma-Aldrich in a Sure/Seal bottle and used as received.

1,4-Dioxane was purchased from Sigma-Aldrich, dried over 3 Å molecular sieves for 24 h, syringe filtered, and sparged with nitrogen for 30 minutes prior to use.

Ethanol was purchased from Fisher Scientific and used as received.

Ethyl acetate (EtOAc) was purchased from Fisher Chemical and used as received.

Hexamethyldisiloxane was purchased from Alfa Aesar, dried over 3 Å molecular sieves for 24 h, cannula filtered off of the sieves, and degassed via three freeze-pump-thaw cycles prior to use.

Hexanes was purchased from Fisher Chemical and sparged with nitrogen for 40 minutes before passing through two packed columns of neutral alumina and copper(II) oxide under nitrogen pressure.

Hydrochloric acid was purchased from Riedel-de Haën and used as received or diluted to make a solution in deionized water prior to use.

1-Hydroxy-2-naphthaldehyde was purchased from TCI and used as received.

Iodobenzene was purchased from Sigma-Aldrich and used as received.

Isobutyl alcohol was purchased from Fisher Scientific and dried over 3 Å molecular sieves for 24 h prior to use.

Isobutylene oxide was purchased from TCI, dried over calcium hydride for 24 h, and degassed via three freeze-pump-thaw cycles prior to use.

Isobutyraldehyde (anhydrous) was purchased from Sigma-Aldrich and dried over 3 Å molecular sieves for 24 h prior to use.

Lithium hydroxide was purchased from Sigma-Aldrich and used as received.

Magnesium sulfate was purchased from Fisher Chemical and used as received.

Methacrolein was purchased from Sigma-Aldrich and dried over 3 Å molecular sieves for 24 h prior to use.

β-Methallyl Alcohol was purchased from TCI and dried over 3 Å molecular sieves for 24 h prior to use.

Methanol was purchased from Fisher Chemical and used as received.

4-Methoxyphenylboronic acid was purchased from Combi-Blocks and used as received.

1-Naphthol was purchased from Alfa Aesar and used as received.
Palladium(II) acetate was purchased from AK Scientific and used as received.
Pentane was purchased from Fisher Chemical and used as received.
Potassium carbonate was purchased from J. T. Baker and used as received.
Sodium bicarbonate was purchased from Macron Fine Chemicals and diluted to make a saturated solution in deionized water prior to use.
Sodium chloride was purchased from VWR and diluted to make a saturated solution in deionized water prior to use.
Sodium hydride was purchased from Sigma-Aldrich and used in a glovebox as received.
Sodium hydroxide was purchased from Macron Fine Chemicals, crushed, and dried under vacuum prior to use in the synthesis of NaCo(CO)$_4$, or diluted to make a solution in deionized water prior to use.
Sodium sulfate was purchased from VWR and used as received.
Sodium tetraphenylborate was purchased from Sigma-Aldrich and dried under vacuum before use.
1,3,5,7-Tetraazaadamantane (HMTA) was purchased from Oakwood Chemical and used as received.
N,N,N',N'-Tetramethylethylenediamine was purchased from Sigma-Aldrich and used as received.
Tetrahydrofuran was purchased from Fisher Chemical and sparged with nitrogen for 40 minutes before passing through two packed columns of neutral alumina and a third column packed with activated 4 Å molecular sieves under nitrogen pressure.
Toluene was purchased from Fisher Chemical and sparged with nitrogen for 40 minutes before passing through two packed columns of neutral alumina and copper(II) oxide under nitrogen pressure.
Trifluoroacetic acid was purchased from Oakwood Chemical and used as received.
Triphenylphosphine was purchased from Alfa Aesar and used as received.
Water (distilled).
Compounds prepared according to literature procedures:
NaCo(CO)$_4$
Ph$_3$SiCo(C$_0$)$_4$
Bis(tetrahydrofuran)-meso-tetra(4-chlorophenyl)porphyrinato aluminum tetracarbonyl cobaltate (4)
N,N'-Bis(3,5-di-tert-butylsalicylidene)-1,2-phenylenediaminoaluminum cobalt tetracarbonyl (5) rac-N,N'-Bis(3,5-di-tert-butylsalicylidene)-1,2-cyclohexanediaminoaluminum cobalt tetracarbonyl (6a)
rac-3,3"-((1E,1'E)-((1S,2S)-Cyclohexane-1,2-diylbis(azanylylidene))bis-(methany-lylidene))bis(4'-(tert-butyl)-2',5,6'-trimethyl-[1,1'-biphenyl]-2-olate)aluminum cobalt tetracarbonyl (rac-6b)
rac-3,3"-((1E,1'E)-([1,1'-Binaphthalene]-2,2'-diylbis(azanylylidene))-bis(methanylylidene))bis(3',5'-di-tert-butyl-5-methyl[1,1'-biphenyl]-2-olate)aluminum chloride (precursor to rac-7a)
(R)-5',5""-((1E,1'E)-([1,1'-Binaphthalene]2,2'-diylbis(azanylylidene))bis(methanylylidene))-bis(2,2",6,6"tetramethyl-[1,1':3',1"-terphenyl]-4'-olate)aluminum chloride (precursor to (R)-7 b)
Control Reactions Using rac-9. NOTE: These reactions were run with alumina plugs. See below for a comprehensive explanation of the consequences.

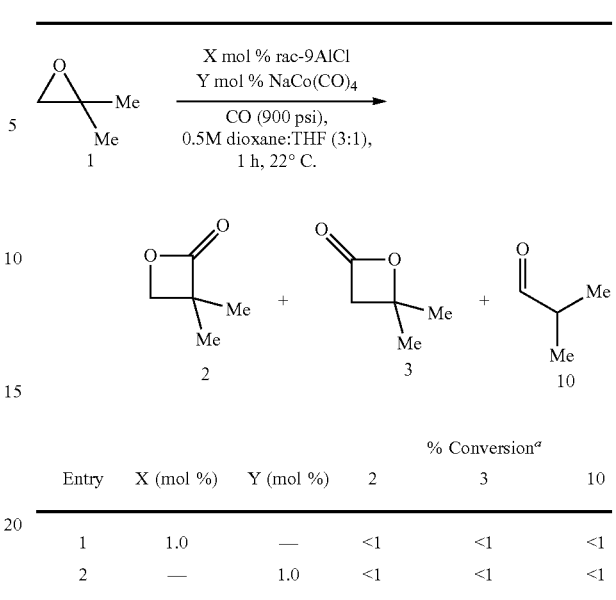

| Entry | X (mol %) | Y (mol %) | % Conversion$^a$ | | |
|-------|-----------|-----------|---|---|----|
|       |           |           | 2 | 3 | 10 |
| 1     | 1.0       | —         | <1 | <1 | <1 |
| 2     | —         | 1.0       | <1 | <1 | <1 |

$^a$Determined by $^1$H NMR spectroscopy of the crude reaction mixture.

MINO Control Reaction Using rac-9. In a glovebox, a 4 mL glass vial equipped with a Teflon-coated magnetic stir bar and septum cap was charged with rac-9AlCl, NaCo(CO)$_4$, and solvent (0.025 M with respect to catalyst). Isobutyraldehyde was added, and the vial was sealed. Outside of the glovebox, β-methallyl alcohol was added via syringe through the septa cap. The reaction was allowed to stir at 22° C. under a blanket of nitrogen. After 18 hours, the vial was opened, and a crude $^1$H NMR was taken without running the crude reaction mixture through an alumina plug. The presence of methacrolein (13) and isobutyl alcohol (14) demonstrates the possibility of an MINO reaction under carbonylation conditions.

Interpreting a Crude, Contrasteric Carbonylation $^1$H NMR Spectrum. Traditionally, our group has taken crude $^1$H NMRs by taking a pipette tip of the crude reaction mixture and running it through a plug of alumina with CDCl$_3$ into an NMR tube. This process removes catalyst residue, which may appear at chemical shifts similar to that of the desired product(s). However, this reaction produces alcohols, which stick to alumina. Therefore, two crude $^1$H NMRs were obtained. The first is taken without an alumina plug to determine relative ratios of 1, 2, 10, 11, 12, and 13. Unfortunately, chemical shifts of both 3 and 14 appear on top of catalyst peaks, which makes them impossible to integrate reliably. The second crude $^1$H NMR is taken after running the solution through an alumina plug, which eliminates catalyst residue and allows reliable integrations of both 2 and 3 to accurately measure regioselectivity. Unfortunately, 14 is unable to be integrated via either method unless the methyl doublet is well resolved. However, these reactions have been run with an internal standard (HMDS) that confirms when 100% of material is retained the relative amount of 14 is equal to that of 13, which is expected. This calculation was performed for Table 2.

$^1$H NMR, $^{13}$C NMR, and FIRMS of Catalyst Intermediates, Catalysts, and Pivalolactone. All compounds are previously unreported unless otherwise stated.

Synthesis of (R)-8a: 8-Phenylnaphthalen-1-ol (S2)

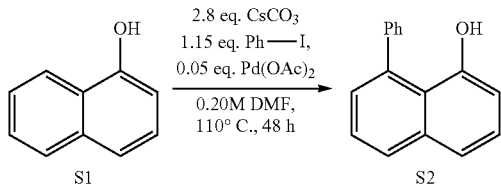

1-Naphthol (S1, 1.0 eq.), Cs$_2$CO$_3$ (2.8 eq.), and DMF (0.27 M with respect to 1-naphthol) were added to a Schlenk flask under a flow of nitrogen. Iodobenzene (1.15 eq.) was added to the reaction mixture via syringe, and the flask was put in an oil bath (110° C.). A solution of Pd(OAc)$_2$ (0.05 eq.) in anhydrous DMF (0.04 M with respect to Pd(OAc)$_2$) was cannula transferred into the reaction flask in portions over a period of 5 hours. Once all the Pd(OAc)$_2$ had been added, the reaction was stirred at 110° C. for 48 hours. The reaction was then cooled to room temperature before quenching with 1.0 M HCl until the solution turned tan or clear yellow. The solution was filtered through Celite® to remove residual palladium black using distilled water and ethyl acetate. Next, the aqueous layer was extracted with EtOAc (3×) to remove the yellow color (using more water helped by diluting the DMF in the aqueous layer). The combined organic layers were washed with water (3×), dried over Na$_2$SO$_4$, gravity filtered, and concentrated. The product was purified by flash column chromatography (75:1→50:1 hexanes:EtOAc) to yield a yellow oil (S2, 1.06 g, 57%). Analytical data match literature values. $^1$H NMR (500 MHz, CDCl$_3$): δ 7.87 (dd, 1H, J=8.3, 1.0 Hz), 7.50-7.54 (m, 6H), 7.45 (dd, 1H, J=8.2, 7.1 Hz), 7.41 (t, 1H, J=7.8 Hz), 7.21, (dd, 1H, J=7.0, 1.1 Hz), 6.92 (dd, 1H, J=7.6, 1.1 Hz), 5.41 (s, 1H). $^{13}$C NMR (125 MHz, CDCl$_3$): δ 153.2, 141.5, 136.3, 135.9, 129.6, 129.1, 128.9, 128.7, 128.6, 127.0, 125.0, 121.5, 121.2, 112.0. HRMS (DART): Calcd for M=C$_{16}$H$_{12}$O, [M+H]$^+$: 221.0961. Found: 221.0971.

1-(Methoxymethoxy)-8-phenylnaphthalene (S3)

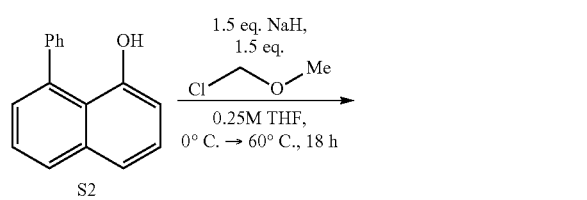

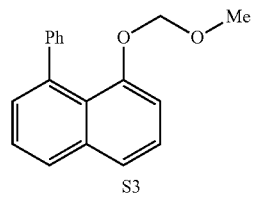

In a glovebox, 8-phenylnaphthalen-1-ol (S2, 1.0 eq.) was transferred to a pear-shaped flask topped with a Schlenk adapter using THF (0.53 M with respect to S2). Sodium hydride (1.5 eq.) was measured out in a separate Schlenk flask, and THF (0.60 M with respect to NaH) was added. Both flasks were pumped out of the glovebox and onto a Schlenk line. The sodium hydride solution was cooled to 0° C. The naphthol solution was slowly cannula transferred into the sodium hydride, resulting in hydrogen evolution. Chloromethyl methyl ether (1.5 eq.) was added dropwise via syringe. The reaction was then put in a preheated oil bath (60° C.) and stirred for 18 hours, after which the solution was cooled to 22° C. and quenched with the dropwise addition of 1 M HCl until hydrogen production ceased. Diethyl ether was then added, and the reaction was allowed to stir for 1 hour to achieve complete consumption of the sodium hydride. The aqueous layer was extracted with diethyl ether (3×), and the organics were washed with brine, dried over Na$_2$SO$_4$, gravity filtered, and concentrated. The product was purified via flash column chromatography (60:1→40:1 hexanes:EtOAc) to yield an off-white solid (S3, 1.30 g, 83%). Note that to fast-track the synthesis, this column purification step may be skipped. Purification can happen later after generation of S5. $^1$H NMR (500 MHz, CDCl$_3$): δ 7.83 (dd, 1H, J=8.2, 0.8 Hz), 7.57 (d, 1H, J=8.2 Hz), 7.47 (dd, 1H, J=8.0, 7.1 Hz), 7.39 (t, 1H, J=7.9), 7.29-7.36 (m, 5H), 7.28 (dd, 1H, J=7.0, 1.1 Hz), 7.04 (dd, 1H, J=7.6, 0.8 Hz), 4.71 (s, 2H), 3.16 (s, 3H). $^{13}$C NMR (125 MHz, CDCl$_3$): δ 154.1, 145.5, 138.9, 135.9, 129.3, 128.9, 127.9, 126.8, 126.2, 125.9, 125.4, 124.0, 122.5, 110.13, 94.8, 56.2. HRMS (DART): Calcd for M=C$_{18}$H$_{16}$O$_2$, [M+H]$^+$: 265.1223. Found: 265.1228.

1-(Methoxymethoxy)-8-phenyl-2-naphthaldehyde (S4)

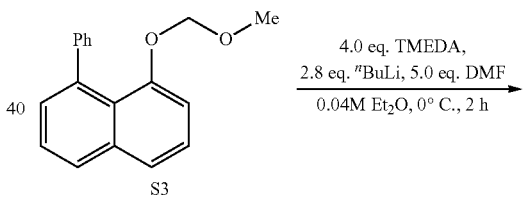

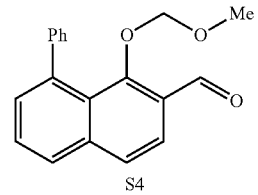

In a glovebox, 1-(methoxymethoxy)-8-phenylnaphthalene (S3, 1.0 eq.) was transferred to a Schlenk flask using diethyl ether (0.04 M). The flask was pumped onto a Schlenk line, and dry N,N,N',N'-tetramethylethylenediamine (4.0 eq.) was added via syringe as the flask was cooled to 0° C. nBuLi (1.6 M in hexanes, 2.8 eq.) was added dropwise over 15 minutes before stirring for 1 hour at 0° C. DMF (5.0 eq.) was added slowly, and the reaction was allowed to stir for 2 hours at 0° C. The reaction was quenched with 1.0 M HCl and stirred for at least an hour. The organics were extracted with EtOAc (3×), then the combined organic layers were washed with NaHCO$_3$, washed with brine, dried over Na$_2$SO$_4$, filtered, and concentrated. The product was purified via flash column chromatography (75:1→30:1 hexanes:EtOAc) to give a yellow oil (S4, 0.76 g, 80%). The product partially crystallized after standing at room temperature for four days, but a solid product is unnecessary to carry forward to the deprotection step. Note that to fast-track the synthesis, this column purification step may be skipped. Purification can happen later after generation of S5. $^1$H NMR (600 MHz, CDCl$_3$): δ 10.48 (d, 1H, J=0.8 Hz), 7.93 (d, 1H, J=8.5 Hz), 7.89 (dd, 1H, J=8.2, 1.1 Hz), 7.76 (d, 1H, J=8.6 Hz), 7.63 (dd, 1H, J=8.1, 7.2 Hz), 7.41-7.46 (m, 5H), 7.37-7.41 (m, 1H), 4.14 (s, 2H), 3.22 (s, 3H). $^{13}$C NMR (100 MHz, CDCl$_3$): δ 191.4, 160.0, 142.7, 139.8, 139.5, 131.2, 129.7, 128.7, 128.3, 127.8, 127.4, 127.0, 125.9, 125.5, 122.7, 101.3, 57.9. HRMS (DART): Calcd for M=C$_{19}$H$_{16}$O$_3$, [M+H]$^+$: 293.1172. Found: 293.1177.

1-Hydroxy-8-phenyl-2-naphthaldehyde (S5)

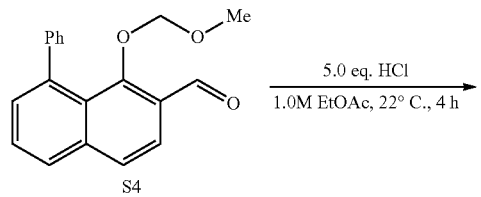

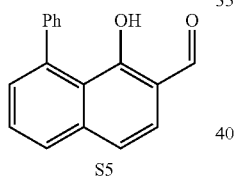

1-(Methoxymethoxy)-8-phenyl-2-naphthaldehyde (S4, 1.0 eq.) was dissolved in EtOAc (1.0 M). HCl (5.0 eq.) was added dropwise at 22° C. and then left to stir for 4 hours. EtOAc and H$_2$O were added to separate the layers. Organics were extracted with EtOAc (3×). The combined organic layers were washed with NaHCO$_3$ (3×), washed with brine (1×), dried over Na$_2$SO$_4$, gravity filtered, and concentrated. Flash column chromatography (hexanes:EtOAc 30:1) yielded the product as a yellow oil (S5, 0.60 g, 92%). Note that to fast-track the synthesis, the column purification steps for S3 and S4 may be skipped, only fully purifying S5, without any loss in yield (and generally higher yield) over the three steps. $^1$H NMR (500 MHz, CDCl$_3$): δ 12.79 (s, 1H), 9.91 (s, 1H), 7.80 (dd, 1H, J=8.2, 0.9 Hz), 7.65 (dd, 1H, J=7.9, 7.3 Hz), 7.50 (d, 1H, J=8.5 Hz), 7.45 (d, 1H, J=8.5 Hz), 7.37-7.43 (m, 5H), 7.34 (dd, 1H, J=7.1, 1.1 Hz). $^{13}$C NMR (100 MHz, CDCl$_3$): δ 196.2, 163.7, 143.7, 142.2, 139.0, 130.2, 129.7, 128.9, 127.9, 127.3, 127.2, 126.8, 122.2, 120.3, 115.1. HRMS (DART): Calcd for M=C$_{17}$H$_{12}$O$_2$, [M+H]$^+$: 249.0910. Found: 249.0906.

(R)-2,2'-((1E,1'E)-([1,1'-Ninaphthalene]-2,2'-diylbis(azanylylidene))bis(methanylylidene))bis(8-phenylnaphthalen-1-ol) (S6)

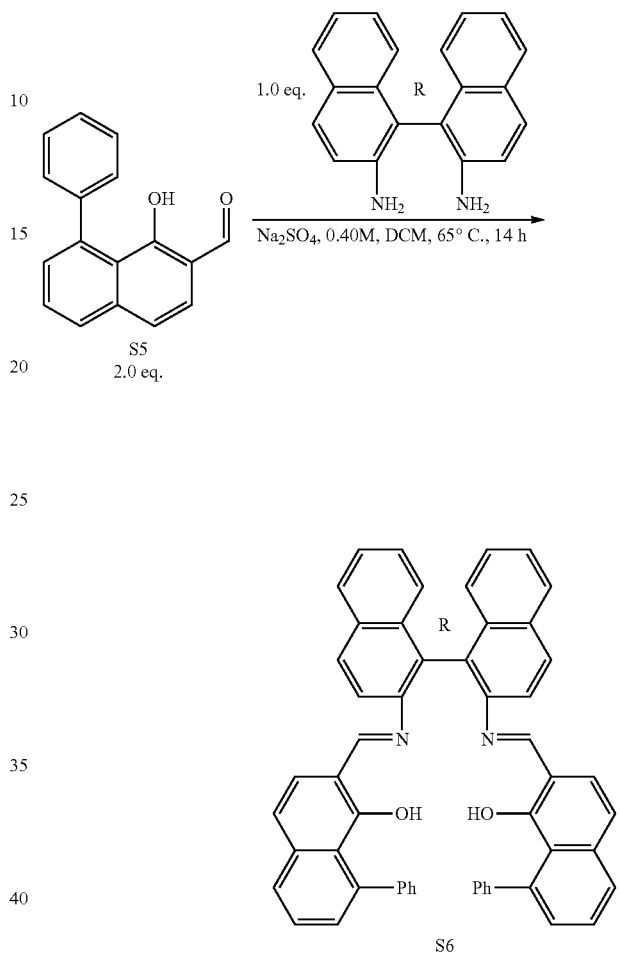

1-Hydroxy-8-phenyl-2-naphthaldehyde (S5, 2.0 eq.) and (R)-2,2'-diamine-1,1'-binaphthalene (1.0 eq.) were suspended in DCM (0.40 M). A scoop of Na$_2$SO$_4$ was added before sealing the vial and stirring in a preheated oil bath (65° C.). After 14 hours, the reaction was cooled and Na$_2$SO$_4$ was filtered off. The product was purified by flash column chromatography (dry load, hexanes:EtOAc 9:1) to give a red orange solid (S6, 0.511 g, 57%). $^1$H NMR (500 MHz, CDCl$_3$): δ 14.14 (d, 2H, J=5.0 Hz), 8.24 (d, 2H, J=5.0 Hz), 7.91 (app. t, 4H), 7.56 (dd, 2H, J=8.0, 1.0 Hz), 7.27-7.50 (m, 12H), 7.20 (m, 2H), 7.04-7.16 (m, 10H), 6.99 (d, 2H, J=8.7 Hz). $^{13}$C NMR (125 MHz, CDCl$_3$): δ 170.0, 157.0, 145.0, 142.2, 140.3, 137.8, 133.2, 132.0, 130.4, 129.2, 128.7, 128.51, 128.49, 128.1, 127.4, 127.0, 126.3, 125.73, 125.68, 125.5, 124.8, 117.5, 116.7, 112.3 (Note: There should be 25 $^{13}$C resonances, but only 24 were observed. It is believed that two signals coincidentally overlap). FIRMS (DART): Calcd for M=C$_{54}$H$_{36}$N$_2$O$_2$, [M+H]$^+$: 745.2850. Found: 745.2880.

(R)-2,2'-((1E,1'E)-([1,1'-Binaphthalene]-2,2'-diyl-bis(azanylylidene))bis(methanylylidene))bis(8-phenylnaphthalen-1-olate)aluminum chloride (R)-8aAlCl

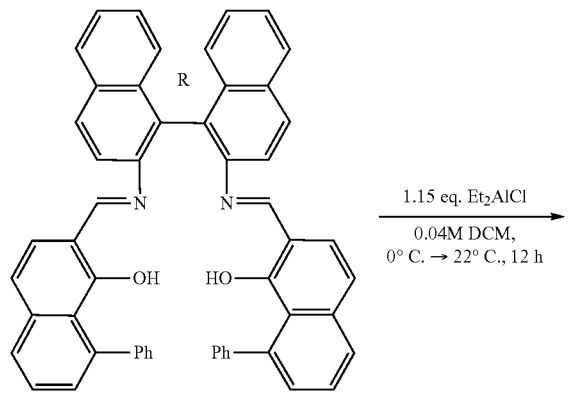

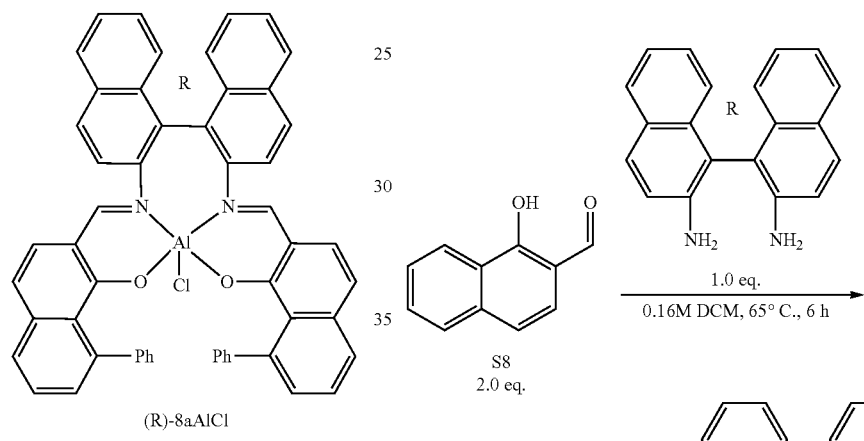

(R)-2,2'-((1E,1'E)-([1,1'-Binaphthalene]-2,2'-diylbis(azanylylidene))bis(methanylylidene))bis(8-phenylnaphthalen-1-ol) (S7, 1.0 eq.) was added to a pumped down Schlenk flask. DCM (0.04 M with respect to S7) was cannula-transferred into the flask, which was then cooled to 0° C. 1.15 eq. of a 0.98 M solution of Et$_2$AlCl was then added dropwise using a gastight syringe. The reddish solution was taken out of the ice bath and allowed to warm to 22° C. and was stirred overnight. The DCM was removed in vacuo and the solid residue was re-dissolved in toluene. Next, the solution was layered with pentane to crash out the complex. The orange powder was isolated via filtration, washed with pentane, and dried overnight in vacuo ((R)-8aAlCl, 0.301 g, 77%). (rac)-8aAlCl can be synthesized in the same manner as (R)-8aAlCl. Crystals suitable for single crystal X-ray diffraction analysis were grown from a concentrated solution of (rac)-8aAlCl in CDCl$_3$ in an NMR tube. $^1$H NMR (600 MHz, CDCl$_3$, 22° C.): δ 8.23 (s, 2H), 7.97 (d, 2H, J=8.7 Hz), 7.89 (d, 2H, J=8.3 Hz), 7.65 (dd, 2H, J=8.1, 1.2 Hz), 7.27-7.61 (m, two sharp at 7.55 (t, J=7.5 Hz) and 7.44 (dd, 10H, J=6.9, 1.0 Hz) with broad signals overlapping and underneath), 7.19-7.23 (m, 4H, Note: this signal is surrounded by residual toluene peaks), 7.12 (d, 2H, J=8.7 Hz), 7.08 (d, 2H, J=8.7 Hz), 7.02 (br, 2H), 6.92 (br s, 4H), 6.65 (t, 2H, J=7.2 Hz). $^{13}$C NMR (125 MHz, CDCl$_3$, 22° C.): δ 144.7, 143.4, 139.8, 132.54, 132.48, 130.1, 129.8, 129.4, 128.7, 128.4, 127.3, 127.0, 126.9, 126.4, 126.1, 125.9, 125.8, 125.4, 118.1, 113.9. (Note: Signals at 138.1, 129.2, 128.37, 125.44, and 21.6 are due to residual toluene. Some signals are difficult to see due to broadness at 22° C.). $^{13}$C NMR (125 MHz, CDCl$_3$, −55° C.): δ 172.1, 169.2, 167.1, 165.0, 144.5, 143.9, 143.7, 143.3, 142.8, 141.8, 139.7, 138.8, 132.1, 132.04, 131.96, 131.1, 130.4, 130.1 (2C), 129.9, 129.7, 129.30, 129.26, 128.8, 128.7, 128.46, 128.44, 128.4, 128.1, 127.5, 127.2, 127.1, 127.04, 127.00, 126.9, 126.7 (2C), 126.5, 126.22, 126.17, 126.0, 125.8, 125.7, 125.6, 125.5, 125.40, 125.37, 125.3, 125.1, 124.8, 117.9 (2C), 113.6, 113.1 (Note: signals at 138.0, 129.1, 128.3, 125.30, and 21.7 are due to residual toluene. There is also another small impurity in this sample with peaks at 171.5, 165.8, 143.8, 142.9, and 139.6. Band-selective HSQC shows overlapping carbon peaks). HRMS (DART) m/z calculated for M=C$_{54}$H$_{34}$N$_2$O$_2$AlCl, [M+H]$^+$: 805.2197, found 805.2173.

Synthesis of (R)-8b: (R)-2,2'-((1E,1'E)-([1,1'-Binaphthalene]-2,2'-diylbis(azanylylidene))bis(methanylylidene))bis(naphthalen-1-ol) (S9)

1-Hydroxy-2-naphthaldehyde (S8, 2.0 eq.) and (R)-2,2'-diamine-1,1'-binaphthalene (1.0 eq.) were stirred in MeOH (0.16 M) in a vial, which was sealed and heated at 65° C. for 6 hours. The resulting product was hot filtered away from black sludge using DCM and crystallized from MeOH to give a reddish powder (S9, 0.31 g, 60%). $^1$H NMR (500 MHz, CDCl$_3$): δ 13.91 (d, 2H, J=4.0 Hz), 8.54 (d, 2H, J=4.0 Hz), 8.16 (d, 2H, J=8.9 Hz), 8.13 (d, 2H, J=8.3 Hz), 8.01 (d, 2H, J=8.2 Hz), 7.74 (d, 2H, J=8.9 Hz), 7.55 (d, 2H, J=8.0 Hz), 7.43-7.50 (m, 4H), 7.26-7.36 (m, 6H), 7.00 (d, 2H, J=8.7 Hz), 6.94 (d, 2H, J=8.7 Hz). $^{13}$C NMR (125 MHz, CDCl$_3$): δ 167.1, 158.7, 141.8, 136.5, 133.5, 132.5, 130.6, 129.5, 128.5, 127.7, 127.4, 127.3, 127.0, 126.7, 126.4, 125.9, 125.2, 124.8, 117.3, 117.1, 111.8. HRMS (DART) m/z calculated for M=C$_{42}$H$_{28}$N$_2$O$_2$, [M+H]$^+$: 593.2224, found 593.2248.

(R)-2,2'-((1E,1'E)-([1,1'-Binaphthalene]-2,2'-diylbis(azanylylidene))bis(methanylylidene))bis(naphthalen-1-olate)aluminum chloride ((R)-8bAlCl)

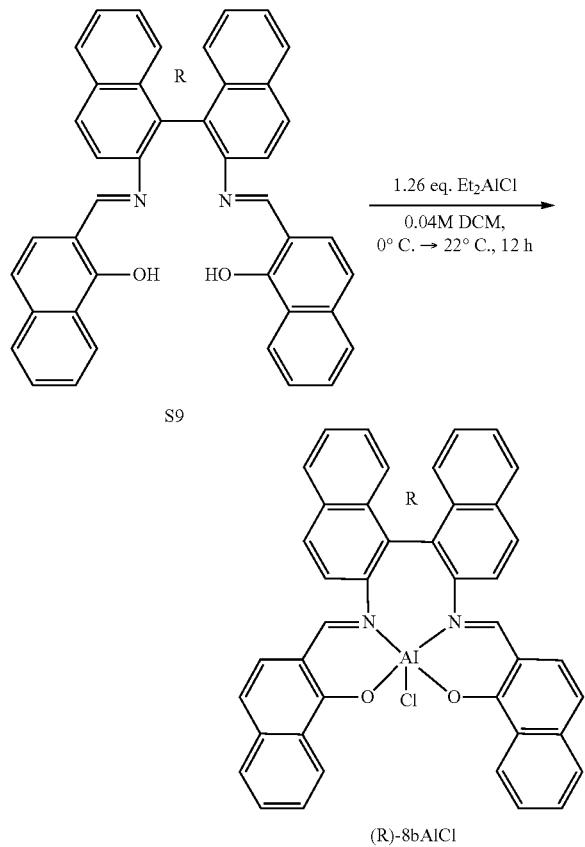

(R)-2,2'-((1E,1'E)-([1,1'-binaphthalene]-2,2'-diylbis(azanylylidene))bis(methanylylidene))bis(naphthalen-1-ol) (S9, 1.0 eq.) was added to pumped down Schlenk flask. DCM (0.04 M) was cannula-transferred into the flask, which was then cooled to 0° C. 1.26 eq. of a 0.98 M solution of Et$_2$AlCl was then added dropwise using a gastight syringe. The orange solution was taken out of the ice bath and allowed to warm to 22° C. and stir overnight. The DCM was removed in vacuo, and the solid residue was redissolved in toluene and layered in pentane to crash out the complex. The orange powder was isolated via filtration, washed with pentane, and dried overnight in vacuo ((R)-8bAlCl, 0.198 g, 78%). $^1$H NMR (500 MHz, CDCl$_3$, −55° C.): δ 8.83 (d, 1H, J=8.0 Hz), 8.74 (d, 1H, J=8.1 Hz), 8.53 (s, 1H), 8.35 (s, 1H), 8.05 (d, 1H, J=8.7 Hz), 8.00 (d, 1H, J=8.2 Hz), 7.90 (d, 2H, J=8.3 Hz), 7.45-7.75 (m, 10H), 7.27-7.38 (m, 3H), 7.07-7.17 (m, 5H) (Note: 7.17-7.25 (m) and 2.36 (s) are residual toluene from the recrystallization). $^{13}$C NMR (125 MHz, CDCl$_3$, −55° C.): δ 172.2, 169.3, 168.0, 164.2, 144.1, 143.9, 138.1, 137.4, 132.4, 132.3, 132.0, 131.9, 131.1, 130.4, 130.3, 129.6, 128.6, 128.4, 128.3, 127.9, 127.83, 127.82, 127.5, 127.3, 127.2, 127.0, 126.9, 126.8, 126.5, 126.3, 126.2 (2C), 126.1, 126.0, 125.9, 125.7, 125.6, 125.4, 118.0 (2C), 113.5, 112.0 (Note: peaks at 138.1, 129.1, 128.3, 125.3, and 21.7 are due to residual toluene. Band-selective HSQC shows overlapping carbon peaks). HRMS (DART) m/z calculated for M=C$_{42}$H$_{26}$N$_2$O$_2$AlCl$^+$, [M+H]$^+$: 653.1571, found 653.1570.

Synthesis of rac-9:
5,6-Dibromo-1,2-dihydroacenaphthylene (S11)

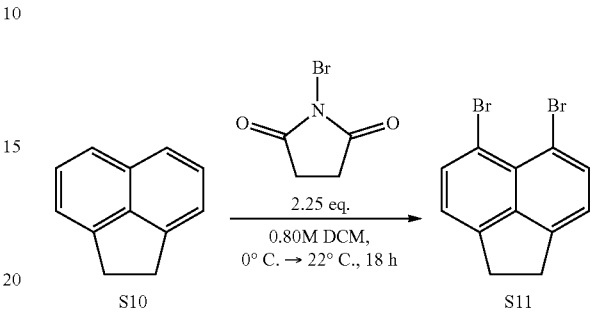

Acenaphthene (S10, 1.0 eq.) was added to a flame-dried Schlenk flask equipped with a stir bar. DMF was cannula transferred into the Schlenk flask to form a 4.0 M solution, which was cooled to 0° C. In a separate flame-dried Schlenk flask, 2.25 eq. NBS was dissolved in DMF to make a 1.0 M solution that was cannula transferred into the acenaphthene solution. After approximately 2 hours, a precipitate crashed out, and the reaction was allowed to stir for an additional 18 hours. 100 mL of ethanol was added, the reaction mixture was filtered using a fritted funnel, and the solid was washed with pentane. 5,6-Dibromo-1,2-dihydroacenaphthylene was isolated as a beige solid (S11, 15.75 g, 20% yield). A minor impurity can be seen in the $^1$H NMR, which can be minimized by washing with additional pentane and separated by column chromatography after the second synthetic step, detailed in the following procedure. Analytical data match literature values. $^1$H NMR (500 MHz, CDCl$_3$): δ 7.79 (d, 2H, J=7.5 Hz), 7.09 (d, 2H, J=7.4 Hz), 3.30 (s, 4H); $^{13}$C NMR (125 MHz, CDCl$_3$): δ 147.2, 142.1, 136.0, 128.0, 121.1, 114.6, 30.2. FIRMS (ESI): Calc'd for M=C$_{12}$H$_8$Br$_2$ [M]$^{-+}$: 309.8993. Found: 309.9005.

6-Bromo-1,2-dihydroacenaphthylene-5-carbaldehyde (S12)

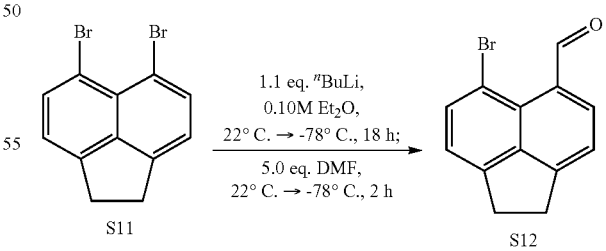

5,6-Dibromo-1,2-dihydroacenaphthylene (S11, 1.0 eq.) was added to a flame-dried Schlenk flask equipped with a stir bar. Anhydrous diethyl ether was measured out using a graduated cylinder and added into the Schlenk flask to make a 0.1 M solution of S$_{11}$, which was subsequently cooled to −78° C. 1.1 eq. of nBuLi (1.6 M in hexanes) was cannula transferred into an addition funnel fitted onto the Schlenk flask. Once all of the "BuLi was added dropwise, the flask was allowed to stir and warm to 22° C. for 18 hours. The reaction was again cooled to −78° C. before the addition of anhydrous DMF. The reaction mixture was allowed to stir for 2 hours. After the addition of 1.0 M HCl, the reaction stirred for an additional hour. The aqueous layer was extracted with benchtop diethyl ether (3×), dried with $MgSO_4$, and concentrated. 6-Bromo-1,2-dihydroacenaphthylene-5-carbaldehyde was purified using gradient silica gel column chromatography (100% hexanes, 95:5 hexanes:$Et_2O$→90:10 hexanes:$Et_2O$→80:20 hexanes:$Et_2O$) and collected as a beige solid (S12, 4.11 g, 53%). However, S12 may be carried forward without column chromatography without impact to yields. Analytical data match literature values. $^1H$ NMR (500 MHz, $CDCl_3$): δ 11.64 (s, 1H), 8.12 (d, 1H, J=7.4 Hz), 7.85 (d, 1H, J=7.5 Hz), 7.39 (d, 1H, J=7.3 Hz), 7.22 (d, 1H, J=7.5 Hz), 3.44-3.37 (m, 4H); $^{13}C$ NMR (125 MHz, $CDCl_3$): δ 192.2, 153.9, 147.1, 141.6, 135.4, 132.5, 131.2, 129.7, 121.4, 120.2, 112.9, 30.9, 30.1; HRMS (DART): Calcd for M=$C_{13}H_9BrO$, [M+H]$^+$: 260.9910. Found: 260.9913.

6-Bromo-1,2-dihydroacenaphthylen-5-yl formate (S13)

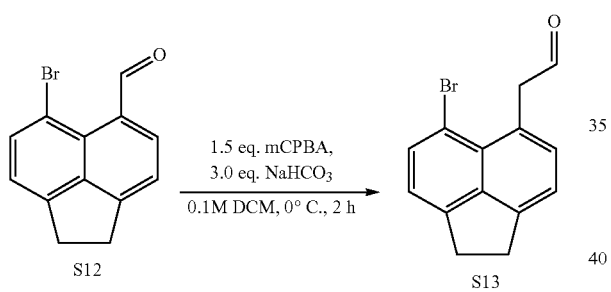

1.5 eq. of mCPBA was dissolved in DCM in a round bottom flask at 0° C. 3.0 eq. of $NaHCO_3$ was slowly added through the top of the flask followed by 6-bromo-1,2-dihydroacenaphthylene-5-carbaldehyde (S12, 1.0 eq.). The reaction was monitored by crude $^1H$ NMR. Upon consumption of 6-bromo-1,2-dihydroacenaphthylene-5-carbaldehyde, additional DCM was added before filtering through Celite®. The organics were washed with $NaHCO_3$ (3×), water (2×), and brine (1×), dried with $MgSO_4$, filtered, and concentrated. 6-Bromo-1,2-dihydroacenaphthylen-5-yl formate can be purified using gradient silica gel column chromatography (100% hexanes→95:5 hexanes:$Et_2O$→90:10 hexanes:$Et_2O$) and collected as a beige solid (S13, 2.65 g, 61%). However, a column is usually not necessary. Analytical data match literature values. $^1H$ NMR (500 MHz, $CDCl_3$): δ 8.43 (s, 1H), 7.69 (d, 1H, J=7.4 Hz), 7.28 (d, 1H, J=7.5 Hz), 7.18 (d, 1H, J=7.5 Hz), 7.13 (d, 1H, J=7.4 Hz), 3.40-3.34 (m, 4H); $^{13}C$ NMR (125 MHz, $CDCl_3$): δ 160.7, 146.5, 145.7, 142.3, 141.8, 134.5, 123.4, 122.7, 121.2, 120.0, 110.7, 30.5, 30.3. FIRMS (ESI): Calc'd for M=$C_{13}H_9BrO_2$ [M]$^{-+}$: 275.9786. Found: 275.9793.

6-Bromo-1,2-dihydroacenaphthylen-5-ol (S14)

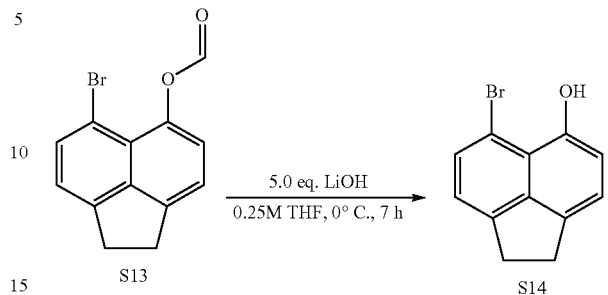

6-Bromo-1,2-dihydroacenaphthylen-5-yl formate (S13, 1.0 eq.) was dissolved in benchtop THF to make a 0.25 M solution which was cooled to 0° C. before the addition of 5.0 eq. of LiOH. The reaction was monitored by crude $^1H$ NMR. Upon consumption of starting material, water was added to the reaction mixture. The aqueous phase was extracted with ethyl acetate until colorless. Organic layers were combined, dried with $MgSO_4$, and concentrated. 6-Bromo-1,2-dihydroacenaphthylen-5-ol can be purified using gradient silica gel column chromatography (100% hexanes→95:5 hexanes:$Et_2O$→90:10 hexanes:$Et_2O$), although it is not always necessary, and was collected as a beige solid (S14, 2.03 g, 85%). Analytical data match literature values. $^1H$ NMR (500 MHz, $CDCl_3$): δ 7.59 (s, 1H), 7.46 (d, 1H, J=7.4 Hz), 7.17 (d, 1H, J=7.6 Hz), 7.01-6.99 (m, 2H), 3.28 (s, 4H); $^{13}C$ NMR (125 MHz, $CDCl_3$): δ 149.5, 146.9, 142.1, 137.9, 131.8, 121.2, 120.1, 119.1, 114.2, 110.3, 30.6, 29.8; FIRMS (DART): Calcd for M=$C_{12}H_9BrO$, [M+H]$^+$: 248.9910. Found: 248.9915.

6-Bromo-5-hydroxy-1,2-dihydroacenaphthylene-4-carbaldehyde (S15)

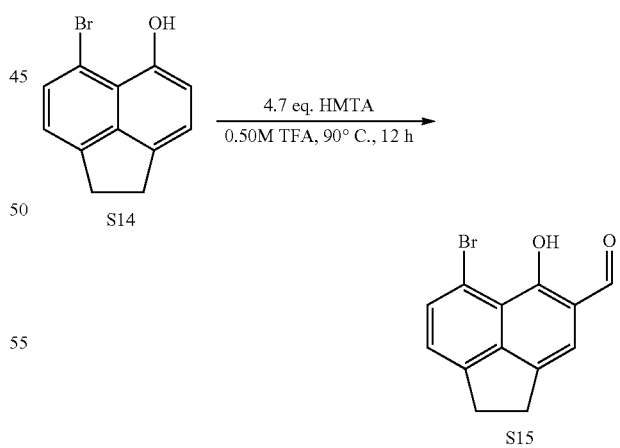

Under ambient conditions 6-bromo-1,2-dihydroacenaphthylen-5-ol (S14, 1.0 eq.), HMTA (4.7 eq.), and trifluoroacetic acid (0.50 M) were placed in a round bottom flask equipped with a stir bar and a reflux condenser. After stirring for 12 hours at 90° C., the reaction was cooled to 22° C. 1.0 M HCl was added, and the reaction mixture was allowed to stir for an additional 30 minutes. The aqueous layer was extracted with DCM, and organic layers were combined, dried with MgSO$_4$, and concentrated. 6-Bromo-5-hydroxy-1,2-dihydroacenaphthylene-4-carbaldehyde was purified using gradient silica gel column chromatography (100% hexanes→95:5 hexanes:Et$_2$O→90:10 hexanes:Et$_2$O→80:20 hexanes:Et$_2$O→60:40 hexanes:Et$_2$O) and was collected as a yellow solid (S15, 1.94 g, 87%). This column can be run as a short plug if sufficient separation is achieved by crude TLC. This column is necessary (unlike others). $^1$H NMR (500 MHz, CDCl$_3$): δ 13.20 (s, 1H), 9.94 (s, 1H), 7.70 (d, 1H, J=7.5 Hz), 7.29-7.24 (m, 2H), 3.32 (s, 4H); $^{13}$C NMR (125 MHz, CDCl$_3$): δ 196.8, 160.8, 145.5, 145.4, 136.7, 134.0, 125.12, 121.1, 121.0, 116.7, 115.2, 30.4, 29.4. HRMS (ESI): Calc'd for M=C$_{13}$H$_9$BrO$_2$ [M+H]+: 276.9859. Found: 276.9855.

6-Bromo-5-(methoxymethoxy)-1,2-dihydroacenaphthylene-4-carbaldehyde (S16)

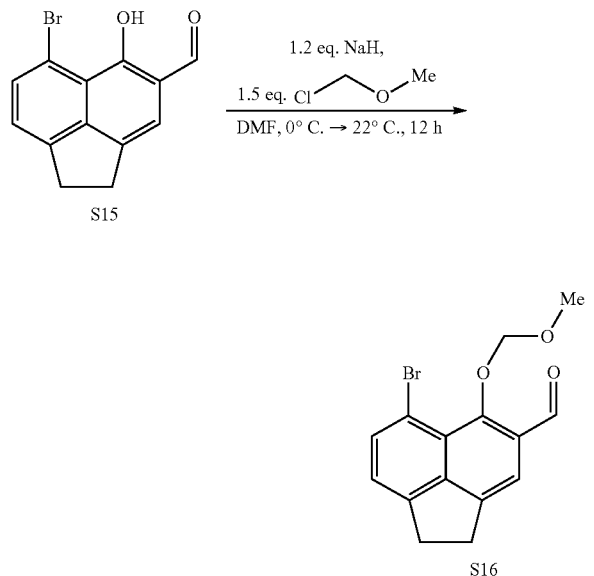

1.2 eq. of solid sodium hydride was weighed out in the glovebox and transferred to a small Schlenk flask, which was subsequently sealed and pumped out of the glovebox. Dry DMF was added via syringe to make a 0.88 M suspension, and the solution was cooled to 0° C. 6-Bromo-5-hydroxy-1,2-dihydroacenaphthylene-4-carbaldehyde (S15, 1.0 eq.) was added as a 2.5 M solution in DMF. The bromophenol is not very soluble in DMF, so it is acceptable to use additional solvent if necessary. Once hydrogen evolution ceased, chloromethyl methyl ether was added, and the solution warmed to 22° C. for 12 hours. 10% NaOH in water was added to the reaction, and the aqueous layer was extracted with 5% EtOAc in hexanes (3×). Organic layers were combined and washed with water (2×) and brine (1×), dried with MgSO$_4$, and concentrated. 6-Bromo-5-(methoxymethoxy)-1,2-dihydroacenaphthylene-4-carbaldehyde was collected as a yellow solid (S16, 1.87 g, 83%) which can be purified by gradient silica gel column chromatography. $^1$H NMR (500 MHz, CDCl$_3$): δ 10.55 (s, 1H), 7.76 (d, 1H, J=7.4 Hz), 7.71 (s, 1H), 7.24 (d, 1H, J=7.5 Hz), 5.22 (s, 2H), 3.62 (s, 3H), 3.36 (s, 4H); $^{13}$C NMR (125 MHz, CDCl$_3$): δ 191.8, 156.2, 146.7, 145.5, 143.3, 135.0, 130.1, 124.3, 123.6, 116.9, 112.8, 103.2, 58.5, 30.4, 30.0. FIRMS (ESI): Calc'd for M=C$_{15}$H$_{13}$BrO$_3$ [M+H]+: 321.0121. Found: 321.0135.

5-(Methoxymethoxy)-6-(4-methoxyphenyl)-1,2-dihydroacenaphthylene-4-carbaldehyde (S17)

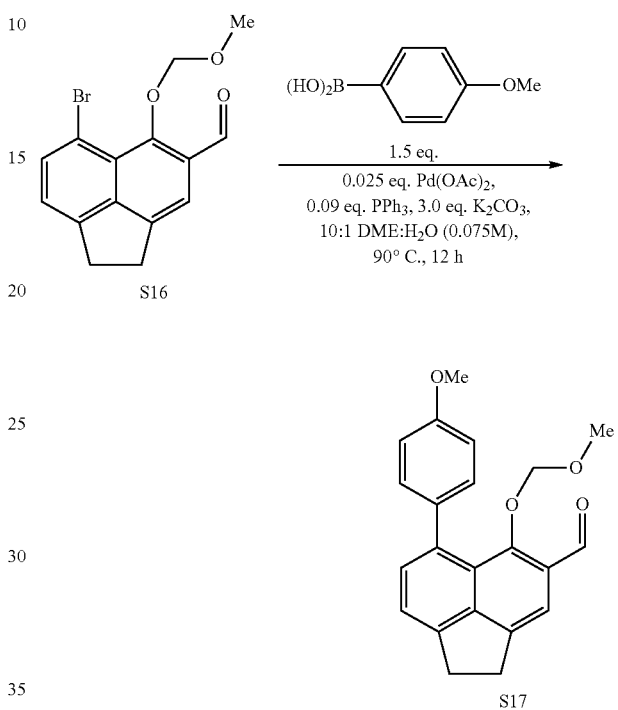

A flame-dried Schlenk flask equipped with a stir bar and fitted with a reflux condenser and Schlenk adapter was pumped onto the line from two directions. While both the Schlenk flask and Schlenk adapter were open to nitrogen, 6-bromo-5-(methoxymethoxy)-1,2-dihydroacenaphthylene-4-carbaldehyde (S16, 1.0 eq.), 4-methoxyphenylboronic acid (1.5 eq.), triphenylphosphine (0.09 eq.), potassium carbonate (3.0 eq.), and solvent (0.075 M, 10:1 DME:water; DME=1,2-dimethoxyethane) were added to the Schlenk flask. The solution was sparged with nitrogen for 30 minutes before adding palladium(II) acetate (0.025 eq.). The reaction stirred at 90° C. After 12 hours, the Schlenk flask was allowed to cool, and water was added. The aqueous layer was extracted with EtOAc (3×), and the organic layers were combined, dried with MgSO$_4$, and concentrated. 5-(Methoxymethoxy)-6-(4-methoxyphenyl)-1,2-dihydroacenaphthylene-4-carbaldehyde was purified by gradient silica gel column chromatography (100% hexanes→95:5 hexanes:Et$_2$O→90:10 hexanes:Et$_2$O→80:20 hexanes:Et$_2$O) and collected as a yellow solid (S17, 1.88 g, 93%). This column is necessary, unlike other synthetic steps. $^1$H NMR (500 MHz, CDCl$_3$): δ 10.53 (s, 1H), 7.72 (m, 1H), 7.45-7.44 (m, 1H), 7.41-7.37 (m, 3H), 6.99-6.97 (m, 2H), 4.14 (s, 2H), 3.90 (s, 3H), 3.46-3.39 (m, 4H), 3.28 (s, 3H); $^{13}$C NMR (125 MHz, CDCl$_3$): δ 192.2, 158.9, 157.7, 146.1, 145.0, 143.0, 135.7, 133.9, 132.3, 131.4, 129.2, 123.4, 122.2, 116.2, 116.0, 115.0, 113.0, 101.4, 58.0, 55.5, 30.5, 29.9. HRMS (ESI): Calcd for M=C$_{22}$H$_{20}$O$_4$, [M+H]+: 349.1434. Found: 349.1440.

5-Hydroxy-6-(4-methoxyphenyl)-1,2-dihydroacenaphthylene-4-carbaldehyde (S18)

rac-4,4'-((1E,1'E)-([1,1'-binaphthalene]-2,2'-diylbis(azaneylylidene))bis(methaneylylidene))bis(6-(4-methoxyphenyl)-1,2-dihydroacenaphthylen-5-ol) (S19)

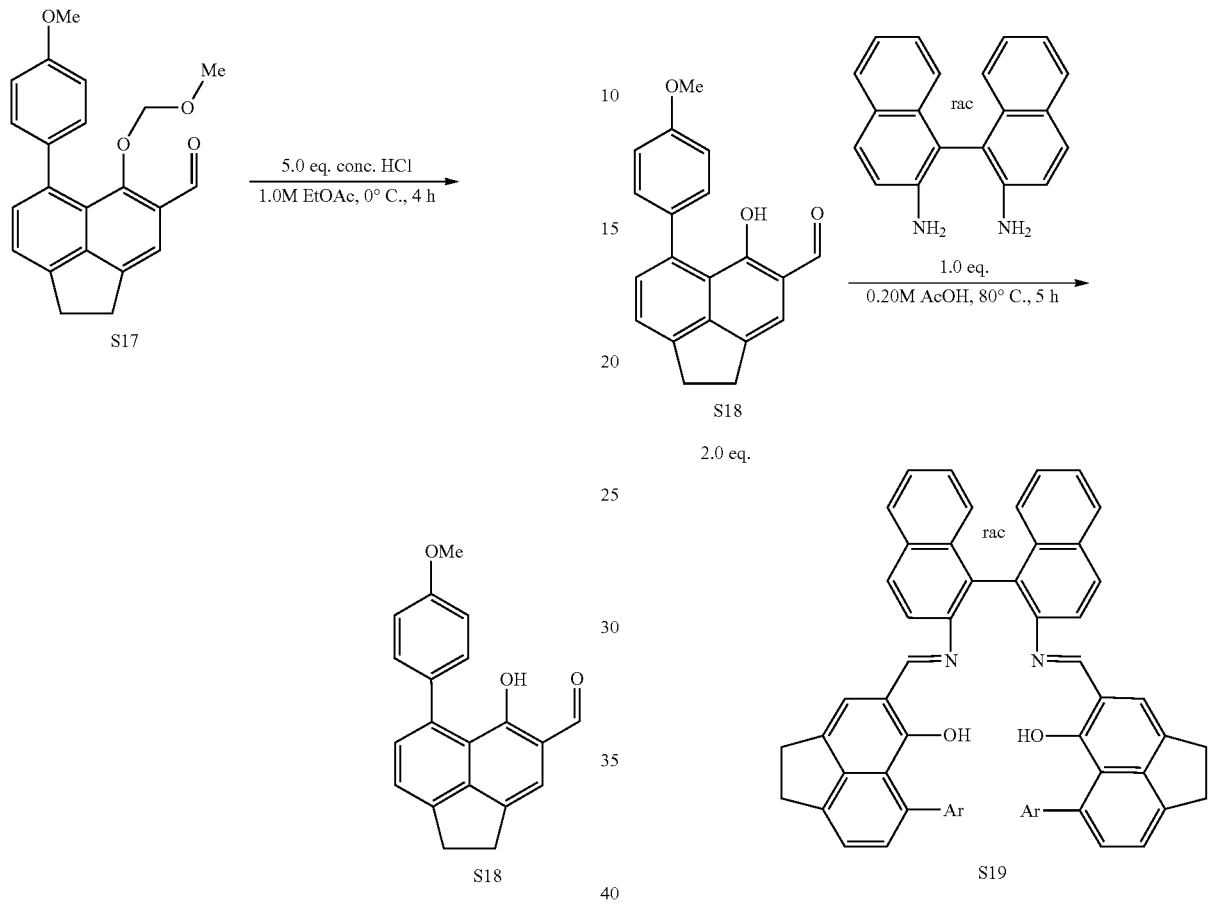

5-(Methoxymethoxy)-6-(4-methoxyphenyl)-1,2-dihydroacenaphthylene-4-carbaldehyde (S17, 1.0 eq.) was dissolved in benchtop EtOAc to make a 1.0 M solution, which was cooled to 0° C. in a 20 mL vial. 5.0 eq. of concentrated HCl was added dropwise, and conversion was monitored by crude $^1$H NMR. Once all the starting material was consumed, water was added, and the aqueous layer was extracted with EtOAc. Organic layers were combined, washed with NaHCO$_3$ (2×) and brine (1×), dried with MgSO$_4$, and concentrated. 5-hydroxy-6-(4-methoxyphenyl)-1,2-dihydroacenaphthylene-4-carbaldehyde was purified by gradient silica gel column chromatography (100% hexanes→95:5 hexanes:Et$_2$O→90:10 hexanes:Et$_2$O→80:20 hexanes:Et$_2$O) and collected as a yellow solid (S18, 1.34 g, 82%). $^1$H NMR (500 MHz, CDCl$_3$): δ 12.77 (s, 1H), 9.90 (s, 1H), 7.47 (d, 1H, J=7.1 Hz), 7.38 (d, 2H, J=8.1 Hz), 7.29 (d, 1H, J=7.2 Hz), 7.27-7.26 (m, 1H), 6.96 (d, 2H, J=8.2 Hz), 3.88 (s, 3H), 3.44-3.35 (m, 4H); $^{13}$C NMR (125 MHz, CDCl$_3$): δ 196.6, 161.7, 158.8, 144.9, 144.4, 138.0, 136.7, 134.8, 131.5, 130.8, 124.2, 120.4, 120.2, 116.5, 112.8, 55.4, 30.5, 29.3; HRMS (DART): Calcd for M=C$_{20}$H$_{16}$O$_3$, [M+H]$^+$: 305.1172. Found: 305.1177.

Solid S18 (2.0 eq.) and 1,1'-binaphthyl-2,2'-diamine (1.0 eq.) were weighed out and placed in a round bottom flask equipped with a stir bar. Acetic acid was added to form a 0.20 M solution (with respect to S18), which immediately turned red orange. The round bottom was fitted with a reflux condenser, and the reaction stirred at 80° C. for 5 hours. The reaction can easily be monitored by crude $^1$H NMR to determine percent consumption of salicylaldehyde. However, extremely dry deuterated solvent should be used to avoid imine hydrolysis. Upon completion, the reaction was cooled to 22° C. for at least 1 hour before filtering through a fine fritted filter. The solid was washed with pentane until the emerging filtrate became clear. The ligand was isolated as a red orange solid (S19, 310 mg, 94%). If the color appears to be brick red color, column chromatography (100% hexanes→80:20 hexanes:Et$_2$O to elute undesired products→DCM to elute the purified ligand) can be used to purify the ligand to avoid future catalyst reactivity issues. S19 was thoroughly dried before metalation. $^1$H NMR (500 MHz, CDCl$_3$): δ 14.06-14.05 (m, 2H), 8.25 (m, 2H), 7.93 (d, 2H, J=8.9 Hz), 7.90 (d, 2H, J=8.2 Hz), 7.44 (d, 2H, J=9.0 Hz), 7.39-7.36 (m, 2H), 7.27-7.25 (m, 2H, partially under CDCl$_3$ peak), 7.20-7.17 (m, 2H), 7.12-7.09 (m, 6H), 7.06 (d, 2H, J=7.2 Hz), 6.90 (d, 4H, J=8.5 Hz), 6.73 (s, 2H), 4.04 (s, 6H), 3.27-3.13 (m, 8H); $^{13}$C NMR (125 MHz, CDCl$_3$): δ 168.0, 158.2, 157.5, 144.3, 143.3, 141.0, 138.1, 135.7, 133.3, 133.3, 132.0, 130.7, 130.3, 130.2, 128.4, 127.0, 126.4, 125.8, 125.3, 123.3, 122.6, 120.7, 116.7, 113.7, 112.4, 55.6, 30.5, 29.0. HRMS (ESI): Calc'd for M=C$_{60}$H$_{44}$N$_2$O$_4$ [M+H]$^+$: 857.3374. Found: 857.3375.

rac-9AlCl

HSQC NMR shows chemical shifts overlapping between coupled partners, causing multiplets to be non-first order. HRMS (ESI): Calc'd for M=C$_{60}$H$_{42}$AlN$_2$O$_4$$^+$[M]: 881.2960. Found: 881.2954.

[rac-9Al(THF)$_2$][BPh$_4$]

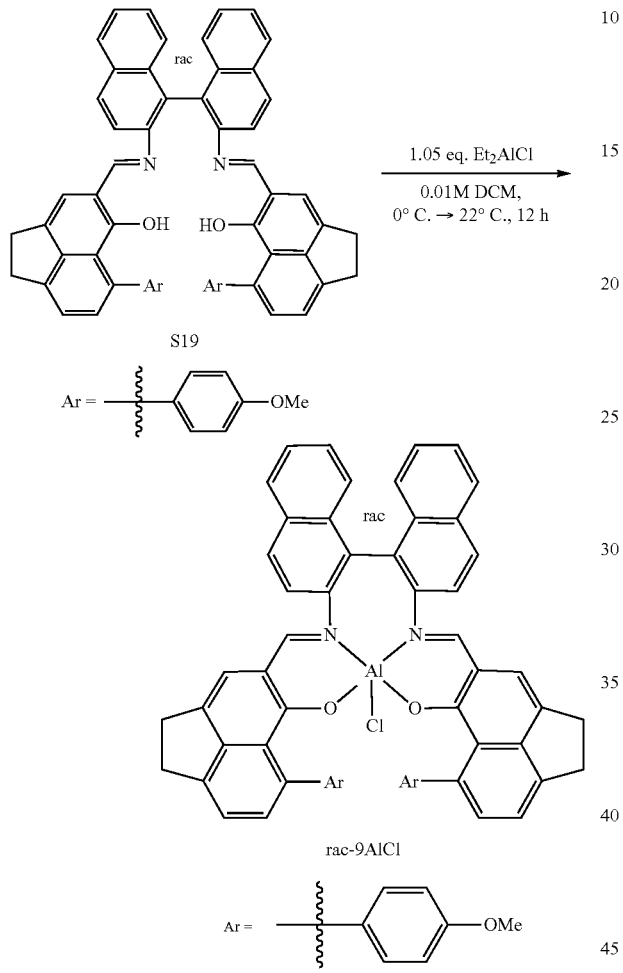

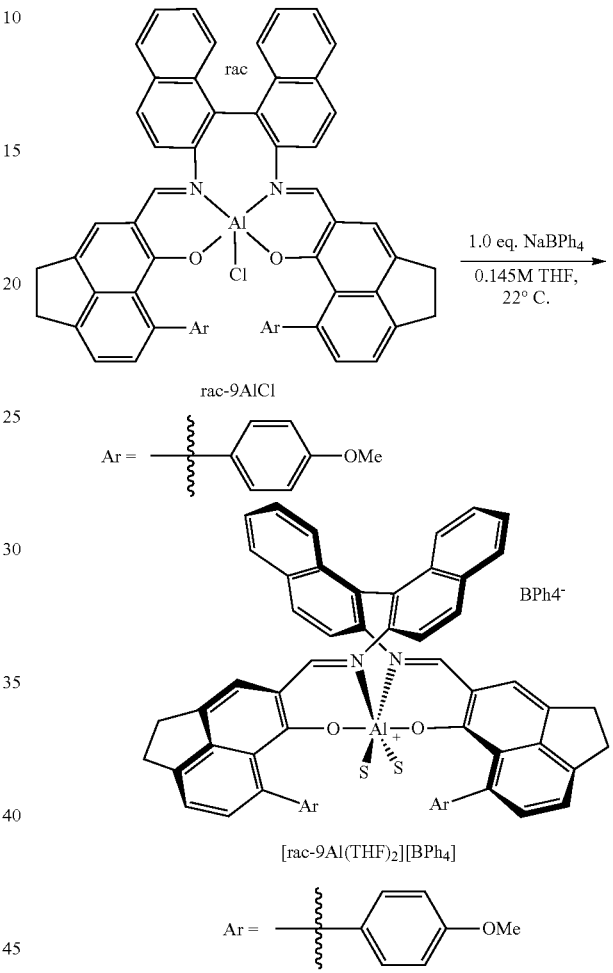

The ligand (S19, 1.0 eq.) was transferred into a pumped down, flame-dried Schlenk tube under nitrogen and was dissolved in dry DCM to make a 0.01 M solution. The reaction was cooled to 0° C. before the addition of 1.05 eq. of a 1.0 M diethylaluminum chloride solution in hexanes using a gas tight syringe. Upon addition the orange solution turns dark red. After 12 hours, solvent was stripped off using vacuum, yielding rac-9AlCl as a light orange solid (259 mg, 78%). If the color appears darker brown, resulting lactone regioselectivities may be affected. Consider purifying the ligand (S19) before metalation to avoid this discoloration. $^1$H NMR (600 MHz, CDCl$_3$): δ 8.25 (br s, 2H), 7.96-7.87 (m, 4H), 7.44-7.38 (m, 5H), 7.23-7.22 (m, 5H), 7.05 (br s, 2H), 6.54-6.53 (m, 4H), 3.35-3.10 (m, 14H); $^{13}$C NMR (125 MHz, CDCl$_3$): δ 158.1, 145.4, 145.0, 144.0, 139.4, 134.4, 134.0, 132.6, 132.4, 132.0, 130.9, 129.9, 128.4, 127.0, 126.9, 126.4, 125.9, 125.8, 124.3, 123.5, 121.2, 115.2, 111.9, 54.8, 30.5, 29.0, Note that some peaks are broad (145.4, 139.4, 132.0, 126.4, 124.3). Methoxy peaks and some aryl peaks are broad due to dynamics.

A Schlenk flask of rac-9AlCl (1.0 eq) was pumped into the glovebox under vacuum. Sodium tetraphenylborate (1.0 eq) was weighed into a scintillation vial and poured into the Schlenk flask. The vial was then washed out with a portion of the THF required to produce a 0.145 M solution. The rest of the THF was used to wash down the sides of the Schlenk flask, which was subsequently sealed up and allowed to stir at 22° C. for 48 hours. Overtime the solution became lighter and a precipitate (NaCl) appeared. More THF was added to the flask before the solution was cannula filtered through Celite® and concentrated. Crystals suitable for single crystal X-ray diffraction analysis were observed when the resulting crude reaction mixture was allowed to stand without stirring for 72 hours. $^1$H NMR (600 MHz, CDCl$_3$): δ 7.92-7.91 (m, 3H), 7.64-7.45 (m, 7H), 7.37-7.35 (m, 6H), 7.22-6.97 (m, 6H), 6.88 (app. t, 6H, J=7.3 Hz), 6.78 (app. t, 3H, J=6.9 Hz), 6.73-6.40 (m, 4H), 3.74 (br s, 8H), 3.39-2.79 (m, 14H), 1.84 (br s, 8H). Due to solubility issues, a characterization quality $^{13}$C NMR was not obtained. HRMS (ESI): Calc'd for M=$C_{60}H_{42}AlN_2O_4^+$[M]: 881.2960. Found: 881.2939. See below for the previously mentioned solid state structure of [rac-9Al(THF)$_2$][BPh$_4$].

General Procedure A: Contrasteric Carbonylation of Isobutylene Oxide

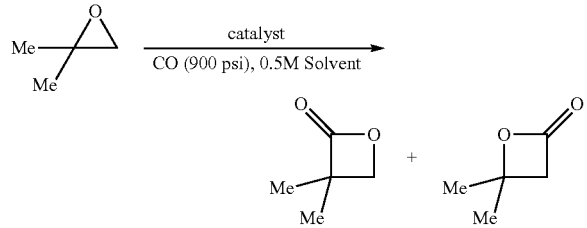

In a glovebox, a 4 mL glass vial equipped with a Teflon-coated magnetic stir bar and septum cap was charged with catalyst and solvent (0.5 M with respect to epoxide). The contents were allowed to stir for two minutes before the septum was pierced with a needle and the vial was placed in a custom-made six-well high-pressure reactor. The reactor bottom was stored in a freezer for 30 minutes, and isobutylene oxide was then quickly added dropwise to the vial by weight. The reactor was subsequently sealed, taken out of the glovebox, placed in a well-ventilated hood, and pressurized with carbon monoxide (900 psi). The closed reactor stirred for the indicated time.

Pivalolactone (2)

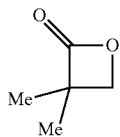

Analytical data match literature values. $^1$H NMR (600 MHz, CDCl$_3$): δ 4.08 (s, 2H), 1.42 (s, 6H).

4,4-Dimethyloxetan-2-one (3)

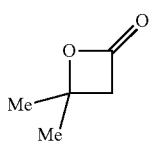

Analytical data match literature values. $^1$H NMR (500 MHz, CDCl$_3$): δ 3.16 (s, 2H), 1.59 (s, 6H); $^{13}$C NMR (125 MHz, CDCl$_3$): δ 167.48, 76.18, 48.64, 26.37.

X-ray Crystallography. Low-temperature X-ray diffraction data for (rac)-8aAlCl and [rac-9Al(THF)$_2$][BPh$_4$] were collected on a Rigaku XtaLAB Synergy diffractometer coupled to a Rigaku Hypix detector with Cu Kα radiation (λ=1.54184 Å), from a PhotonJet micro-focus X-ray source at 100 K. The diffraction images were processed and scaled using the CrysAlisPro software. The structures were solved through intrinsic phasing using SHELXT and refined against $F^2$ on all data by full-matrix least squares with SHELXL following established refinement strategies. All non-hydrogen atoms were refined anisotropically. All hydrogen atoms bound to carbon were included in the model at geometrically calculated positions and refined using a riding model. The isotropic displacement parameters of all hydrogen atoms were fixed to 1.2 times the Ueq value of the atoms they are linked to (1.5 times for methyl groups).

Crystal data and structure refinement for (rac)-8aAlCl.

| | |
|---|---|
| Identification code | rkk1_abs |
| Empirical formula | C57 H37 Al Cl10 N2 O2 |
| Formula weight | 1163.36 |
| Temperature | 100.00(10) K |
| Wavelength | 1.54184 Å |
| Crystal system | Monoclinic |
| Space group | P 1 21/c 1 |
| Unit cell dimensions | a = 12.23600(10) Å α = 90°. |
| | b = 21.43260(10) Å β = 103.8410(10)°. |
| | c = 20.17230(10) Å γ = 90°. |
| Volume | 5136.56(6) Å$^3$ |
| Z | 4 |
| Density (calculated) | 1.504 Mg/m$^3$ |
| Absorption coefficient | 5.507 mm$^{-1}$ |
| F(000) | 2368 |
| Crystal size | 0.319 × 0.102 × 0.053 mm$^3$ |
| Theta range for data collection | 3.056 to 70.070°. |
| Index ranges | −14 <= h <= 14, |
| | −26 <= k <= 24, |
| | −24 <= l <= 24 |
| Reflections collected | 46691 |
| Independent reflections | 9742 [R(int) = 0.0251] |
| Completeness to theta = 67.684° | 99.9% |
| Absorption correction | Gaussian |
| Max. and min. transmission | 0.833 and 0.379 |
| Refinement method | Full-matrix least-squares on F$^2$ |
| Data/restraints/parameters | 9742/0/686 |
| Goodness-of-fit on F$^2$ | 1.029 |
| Final R indices [I > 2sigma(I)] | R1 = 0.0352, wR2 = 0.0953 |
| R indices (all data) | R1 = 0.0366, wR2 = 0.0962 |
| Extinction coefficient | n/a |
| Largest diff. peak and hole | 0.835 and −0.726 e.Å$^{-3}$ |

Crystal data and structure refinement for [rac-9Al(THF)$_2$][BPh$_4$].

| | |
|---|---|
| Identification code | rkk1_abs |
| Empirical formula | C96 H86 Al B N2 O7 |
| Formula weight | 1417.45 |
| Temperature | 100.00(10) K |
| Wavelength | 1.54184 Å |
| Crystal system | Monoclinic |
| Space group | P 1 n 1 |
| Unit cell dimensions | a = 14.16596(4) Å α = 90°. |
| | b = 24.26807(8) Å β = 95.3470(3)°. |
| | c = 21.69468(7) Å γ = 90°. |
| Volume | 7425.75(4) Å$^3$ |
| Z | 4 |
| Density (calculated) | 1.268 Mg/m$^3$ |
| Absorption coefficient | 0.723 mm$^{-1}$ |
| F(000) | 3000 |
| Crystal size | 0.187 × 0.159 × 0.058 mm$^3$ |
| Theta range for data collection | 1.820 to 78.077°. |
| Index ranges | −17 <= h <= 16, |
| | −30 <= k <= 30, |
| | −27 <= l <= 27 |
| Reflections collected | 367185 |
| Independent reflections | 30389 [R(int) = 0.0483] |
| Completeness to theta = 67.684° | 100.0% |
| Absorption correction | Gaussian |
| Max. and min. transmission | 1.000 and 0.474 |
| Refinement method | Full-matrix least-squares on F$^2$ |
| Data/restraints/parameters | 30389/2/1931 |
| Goodness-of-fit on F$^2$ | 1.030 |

| | |
|---|---|
| Final R indices [I > 2sigma(I)] | R1 = 0.0393, wR2 = 0.1056 |
| R indices (all data) | R1 = 0.0404, wR2 = 0.1066 |
| Absolute structure parameter | −0.002(7) |
| Extinction coefficient | n/a |
| Largest diff. peak and hole | 0.416 and −0.301 e.Å$^{-3}$ |

Although the present disclosure has been described with respect to one or more particular embodiments and/or examples, it will be understood that other embodiments and/or examples of the present disclosure may be made without departing from the scope of the present disclosure.

The invention claimed is:

1. A method of producing an α,α-disubstituted carbonyl compound comprising:
   providing a reaction mixture comprising a 2,2-disubstituted epoxide and a catalyst; and
   contacting the reaction mixture with carbon monoxide, wherein the α,α-disubstituted carbonyl compound is produced and the α,α-disubstituted carbonyl compound is the major carbonyl compound product.

2. The method of claim 1, wherein the catalyst is formed in situ from a reaction with a catalytic precursor and a metal source.

3. The method of claim 1, wherein the catalyst is present in the reaction mixture at a concentration of 0.05 to 10 mol %.

4. The method of claim 1, wherein the reaction mixture further comprises one or more solvents.

5. The method of claim 4, wherein the solvents are chosen from THF, 1,3-dioxane, 1,4-dioxane, diethyl ether, toluene, dibasic esters, $^i$Pr$_2$O, ethyl acetate, $^t$butyl acetate, and combinations thereof.

6. The method of claim 1, wherein the reaction mixture is pressurized to 0.1 to 2000 psig with CO.

7. The method of claim 1, wherein the catalyst comprises a cationic Lewis acid having the formula [Lewis acid]$^{z+}$ and anionic metal carbonyl having the formula $\{[QM(CO)_x]^{w-}\}_y$, wherein Q is any ligand and is optional, M is a transition metal chosen from transition metals of Groups 4, 5, 6, 7, 8, 9, and 10 of the periodic table of elements, z is the valence of the Lewis acid and ranges from 1 to 6, w is the charge of the metal carbonyl and ranges from 1 to 4, y is a number such that w times y equals z, and x is a number such as to provide a stable anionic metal carbonyl for $\{[QM(CO)_x]^{w-}\}_y$, and ranges from 1 to 9.

8. The method of claim 1, wherein the method is carried out in a single vessel without separating or isolating various possible intermediates.

9. The method of claim 1, wherein the 2,2-disubstituted epoxide has the following structure:

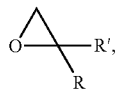

wherein R and R' are independently substituted or unsubstituted alkyl groups that are the same or different or R and R' are connected such that they form a substituted or unsubstituted carbocycle or substituted or unsubstituted heterocycle.

10. The method of claim 9, wherein the 2,2-disubstituted epoxide is spirocyclic 2,2-disubstituted epoxide comprising a non-epoxide ring chosen from substituted or unsubstituted cyclopropanes, substituted or unsubstituted cyclobutanes, substituted or unsubstituted cyclopentanes, substituted or unsubstituted cyclohexanes, substituted or unsubstituted cycloheptanes, and substituted or unsubstituted cyclooctanes.

11. The method of claim 9, wherein the 2,2-disubstituted epoxide is chosen from:

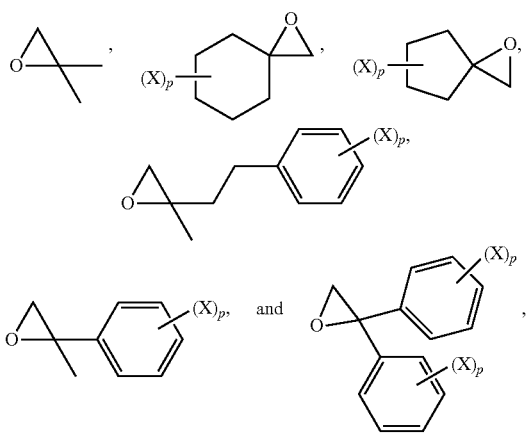

wherein each X at each occurrence is independently chosen from H, alkoxy groups, alkyl groups, aryl groups, halide groups, amino groups, alkenyl groups, alkynyl groups, acyl groups, nitro groups, nitrile groups, thioether groups, and p is 0-10.

12. A method of claim 11, wherein the 2,2-disubstituted epoxide is chosen from:

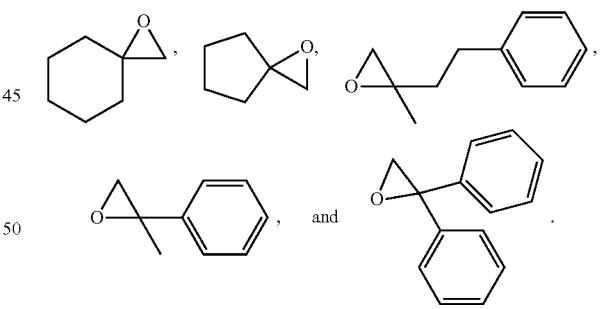

13. The method of claim 1, wherein the α,α-disubstituted carbonyl compound is an α,α-disubstituted β-lactone and the method produces the α,α-disubstituted β-lactone and a β,β-disubstituted β-lactone and the α,α-disubstituted β-lactone to β,β-disubstituted β-lactone ratio is 50:50 to >99:<1.

* * * * *